United States Patent
Morrison et al.

(10) Patent No.: US 7,998,678 B2
(45) Date of Patent: Aug. 16, 2011

(54) METHODS FOR THE DETECTION OF LUNG CANCER

(75) Inventors: Larry E. Morrison, Glen Ellyn, IL (US); Irina A. Sokolova, Villa Park, IL (US); Steven A. Seelig, Elmhurst, IL (US); Kevin C. Halling, Rochester, MN (US)

(73) Assignees: VYSIS, Inc., Downers Grove, IL (US); Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 12/536,647

(22) Filed: Aug. 6, 2009

(65) Prior Publication Data

US 2009/0298087 A1    Dec. 3, 2009

Related U.S. Application Data

(60) Continuation of application No. 11/259,771, filed on Oct. 27, 2005, now abandoned, which is a division of application No. 10/081,393, filed on Feb. 20, 2002, now abandoned.

(60) Provisional application No. 60/270,271, filed on Feb. 20, 2001.

(51) Int. Cl.
C12Q 1/68 (2006.01)
C07H 21/02 (2006.01)
C07H 21/04 (2006.01)

(52) U.S. Cl. .......................... 435/6; 536/23.1; 536/24.31

(58) Field of Classification Search .................. None
See application file for complete search history.

(56) References Cited

U.S. PATENT DOCUMENTS

| | | | |
|---|---|---|---|
| 5,491,224 | A | 2/1996 | Bittner et al. |
| 5,658,730 | A | 8/1997 | McGill et al. |
| 5,658,792 | A | 8/1997 | Nuell et al. |
| 5,670,314 | A | 9/1997 | Christman et al. |
| 5,776,688 | A | 7/1998 | Bittner et al. |
| 5,856,097 | A | 1/1999 | Pinkel et al. |
| 5,919,624 | A | 7/1999 | Ried et al. |
| 6,127,126 | A | 10/2000 | Vogelstein et al. |
| 6,174,681 | B1 | 1/2001 | Halling et al. |
| 6,180,349 | B1 | 1/2001 | Ginzinger |
| 6,376,188 | B1 | 4/2002 | Halling et al. |
| 2009/0298087 | A1 * | 12/2009 | Morrison et al. .................. 435/6 |

FOREIGN PATENT DOCUMENTS

| | | |
|---|---|---|
| EP | 1035215 A2 | 9/2000 |
| EP | 1048740 A2 | 11/2000 |

OTHER PUBLICATIONS

Taguchi (et al. Cancer Genetics and Cytogenetics. 1996. 89: 120-125.*
Bryce et al. Neoplasia. 2000. 2(3): 197-201.*
Kasprzyk et al. Leukemia. 1997. 11: 429-435.*
Nath et al. Biotechnic and Histochemistry. 1997. 7: 6-22.*
Nath and Johnson, Biotechnic & Histochemistry 73, No. 1, (1998): 6-22.
Wheeless et al., Cytometry 17, (1994): 319-326.
Cragg et al., Current Opinion in Immunol. 11 (1999): 541-547.
Jia D. et al., "Application of Fluorescence in situ Hybridization (FISH) in Sputum Cytologic Diagnosis of Lung Cancer," Chin. J. Oncol. 22, No. 6 (2000): 477-479. (Abstract only).
Schenk et al., "Detection of Chromosomal Aneuploidy by Interphase Fluorescence in situ Hybridization in Bronchoscopically Gained Cells from Lung Cancer Patients," CHEST 111, No. 6, (1997): 1691-1696.
Levin et al., "Identification of Frequent Novel Genetic Alterations in Small Cell Lung Carcinoma," Cancer Research 54, (1994): 5086-5091.
Levin et al., "Identification of Novel Regions of Altered DNA Copy Number in Small Cell Lung Tumors," Genes Chromasom Cancer 13 (1995): 175-185 (XP008038794).
Nederlof et al., "Three-Color Fluorescence in situ Hybridization for the Simultaneous Detection of Multiple Nucleic Acid Sequences," Cytometry 10, (1989): 20-27.
Ried et al., "Mapping of Multiple DNA Gains and Losses in Primary Small Cell Lung Carcinomas by Comparative Genomic Hybridization," Cancer Research 54, (1994): 1801-1806 (XP008038899).
Taguchi et al. Cancer Genetics and Cytogenetics 89 (1996):120-125.
Sauter et al. Urol. Research. 25 (Supplement 1) (1997):S37-S43.
Kasprzyk et al. Leukemia 11 (1997):429-435.
Michelland et al. Cancer Genet. Cytogenet. 114 (1999):22-30.
Kubokura et al. J. Nippon Med. Sch. 66 (1999):25-30.
Taguchi et al. Genes and Chromosomes & Cancer 20 (1997):208-212.
Bryce et al. Neoplasia 2 (2000):197-201.

* cited by examiner

*Primary Examiner* — Carla Myers
(74) *Attorney, Agent, or Firm* — Pierce Atwood LLP; Kevin M. Farrell; David J. Wilson

(57) ABSTRACT

Probe sets and methods of using probes and probe sets for the detection of cancer are described. Methods for detecting cancer that include hybridizing a set of chromosomal probes to a biological sample obtained from a patient, and identifying if cancer cells are present the sample. Also included are methods of selecting a combination of probes for the detection of cancer.

4 Claims, 1 Drawing Sheet

METHODS FOR THE DETECTION OF LUNG CANCER

RELATED APPLICATIONS

The present application is a Continuation of U.S. patent application Ser. No. 11/259,771 filed on Oct. 27, 2005 (pending) which is a Division of U.S. patent application Ser. No. 10/081,393 filed on Feb. 20, 2002 (abandoned) which is a Non-Provisional of U.S. Patent Application Ser. No. 60/270,271 filed on Feb. 20, 2001 and is herein incorporated by reference.

FIELD OF THE INVENTION

The invention relates to methods and probes for the detection of cancer.

BACKGROUND OF THE INVENTION

Lung cancer is the leading cause of death due to cancer in the United States, killing approximately 156,000 men and women each year. There are four major bronchogenic carcinoma cell types that account for over 95% of primary lung cancers: adenocarcinoma; squamous cell carcinoma; large cell carcinoma; and small cell carcinoma. These cell types occur singly or in combination. The remaining 5% of tumors are composed of several unusual tumor types.

When lung cancer develops, it tends to spread from the original cancer site to the lymph nodes, and then, either at the same time or sequentially, to other areas of the body. The most common sites for lung cancer to spread (metastasis) are the brain, bones, liver, adrenal glands, and any other organ with a high rate of blood flow. It is this process of metastasis that leads to fatality in most patients.

When a cancer is first discovered by physical examination or by diagnostic tests (e.g., X-ray or high resolution imaging such as spiral CT), it is usually at least 1 cm in size. A cancer that is 1 cm in size contains at least about 1 billion cells.

Changes in chromosomal DNA have been shown to accompany the conversion of normal cells to malignant cells. Because of this, detection of specific chromosomal alterations provides a route to detecting and diagnosing lung cancer.

SUMMARY OF THE INVENTION

The invention is based on the discovery that specific probes and probe sets can be used to detect lung cancer with high levels of sensitivity. By using the probes described herein, lung cancer can be detected with enhanced sensitivity as compared to conventional methods. Accordingly, the probes and methods of the invention facilitate the detection of lung cancer and/or allow for the detection of lung cancer at early stages. The invention includes probe sets, methods of using probes and probe sets, and methods of selecting probe sets for the detection of cancer.

In one aspect, the invention features set of chromosomal probes including any of the following combinations of two probes: (a) a 5p chromosome arm probe and a probe selected from the group consisting of a 8q24 locus specific probe, a 3q chromosome arm probe, a 20q chromosome arm probe, a 7p12 locus specific probe, a chromosome 16 enumeration probe, a chromosome 4 enumeration probe, a chromosome 12 enumeration probe, a chromosome 6 enumeration probe, and a 17q21 locus specific probe; (b) a 8q24 locus specific probe and a probe selected from the group consisting of a chromosome 17 enumeration probe, a chromosome 1 enumeration probe, and a chromosome 6 enumeration probe; (c) a 7p12 locus specific probe and a probe selected from the group consisting of a 3q chromosome arm probe and a chromosome 6 enumeration probe; (d) a 3q chromosome arm probe and a chromosome 7 enumeration probe; or (e) a chromosome 6 enumeration probe and a chromosome 7 enumeration probe.

A detection moiety can be attached to the two probes. The detection moiety can contain a fluorescent label. The two probes can optionally be coupled to different detection moieties. For example, the detection moieties can contain fluorescent labels.

In another aspect, the invention features a set of chromosomal probes including any of the following combinations of three probes: (a) a 5p15 locus specific probe, a 8q24 locus specific probe, and a probe selected from the group consisting of a 9p21 locus specific probe, a chromosome 1 enumeration probe, a chromosome 6 enumeration probe, a 7p12 locus specific probe, and a 17q21 locus specific probe; (b) a 5p15 locus specific probe, a chromosome 12 enumeration probe, and a 9p21 locus specific probe; (c) a 8q24 locus specific probe, a chromosome 17 enumeration probe, and a 9p21 locus specific probe; (d) a 8q24 locus specific probe, a chromosome 1 enumeration probe, and a 9p21 locus specific probe; or (e) a 5p15 locus specific probe, a 3q chromosome arm probe, and a chromosome 12 enumeration probe.

In another aspect, the invention features a set of chromosomal probes including any of the following combinations of four probes: (a) a 5p15 locus specific probe, a chromosome 6 enumeration probe, a 17p13 locus specific probe, and a chromosome 17 enumeration probe; (b) a 5p15 locus specific probe, a 8q24 locus specific probe, a chromosome 1 enumeration probe, and a 7p12 locus specific probe; (c) a 5p15 locus specific probe, a 8q24 locus specific probe, a 3q chromosome arm probe, and a 7p12 locus specific probe; (d) a 5p15 locus specific probe, a 8q24 locus specific probe, a 20q chromosome arm probe, and a 7p12 locus specific probe; (e) a 5p15 locus specific probe, a 8q24 locus specific probe, a 7p12 locus specific probe, and a 17q21 locus specific probe; (f) a 5p15 locus specific probe, a 8q24 locus specific probe, a chromosome 6 enumeration probe, and a 7p12 locus specific probe; (g) a 5p5 locus specific probe, a 8q24 locus specific probe, a chromosome 6 enumeration probe, and a chromosome 1 enumeration probe; (h) a 5p15 locus specific probe, a 8q24 locus specific probe, a chromosome 6 enumeration probe, and a chromosome 12 enumeration probe; (i) a 5p15 locus specific probe, a chromosome 1 enumeration probe, a chromosome 6 enumeration probe, and a chromosome 12 enumeration probe; (j) a chromosome 7 enumeration probe, a chromosome 1 enumeration probe, a chromosome 6 enumeration probe, and a chromosome 12 enumeration probe; or (k) a 5p chromosome arm probe, a chromosome 1 enumeration probe, a chromosome 6 enumeration probe, and a chromosome 7 enumeration probe.

In some embodiments of the probe sets described herein, e.g., a set containing at least two, three, or four probes, a 5p chromosome arm probe can be used in place of a 5p15 locus specific probe. In other embodiments of the probe sets described herein, a 7p chromosome arm probe can be used in place of a 7p12 locus specific probe.

In another aspect, the invention features a method of screening for lung cancer in a subject, the method including the steps of: (a) obtaining a biological sample from the subject; (b) obtaining a set of at least two different chromosomal probes, e.g., at least two, three, or four probes, from a set described herein; (c) contacting the set of probes to the biological sample under conditions sufficient to enable hybridization of probes in the set to chromosomes in the sample, if any; and (d) detecting the hybridization pattern of the set of chromosomal probes to the biological sample to determine whether the subject has lung cancer.

The probes used in the methods described herein can be selected from the group consisting of a chromosome 1 enumeration probe, a chromosome 3 enumeration probe, a chromosome 4 enumeration probe, a chromosome 6 enumeration probe, a chromosome 7 enumeration probe, a chromosome 8 enumeration probe, a chromosome 9 enumeration probe, a chromosome 10 enumeration probe, a chromosome 11 enumeration probe, a chromosome 12 enumeration probe, a chromosome 16 enumeration probe, a chromosome 17 enumeration probe, a chromosome 18 enumeration probe, a 3p14 locus specific probe, a 3q26 locus specific probe, a 5p15 locus specific probe, a 5q31 locus specific probe, a 7p12 locus specific probe, a 8q24 locus specific probe, a 9p21 locus specific probe, a 10q23 locus specific probe, a 13q14 locus specific probe, a 17p13 locus specific probe, a 17q21 locus specific probe, a 20q13 locus specific probe, a 21q22 locus specific probe, a 3q chromosome arm probe, a 5p chromosome arm probe, a 7p chromosome arm probe, a 3p chromosome arm probe, and a 20q chromosome arm probe.

The biological sample used in the methods described herein can contain a bronchial specimen, a lung biopsy, or a sputum sample. The chromosomal probes used in the methods described herein can optionally be fluorescently labeled. The methods described herein can further include performing cytological analysis on the sample.

In another aspect, the invention features a method of screening for lung cancer in a subject, the method including the steps of: (a) obtaining a biological sample from the subject; (b) obtaining a chromosomal probe selected from the group consisting of a 5p15 locus specific probe, a chromosome 1 enumeration probe, a 7p12 locus specific probe, a 8q24 locus specific probe, and a chromosome 9 enumeration probe; (c) contacting the chromosomal probe to the biological sample under conditions sufficient to enable hybridization of the probe to chromosomes in the sample, if any; and (d) detecting the hybridization pattern of the probe to the biological sample to determine whether the subject has lung cancer.

In another aspect, the invention features a method of selecting a combination of probes for the detection of cancer, the method including the steps of: (a) providing a first plurality of chromosomal probes; (b) determining the ability of each of the first plurality of probes to distinguish cancer specimens from normal specimens; (c) selecting those probes within the first plurality of probes that identify the cancer specimens as compared to the normal specimens to yield a second plurality of probes, wherein the second plurality of probes each identify the cancer specimens as compared to the normal specimens at a p value of less than 0.01 or a vector value of less than 0.500; (d) determining the ability of a combination of probes selected from the second plurality of probes to distinguish the cancer specimens from the normal specimens; and (e) selecting a combination of probes that identifies the cancer specimen as compared to the normal specimen with a vector value of less than 0.400.

In one embodiment, the cancer specimens are lung cancer specimens. For example, the specimens can be derived from patients diagnosed as having lung cancer. The normal specimens can be lung tissue specimens derived from patients not diagnosed as having lung cancer.

In one embodiment, step (c) of the method includes selecting those probes within the first plurality of probes that identify the cancer specimens as compared to the normal specimens to yield a second plurality of probes, wherein the second plurality of probes each identify the cancer specimens as compared to the normal specimens at a p value of less than 0.005 or 0.001 and/or a vector value of less than 0.400, 0.300, 0.200, or 0.100.

In another embodiment, step (e) of the method includes selecting a combination of probes that identifies the cancer specimen as compared to the normal specimen with a vector value of less than 0.300, 0.200, or 0.100.

In another aspect, the invention features a set of chromosomal probes including at least two different probes, wherein the set of probes is capable of detecting lung cancer with a sensitivity of at least about 60%, e.g., when tested on a population containing at least 35 lung cancer patients.

In one example, the set contains at least three different probes. In another example, the set contains at least four different probes.

In one example, the set is capable of detecting lung cancer with a sensitivity of at least about 60% at a cutoff value of about 10%. In another example, the set is capable of detecting lung cancer with a sensitivity of at least about 70% when the detection is performed on a biological sample containing a bronchial specimen. In another example, the set is capable of detecting lung cancer with a sensitivity of at least about 80% at a cutoff value of about 20%.

The chromosomal probes contained in the sets described herein, e.g., sets of at least two, three, or four different probes, can be selected from the group consisting of a chromosome 1 enumeration probe, a chromosome 3 enumeration probe, a chromosome 4 enumeration probe, a chromosome 6 enumeration probe, a chromosome 7 enumeration probe, a chromosome 8 enumeration probe, a chromosome 9 enumeration probe, a chromosome 10 enumeration probe, a chromosome 11 enumeration probe, a chromosome 12 enumeration probe, a chromosome 16 enumeration probe, a chromosome 17 enumeration probe, a chromosome 18 enumeration probe, a 3p14 locus specific probe, a 3q26 locus specific probe, a 5p15 locus specific probe, a 5q31 locus specific probe, a 7p12 locus specific probe, a 8q24 locus specific probe, a 9p21 locus specific probe, a 10q23 locus specific probe, a 13q14 locus specific probe, a 17p13 locus specific probe, a 17q21 locus specific probe, a 20q13 locus specific probe, a 21 q22 locus specific probe, a 3q chromosome arm probe, a 5p chromosome arm probe, a 7p chromosome arm probe, a 3p chromosome arm probe, and a 20q chromosome arm probe.

In another aspect, the invention features a set of chromosomal probes including at least two different probes, wherein the set is capable of detecting lung cancer with a vector value of less than 0.500, e.g., when tested on a population containing at least 35 lung cancer patients and 20 normal individuals.

In one example, the set is capable of detecting lung cancer with a vector value of less than 0.500 at a cutoff value of about 10%. In another example, the se is capable of detecting lung cancer with a vector value of less than 0.400. In another example, the set is capable of detecting lung cancer with a vector value of less than 0.400 at a cutoff value of about 15%. In another example, the set is capable of detecting lung cancer with a vector value of less than 0.300. In another example, the set is capable of detecting lung cancer with a vector value of less than 0.300 at a cutoff value of about 15%. In another example, the set is capable of detecting lung cancer with a vector value of less than 0.200. In another example, the set is capable of detecting lung cancer with a vector value of less than 0.200 at a cutoff value of about 20%.

The at least two different probes of the set can be selected from the group consisting of a chromosome 1 enumeration probe, a chromosome 3 enumeration probe, a chromosome 4 enumeration probe, a chromosome 6 enumeration probe, a chromosome 7 enumeration probe, a chromosome 8 enumeration probe, a chromosome 9 enumeration probe, a chromosome 10 enumeration probe, a chromosome 11 enumeration probe, a chromosome 12 enumeration probe, a chromosome 16 enumeration probe, a chromosome 17 enumeration probe, a chromosome 18 enumeration probe, a 3p14 locus specific probe, a 3 q26 locus specific probe, a 5p15 locus specific probe, a 5q3 locus specific probe, a 7p12 locus specific probe, a 8q24 locus specific probe, a 9p21 locus specific probe, a 10q23 locus specific probe, a 13q14 locus specific probe, a 17p13 locus specific probe, a 17q21 locus specific probe, a 20q13 locus specific probe, a 21q22 locus specific probe, a 3q chromosome arm probe, a 5p chromosome arm probe, a 7p chromosome arm probe, a 3p chromosome arm probe, and a 20q chromosome arm probe.

An advantage of the invention is that it allows for the detection of lung cancer with improved sensitivity, as compared to conventional methods such as cytology. These probes and methods can thus allow for the early detection of lung cancer, e.g., at a pre-invasive stage.

Another advantage of the invention is that it allows for the detection of cancer cells based on genetic alterations, rather than gross morphological changes in cell structure. Genetic alterations can be detected at an early stage, e.g., before the occurrence of visually detectable changes in cell structure.

Unless otherwise defined, all technical and scientific terms used herein have the same meaning as commonly understood by those of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of a conflict in terminology, the present specification will control. In addition, the described materials and methods are illustrative only and are not intended to be limiting.

Other features and advantages of the invention will be apparent from the following detailed description and the claims.

DETAILED DESCRIPTION OF THE INVENTION

Figure 1:
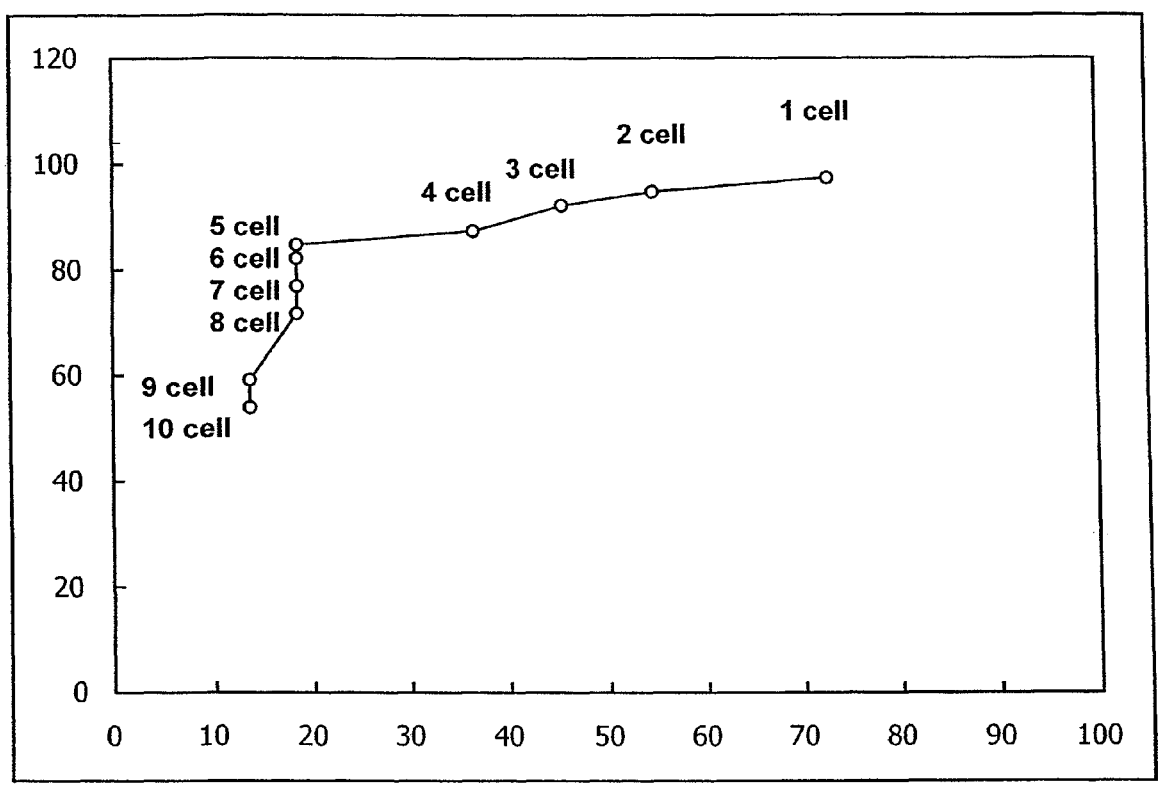
FIG. 1 depicts a receiver operator characteristic (ROC) curve derived from FISH analysis of specimens from cancer positive and cancer negative patients. Sensitivity (y axis) and specificity (x axis; 1-specificity) are depicted for cutoff values ranging from 1 to 10 cells per specimen.

The invention includes probe sets and methods of using probes and probe sets for the detection of lung cancer. The probes and methods described herein allow for the rapid and sensitive detection of lung cancer in a biological sample such as a bronchial specimen, a lung biopsy, or a sputum sample. In addition, the invention includes methods of selecting probe sets for the detection of cancer.

Chromosomal Probes

Suitable probes for in situ hybridization in accordance with the invention fall into three broad groups: chromosome enumeration probes, which hybridize to a chromosomal region and indicate the presence or absence of a chromosome; chromosome arm probes, which hybridize to a chromosomal region and indicate the presence or absence of an arm of a chromosome; and locus specific probes, which hybridize to a specific locus on a chromosome and detect the presence or absence of a specific locus. Chromosomal probes and combinations thereof are chosen for sensitivity and/or specificity when used in methods for the detection of lung cancer. Probe sets can include any number of probes, e.g., at least 2, 3, 4, 5, 6, 7, 8, 9, 10, 15, or 20 probes.

A chromosome enumeration probe can hybridize to a repetitive sequence, located either near or removed from a centromere, or can hybridize to a unique sequence located at any position on a chromosome. For example, a chromosome enumeration probe can hybridize with repetitive DNA associated with the centromere of a chromosome. Centromeres of primate chromosomes contain a complex family of long tandem repeats of DNA, composed of a monomer repeat length of about 171 base pairs, that are referred to as alpha-satellite DNA. Non-limiting examples of chromosome enumeration probes include probes to chromosomes 1, 3, 4, 6, 7, 8, 9, 10, 11, 12, 16, 17, and 18. Examples of several specific chromosome enumeration probes and their respective target regions are described in Table 1 of Example 1.

A chromosome arm probe can hybridize to a repetitive or unique sequence located on an arm, either the short or long arm, of a given chromosome. The gain or loss of the sequence to which the chromosome arm probe hybridizes can be used to indicate the gain or loss of the arm. Non-limiting examples of chromosome arm probes include probes to chromosome arms 3q, 5p, 7p, 3p, and 20q. Examples of specific chromosome arm probes and their respective target regions are described in Table 1.

A locus specific probe hybridizes to a specific, non-repetitive locus on a chromosome. Non-limiting examples of locus specific probes include probes to the following loci: 3p14; 3q26; 5p15; 5q31; 7p12; 8q24; 9p21; 10q23; 13q14; 17p13; 17q21; 20q13; and 21q22. Some of these loci comprise genes, e.g., oncgogenes and tumor suppressor genes, that are altered in some forms of cancer. Thus, probes that target these genes, either exons, introns, or regulatory sequences of the genes, can be used in the detection methods described herein. Examples of target genes include: FHIT (3p14); EGR1 (5q31); EGFR1 (7p12); c-MYC (8q24); PTEN (10q23); RB (13q14); P53 (17p13); and HER-2/neu (17q21).

Chromosomal probes can be of any size, but are typically about 50 to about $5 \times 10^5$ nucleotides in length. Chromosomal probes can comprise repeated sequences, e.g., fragments of about 100 to about 500 nucleotides in length. Probes that hybridize with centromeric DNA and specific chromosomal loci are available commercially, for example, from Vysis, Inc. (Downers Grove, Ill.), Molecular Probes, Inc. (Eugene, Oreg.), or from Cytocell (Oxfordshire, UK). Alternatively, probes can be made non-commercially from chromosomal or genomic DNA through standard techniques. For example, sources of DNA that can be used include genomic DNA, cloned DNA sequences such as a bacterial artificial chromosome (BAC), somatic cell hybrids that contain one, or a part of one, human chromosome along with the normal chromosome complement of the host, and chromosomes purified by flow cytometry or microdissection. The region of interest, e.g., a target region indicated in Table 1, can be isolated through cloning, or by site-specific amplification via the polymerase chain reaction (PCR). See, for example, Nath and Johnson, *Biotechnic Histochem.*, 1998, 73(1):6-22; Wheeless et al., *Cytometry*, 1994, 17:319-326; and U.S. Pat. No. 5,491, 224.

Chromosomal probes can contain a detection moiety that facilitates the detection of the probe when hybridized to a chromosome. Examples of detection moieties include both direct and indirect labels, as described below.

Chromosomal probes can be directly labeled with a detectable label. Examples of detectable labels include fluorophores, organic molecules that fluoresce after absorbing light of lower wavelength/higher energy, and radioactive isotopes, e.g., $^{32}$P and $^{3}$H. A fluorophore can allow a probe to be visualized without a secondary detection molecule. For example, after covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, U.S. Pat. No. 5,491,224.

Examples of fluorophores that can be used in the methods described herein are as follows: 7-amino-4-methylcoumarin-3-acetic acid (AMCA), Texas Red™ (Molecular Probes, Inc., Eugene, Oreg.); 5-(and-6)-carboxy-X-rhodamine, lissamine rhodamine B, 5-(and-6)-carboxyfluorescein; fluorescein-5-isothiocyanate (FITC); 7-diethylaminocoumarin-3-carboxylic acid, tetramethylrhodamine-5-(and-6)-isothiocyanate; 5-(and-6)-carboxytetramethylrhodamine; 7-hydroxycoumarin-3-carboxylic acid; 6-[fluorescein 5-(and-6)-carboxamido]hexanoic acid; N-(4,4-difluoro-5,7-dimethyl-4-bora-3a,4a diaza-3-indacenepropionic acid; eosin-5-isothiocyanate; erythrosin-5-isothiocyanate; and Cascade™ blue acetylazide (Molecular Probes, Inc., Eugene, Oreg.).

In methods using multiple probes, fluorophores of different colors can be chosen such that each chromosomal probe in the set can be distinctly visualized. Alternatively, two or more probes in a set can be labeled with the same or a similar fluorophore. Probes can be viewed with a fluorescence microscope and an appropriate filter for each fluorophore, or by using dual or triple band-pass filter sets to observe multiple fluorophores. See, for example, U.S. Pat. No. 5,776,688. Alternatively, techniques such as flow cytometry can be used to examine the hybridization pattern of the chromosomal probes.

Probes also can be indirectly labeled, e.g., with biotin or digoxygenin, although secondary detection molecules or further processing is required to visualize the labeled probes. For example, a probe labeled with biotin can be detected by avidin conjugated to a detectable marker, e.g., a fluorophore. Additionally, avidin can be conjugated to an enzymatic marker such as alkaline phosphatase or horseradish peroxidase. The enzymatic markers can be detected in standard colorimetric reactions using a substrate for the enzyme. Substrates for alkaline phosphatase include 5-bromo-4-chloro-3-indolylphosphate and nitro blue tetrazolium. Diaminobenzoate can be used as a substrate for horseradish peroxidase.

In Situ Hybridization

The presence or absence of cells with chromosomal aberrations is determined by in situ hybridization. Cells with chromosomal aberrations have, for example, an abnormal number of chromosomes and/or have chromosomal structural alterations such as the gain or loss (e.g., hemizygous or homozygous loss) of a specific chromosomal region, such as a locus or a chromosomal arm as indicated in Table 1. For example, a cell having one or more chromosomal gains, e.g., three or more copies of any given chromosome, can be considered to test positive in the methods described herein. Cells exhibiting monosomy and nullisomy may also be considered test positive under certain circumstances. In general, in situ hybridization includes the steps of fixing a biological sample, hybridizing a chromosomal probe to target DNA contained within the fixed biological sample, washing to remove non-specific binding, and detecting the hybridized probe.

A "biological sample" is a sample that contains cells or cellular material, e.g., cells or cellular material derived from pulmonary structures, including but not limited to lung parenchyme, bronchioles, bronchial, bronchi, and trachae. Non-limiting examples of biological samples useful for the detection of lung cancer include bronchial specimens, lung biopsies, and sputum samples. Examples of bronchial specimens include bronchial secretions, washings, lavage, aspirations, and brushings. Lung biopsies can be obtained by methods including surgery, bronchoscopy, and transthoracic needle biopsy. In one example, touch preparations can be made from lung biopsies.

In addition, biological samples can include effusions, e.g., pleural effusions, pericardial effusions, or peritoneal effusions. In addition, biological samples can include cells or cellular material derived from tissues to which lung cancers commonly metastasize. These tissues include, for example, lymph nodes, blood, brain, bones, liver, and adrenal glands. Thus, the probes and probes sets described herein can be used to detect lung cancer and lung cancer metastasis.

Typically, cells are harvested from a biological sample and prepared using techniques well known to those of skill in the art. For example, cells can be harvested by centrifuging a biological sample, such as a bronchial washing, and resuspending the pelleted cells. Typically, the cells are resuspended in phosphate-buffered saline (PBS). After centrifuging the cell suspension to obtain a cell pellet, the cells can be fixed, for example, in acid alcohol solutions, acid acetone solutions, or aldehydes such as formaldehyde, paraformaldehyde, and glutaraldehyde. For example, a fixative containing methanol and glacial acetic acid in a 3:1 ratio, respectively, can be used as a fixative. A neutral buffered formalin solution also can be used, and includes approximately 1% to 10% of 37-40% formaldehyde in an aqueous solution of sodium phosphate. Slides containing the cells can be prepared by removing a majority of the fixative, leaving the concentrated cells suspended in only a portion of the solution. The cell suspension is applied to slides such that the cells do not overlap on the slide. Cell density can be measured by a light or phase contrast microscope.

Prior to in situ hybridization, chromosomal probes and chromosomal DNA contained within the cell each are denatured. If the chromosomal probes are prepared as a single-stranded nucleic acid, then denaturation of the probe is not be required. Denaturation typically is performed by incubating in the presence of high pH, heat (e.g., temperatures from about 70° C. to about 95° C.), organic solvents such as formamide and tetraalkylammonium halides, or combinations thereof. For example, chromosomal DNA can be denatured by a combination of temperatures above 70° C. (e.g., about 73° C.) and a denaturation buffer containing 70% formamide and 2×SSC (0.3M sodium chloride and 0.03 M sodium citrate). Denaturation conditions typically are established such that cell morphology is preserved. For example, chromosomal probes can be denatured by heat, e.g., by heating the probes to about 73° C. for about five minutes.

After removal of denaturing chemicals or conditions, probes are annealed to the chromosomal DNA under hybridizing conditions. "Hybridizing conditions" are conditions that facilitate annealing between a probe and target chromosomal DNA. Hybridization conditions vary, depending on the concentrations, base compositions, complexities, and lengths of the probes, as well as salt concentrations, temperatures, and length of incubation. For example, in situ hybridizations are typically performed in hybridization buffer containing 1-2×SSC, 50-55% formamide, a hybridization acceleratant (e.g. 10% dextran sulfate), and blocking DNA to suppress non-specific hybridization. In general, hybridization conditions, as described above, include temperatures of about 25° C. to about 55° C., and incubation lengths of about 0.5 hours to about 96 hours. More particularly, hybridization can be performed at about 32° C. to about 45° C. for about 2 to about 16 hours.

Non-specific binding of chromosomal probes to DNA outside of the target region can be removed by a series of washes. Temperature and concentration of salt in each wash depend on the desired stringency. For example, for high stringency conditions, washes can be carried out at about 65° C. to about 80° C., using 0.2× to about 2×SSC, and about 0.1% to about 1% of a non-ionic detergent such as Nonidet P-40 (NP40). Stringency can be lowered by decreasing the temperature of the washes or by increasing the concentration of salt in the washes.

Detection of Chromosomal Abnormalities

Gain or loss of chromosomes or chromosomal regions within a cell is assessed by examining the hybridization pattern of the chromosomal probe or set of chromosomal probes (e.g., the number of signals for each probe) in the cell, and recording the number of signals. In a typical assay, the hybridization pattern is assessed in a plurality of cells, e.g., about 25-5,000 cells.

Samples containing a plurality of cells, e.g., at least about 100, of which 1 or more, e.g., at least about 5, 6, 7, 8, 9, 10, 15, or 20, cells "test positive" typically are considered cancer positive. By "test positive" is meant possessing the gain or loss of a chromosome, chromosomal arm, or locus as described herein. Criteria for "test positive" can include testing positive with one, two, three, four or more probes. In addition, "test positive" can include performing a hybridization analysis with multiple probes, e.g. four probes, and detecting abnormal hybridization patterns with a subset of the probes, e.g., at least two or three probes.

A sample containing cells, e.g. cells placed on a flat surface such as a slide, can be evaluated by a variety of methods and using a variety of criteria. The probes and methods described herein are not limited to usage with a particular screening methodology. For example, in what is known as the "scanning method," the observer scans hundreds to thousands of cells for cytologic abnormalities (as viewed with a DAPI filter). The number of cells assessed depends on the cellularity of the specimen, which varies from patient to patient. Cytologic abnormalities commonly but not invariably associated with neoplastic cells include nuclear enlargement, nuclear irregularity, and abnormal DAPI staining (frequently mottled and lighter). In the scanning method, the observer primarily focuses the evaluation of the cells for chromosomal abnormalities (as demonstrated by FISH) on those cells that also exhibit cytologic abnormalities. In addition, a proportion of the cells that do not have obvious cytologic abnormalities can be evaluated, since chromosomal abnormalities occur in the absence of cytologic abnormalities. The scanning method is described in further detail in U.S. Pat. No. 6,174,681, the content of which is incorporated by reference.

Screening, Monitoring, and Diagnosis of Patients for Lung Cancer

The methods described herein can be used to screen individuals for lung cancer or to monitor patients diagnosed with lung cancer. For example, in a screening mode, individuals at risk for lung cancer, such as individuals who smoke or have been chronically exposed to smoke, or individuals chronically exposed to asbestos, are screened with the goal of earlier detection of lung cancer. In addition, the probes and methods described herein can be used for the diagnosis of symptomatic patients. The methods described herein can be used alone, or in conjunction with other tests. For example, a patient having an increased risk of lung cancer can be screened for lung cancer by performing in situ hybridization as described herein together with other standard tests such as imaging analysis, e.g., CT, spiral CT, and X-ray analysis, and/or cytology. Alternatively, standard methods can be performed first on a patient, and if the standard test gives equivocal or negative results, then a method described herein can be performed.

The methods described herein can also be used to select a therapy for a patient diagnosed as having lung cancer. The methods can thus simultaneously diagnose a lung cancer and provide useful information as to possible treatments for the cancer. Several of the probes described herein are directed to oncogenes and tumor suppressor genes. If one or more of these genes is found to be altered in the course of a determination that the patient has cancer, then this information can be used to select a therapy, e.g., a therapy that modulates (increases or decreases) the presence or activity of these genes and/or their protein products. For example, if an alteration of the 17q21 locus is discovered, then this information could be used to design a Her-2-based therapy (see, e.g., Cragg et al., Curr. Opin. Immunol., 1999, 11:541-547). The loci containing specific oncogenes and tumor suppressor genes are indicated in Table 1.

Probe Selection Methods

The selection of individual probes and probe sets can be performed using the principles described in the examples. These selection methods make use of discriminate and/or combinatorial analysis to select probes and probes sets that are useful for the detection of lung cancer with high sensitivity.

The methods described herein preferably have a combined sensitivity and specificity that is better than that of conventional methods, particularly for the early detection of lung cancer. As described in the examples, 26 chromosomal probes were hybridized to 27 different lung tumor specimens and 12 normal adjacent tissue specimens, and the extent of gain and loss of each target was measured. To analyze this data and select the most useful probe sets, several rules were developed that, when considered in combination, yield probe sets having a high sensitivity and specificity. Each rule is not hard-and-fast but states general preferences that are weighed against the other rules in order to arrive at optimally performing probe sets.

(1) Each probe selected for a probe set should have an ability on its own to discriminate between tumor and normal tissue. Probes with high discrimination abilities are preferred. The discrimination analysis utilizes two different approaches: (a) comparing the means and standard deviations between the tumor specimen set and normal adjacent tumor specimen set of the percentage of cells with target gain and loss for each of the probe targets, and (b) calculating the sensitivity and specificity of each probe individually for identifying the tumor and normal adjacent tumor specimens, for 1 various cutoff values of the cell percentages for targets gained and lost. Several different metrics can be generated to evaluate approach (a), which included calculation of D.V. (discriminate value), S (standard deviation at "midpoint"), and p-value. D.V. and p-value are generally accepted methods for evaluation. The relevance of S is that it is the cutoff value, as a multiple of the standard deviations from the tumor and normal means, at which the sensitivity would equal the specificity if the means and standard deviations actually equaled the true values of the two populations. For example, if the midpoint was one standard deviation of the tumor specimens from the mean of the tumor specimens, and one standard deviation of the normal adjacent specimens from the mean of the normal adjacent specimens, then the sensitivity and specificity would each equal 84% (this also assumes normal-error distributions for each population, which is less likely to be true for the normal adjacent tissue distributions due to their proximity to 0). The larger the S the greater the sensitivity and specificity of that probe.

(2) The primary metric for combined sensitivity and specificity will be the quantity called 'vector' which is the magnitude of the vector drawn between the points on a sensitivity versus specificity plot representing the ideal (sensitivity specificity=1) and the measured sensitivity and specificity. Therefore the vector value ranges from 0 for the ideal case and 1.414 for the worst case.

(3) Each probe selected for a probe set should complement the other selected probes, that is, it should identify additional tumor specimens that the other probe(s) failed to identify. One method of identifying the best complementing set of probes is to take the probe with the lowest vector value, remove the group of tumor specimens it identified from the full set of tumor specimens, and then determine the probe with lowest vector value on the remaining tumor specimens. This process can be continued as necessary to complete the probe set. The approach selected here of generating all possible probe combinations, and calculating the sensitivity and specificity of each, predicts the performance of all possible probe sets and allows selection of the minimal probe set with the highest performance characteristics. Also, a variety of combinations with similarly high performance characteristics is obtained. Considering the possible errors due to the finite number of specimens tested, several of the high ranking probe combinations can be compared based on other practical characteristics such as relevance to disease prognosis or difficulty in making the probe.

(4) The ability of probes to complement one another is more important than the discriminating ability of individual probes, except as indicated in (5) below.

(5) Regardless of the measured ability to complement other probes, each probe must identify a statistically different percentage of test positive cells between the tumor and normal adjacent tissue specimen sets. If this condition is not met then a probe might be selected erroneously based on apparent complementation.

(6) Data for combinations of two probes is more reliable than data for combinations of three probes, and data for combinations of three probes is more reliable than data for combinations of four probes. This results from the reduced ability to make correlations between greater numbers of probes with the finite number of specimens tested.

(7) The dependence of probe and probe combination performance as a function of cutoff value must be considered. "Cutoff value" refers to the percentage of cells in a population that must have gains or losses for the sample to be considered positive. A sample is therefore called as positive or negative depending upon whether the percentage of cells in the sample is above the cutoff value or equal to or less than the cutoff value.

In general, the combined specificity and sensitivity of probes is better at low cutoff values. However, when the cancer cells are distributed within a matrix containing many normal cells, such as bronchial secretions or sputum, probes performing best at high cutoffs are more likely to be detected. This is because good performance at high cutoffs indicates a higher prevalence of cells containing the abnormality. Examples of cutoff values that can be used in the calculations include about 5%, 10%, 15%, 20%, 25%, 30%, 35%, 40%, 45%, 50%, and 60%.

(8) The measurement of target gain is favored over measurement of target loss. Overlapping targets or poor hybridization to some cells can falsely suggest monosomy. Locus-specific or chromosomal arm probes designed to detect deletions are generally smaller than locus-specific or chromosomal arm probes designed to detect gain since the deletion probes must not extend beyond the minimally deleted region. If too much of the "deletion probe" extends beyond the deleted sequence, enough signal may remain to be falsely counted. Since "deletion probes" are usually kept small the signals are not as intense as signals for targets typically gained. This in turn makes it more likely that real signals from targets being monitored for deletion may be miscounted. Likewise, repetitive sequence probes, like some chromosome enumeration probes used here are preferable to single locus probes because they usually provide brighter signals and hybridize faster than locus specific probe. On the other hand, repetitive sequence probes are more sensitive to polymorphisms than locus specific probes.

(9) A probe or combination of probes preferably shows an improvement over conventional methods such as cytology. A probe or probe combination preferably detects lung cancer with a sensitivity of at least about 50%, 60%, 65%, 70%, 75%, 80%, 85%, 90%, 95%, or even 100%. A probe or probe combination preferably detects lung cancer with a vector value of less than about 0.500, 0.450, 0.400, 0.350, 0.300, 0.250, 0.200, 0.150, or 0.100.

The invention will be further described in the following examples, which do not limit the scope of the invention described in the claims.

EXAMPLES

Example 1

Probe Selection

A collection of 26 probes was assembled as candidates for detecting chromosomal abnormalities in lung cancer by in situ hybridization. The probes were hybridized to a collection of lung tumor touch preparations, and the distribution of the copy number per cell of each probe target was determined. In order to conserve tumor specimens, multi-color hybridizations were utilized to limit the number of hybridization regions per specimen to 8. To achieve this, the 26 probes were labeled with several different fluorophores. Mixtures of 3 or 4 probes each were prepared from the labeled probes forming the 8 probe sets. Where possible, chromosome enumeration probes and locus specific probes that target the same chromosome were combined in the same set to distinguish whole chromosome aneuploidy from gains and losses of regions within a chromosome.

The 26 probes selected for hybridization to lung touch preparations are described in Table 1. The probes included 13 chromosome enumeration probes (CEP™ probes from Vysis, Inc.; targeting repetitive centromeric sequences) and 13 locus specific probes (LSI™ from Vysis, Inc. or BAC preparations; targeting unique sequences associated with amplified or deleted chromosomal regions). Column 3 of Table 1 describes the target location of each of the 26 probes. For several of the probes, oncogenes or tumor suppressor genes that are located at the relevant locus are also listed.

Mixtures of 3 probes, labeled with SpectrumAqua™, SpectrumGreen, and SpectrumOrange™, or 4 probes, labeled with SpectrumAqua™, SpectrumGreen™, SpectrumGold™, and SpectrumRed™, were prepared to form the 8 probe sets. The fluorescent label used for each probe and the probe set containing each probe are described in columns 4 and 5, respectively, of Table 1.

Tumor touch preparations, prepared from lung tumors removed from 27 patients with a range of lung cancers, were used for testing the 26 probes. In addition, specimens prepared from normal lung tissue generally at some distance from the tumors (NAL=normal adjacent lung tissue) from twelve of the same patients were also tested in order to examine the background levels of gained and lost targets for each probe. The characteristics of the lung tumor and normal specimens are listed in Table 2. Touch preparations were prepared by pressing a piece of lung tumor or normal adjacent tissue against a glass microscope slide and fixing briefly in ethanol. The specimens were then stored at −20° C. until ready for use.

Prior to in situ hybridization, the touch preparations were treated to improve in situ hybridization performance by the following protocol.

(1) Fix the specimen slide in a fresh Carnoy's solution (3:1 methanol:acetic acid) for 20 minutes at room temperature. Allow the slide to dry in the air.

(2) Place the slide on a 45° C. hot plate for 15 minutes.

(3) Incubate the slide in 2×SSC at 37° C. for 10 minutes.

(4) Place the slide in a pepsin solution (0.05 mg pepsin per ml 10 mM HCl) at 37° C. for 13 minutes. The pepsin solution is prepared fresh each day by diluting 25 μL of a pepsin stock solution (100 mg pepsin/mL water; use 2,500-3,000 U/mg pepsin) into 50 mL of 10 mM HCl.

(5) Place the slide in 1×PBS for 5 minutes at room temperature.

(6) Fix the slide in 1% formaldehyde for 5 minutes at room temperature. The formaldehyde solution is prepared by mixing 1.35 mL of 37% formaldehyde with 48.15 mL of 1×PBS and 0.5 mL of 2 M $MgCl_2$. Discard after each day of use.

(7) Place the slide in 1×PBS for 5 minutes at room temperature.

(8) Dehydrate the specimen by placing the slide in a series of ethanol solutions (70%, 85%, 100%), 1-5 minutes per solution. Allow the specimen to dry in the air before denaturing.

After performing the above treatments, fluorescence in situ hybridization was performed on all specimens as follows.

(1) Denature the specimen's DNA by placing the slide in a solution of 70% formamide/2×SSC at 73° C. for 5 minutes.

(2) Dehydrate the specimen by placing the slide in a series of ethanol solutions (70%, 85%, 100%), 1-5 minutes per solution. Allow the specimen to air dry before applying denatured probe.

(3) Denature a probe solution by placing a tube containing the probe in a 73° C. water bath for 5 minutes.

(4) Apply the denatured probe solution to the denatured slide, place a coverslip over the solution, and seal the coverslip by applying rubber cement along the edges. Allow the probe to hybridize overnight at 37° C. in humidified chamber.

(5) Wash the slide in a Coplin jar in 0.4×SSC/0.3% NP-40 for 3 minutes at 70° C. (or 1 minute at 73° C.). Wash 4 slides simultaneously per Coplin jar.

(6) Soak the slide in 2×SSC/0.1% NP-40, for several seconds to several minutes.

(7) Apply antifade/counterstain solution and cover with a coverslip. Store the slides at −20° C. until analyzed.

Hybridized specimen slides were viewed on a fluorescence microscope using single bandpass filter sets specific for each of the 4 fluorescent labels and the DAPI counterstain. Each touch preparation was analyzed by counting the number of spots of each fluorescent color in 100 consecutive non-inflammatory cells and the copy number of each probe target recorded. Several of the specimens did not hybridize well with all 26 probes, so the number of specimens tested differs for each probe. In addition, probe set 8 was not tested on all specimens.

Example 2

Analysis of In Situ Hybridization Data

The target copy number data for each of the normal and tumor specimens was analyzed for the ability of each probe to discriminate between tumor and normal specimens (discriminate analysis) and for the ability of probe combinations to discriminate between tumor and normal specimens (combinatorial analysis). These analyses were used as part of the data considered in deciding which probes should be used individually or in concert to best identify lung cancer cells.

Discriminate Analysis

The ability of individual probes to discriminate between the normal specimen group and the tumor specimen group was evaluated first by comparing the averages and standard deviations of the percentages of abnormal cells found in each group. These data are listed in Tables 3 (normal specimen group) and 4 (tumor specimen group). The first 26 rows in each table lists data derived from absolute target counts per cell, for each of the 26 probes tested. For these calculations, individual targets present in greater than 2 copies were considered an abnormal gain in copy number, and targets present in less than 2 copies were considered an abnormal loss in copy number. The last 8 rows in Tables 3 and 4 list data derived from ratios of LSI/CEP target numbers, or in the case of chromosome 5, the ratio of LSI 5p15/LSI 5q31 target numbers. Ratios were only calculated when both probes were contained in the same probe set. The ratios were calculated on a cell-by-cell basis. For the purpose of these calculations, cells were considered to have target gain when ratios were greater than 1, and target loss when ratios were less than 1.

In Tables 3 and 4, the columns headed 'Ave. % cells . . . ' are the averages of the percentage of cells found in each specimen with either target copy number gain or target copy number loss, as indicated in the heading. The columns headed 'S % cells . . . ' are the standard deviations of the average cell percentages for the number of specimens ('Number of specimens . . . ' columns) in which interpretable hybridizations for each specific probe were obtained.

Included in Table 4 are three columns containing different measures of the ability of each probe to discriminate between the tumor and normal specimen groups. The discriminate value, D.V., is calculated according to Equation 1:

$$DV=(M_T-M_N)^2/(SD_T^2+SD_N^2) \quad (1)$$

with values being larger for greater separation between the mean of the normal specimens, $M_N$, and the mean of the tumor specimens, $M_T$, and for smaller standard deviations of the normal, $S_N$, and tumor, $S_T$, specimens.

The 'SD's at midpoint', S is calculated by Equation 2:

$$S.D.M.=(M_T-M_N)/(SD_T+SD_N) \quad (2)$$

and is the number of standard deviations from the tumor and normal group means which equal the separation of the means. If the means and standard deviations were the true values for the tumor and normal populations, then S is the point at which the sensitivity and specificity are equal to each other. The larger the S, the greater the value of the sensitivity and specificity.

The third measure of discrimination listed in Table 4 is the probability, p, that the measured means are from the same population. The value of p is determined from the Student's t-test. In effect the smaller the p value, the more statistically different the tumor population is from the normal population. A p<0.05 is typically considered to represent a statistically significant difference between the two groups.

The p values in Table 4 indicate that all of the 26 probes found statistically significant (p<0.05) gains for the tumor specimen group relative to the normal group, when using the absolute target numbers. When viewed as ratios between LSI and corresponding CEP or LSI target numbers, 5 of the 8 ratios showed significant differences (last 8 rows in Table 4). By contrast, only 2 of the 26 probes found statistically significant loss of absolute target numbers (LSI 8p24 and CEP 17), while 5 of the 8 ratios showed significant differences.

The rows of Table 4 are sorted from highest to lowest D.V. for gain of targets. The data derived from absolute target counts is sorted separately from the ratio data. Examination of the D.V., S, and p values for target gain shows relatively good correspondence between the three discrimination parameters. The top 5 discriminating probes selected by all three parameters are the same, LSI 5p15, LSI 7p12, CEP 1, CEP 6, and LSI 8q24, in descending order (all indicating gain of targets in tumor specimens).

Another approach within the overall selection method for determining which probes provide the best discrimination between normal and tumor specimens is to look at the number of specimens correctly identified by each probe. This requires selecting a cutoff number for the percentage of cells with gains or losses. A sample is then called positive or negative for cancer depending upon whether the percentage of cells in the sample is above the cutoff value or equal to or less than the cutoff value, respectively. The accuracies of identifying the positive samples (sensitivity) and negative samples (specificity) are then used to select the best probes.

Table 5 lists the specificity and sensitivity of gain and loss of all 26 probe targets and the same CEP/LSI and 5p/q ratios listed in Tables 3 and 4. The table includes the specificity and sensitivity values at 6 different cutoff values (5%, 10%, 20%, 30%, 400%, and 50%). The table also includes two measures of the combined specificity and sensitivity, since the overall ability to discriminate between tumor and normal specimens depends on both specificity and sensitivity. The first combined attribute is the product of specificity and sensitivity. The product is largest if both specificity and sensitivity are high, and is reduced if either or both are low. The other combined attribute, designated as "vector," is calculated according to Equation 3:

$$\text{Vector} = [(1-\text{specificity})^2 + (1-\text{sensitivity})^2]^{0.5} \quad (3)$$

This attribute has a value of 0 when specificity and sensitivity 1, and increases to 1.414 as both approach 0.

The rows in Table 5 are sorted by increasing vector value for each cutoff value. The data derived from absolute target counts is sorted separately from the ratio data. Target gains dominate the top of the table and the same probes tend to show the lowest vector values, although their relative order changes with cutoff value. Probes showing consistently high discrimination ability based on the vector value and absolute target counts include LSI 8q24, LSI 5p15, LSI 7p12, LSI 3q26, LSI 20q13, LSI 5q31, LSI 3p14, LSI 17q21, CEP 1, CEP 4, CEP 6, CEP 7, CEP 9, and CEP 16. Each of these probes is found in the top 10 rows for at least two of the cutoff values. The target ratios generally showed lower vector values except for the chromosome 5p51/5q31 ratio which had vector values comparable to some of the best probes based on their absolute target counts.

Combinatorial Analysis

The ability of multiple probes used in concert to increase assay sensitivity (complementation) was investigated using combinatorial analysis. The analysis was initiated by generating all possible combinations of a group of probes. The counting data from each specimen was then examined to determine if any of the probes in each combination identified gain or loss of their target above a threshold number of cells. If any of the probes in a combination were positive, then the specimen was considered positive for cancer for that combination.

The combinations were kept to a maximum of four probes. The entire set of 26 probes was not used to generate all combinations due to the large number of possible combinations that would be generated for the 26 probes and their relevant ratios, each of which would be examined for gain and loss (866,847 possible combinations of 1, 2, 3, and 4 probes). Instead, the set of probes and ratios was reduced to include only those probes that identified gains, and those probes that identified losses with p<0.01 (Table 4). This provided some assurance that probe combinations would not be over rated as a result of randomly high target counts of individual probes. To further reduce complexity, two different groups of probes were examined separately. Group 1 included all of the probes for which the absolute counts identified target gain or loss with p<0.01. Group 2 replaced the members of Group 1 with their corresponding LSI/CEP or LSI/LSI ratio, if the ratio identified target gain or loss with p<0.01. Therefore, Group 1 consisted of all of the probes for gain listed in the first 25 rows of Table 4 (because of its high significance, LSI 5p15/LSI 5q31 was also included in this group) and none of the probes for losses. Group 2: replaced LSI 7p12 and LSI 8q24 with LSI 7p12/CEP 7 and LSI 8q24/CEP 8, respectively, for gains; deleted the other LSI probes that had corresponding LSI/CEP ratios with p>0.01; and added LSI 9p21/CEP 9 and LSI 17p13/CEP 17 for loss.

Tables 6 through 9 list the combinations of 2, 3, and 4 probes with the combined highest sensitivities and specificities, for cutoff values of 10% (Table 6), 20% (Table 7), 30% (Table 8), and 40% (Table 9), respectively. The measure of combined sensitivity and specificity used to order the combinations was the vector value. A particular combination was excluded from the tables if a subset of probes in the combination gave an equal or lower vector value. The probes contributing to the best combinations changed as the cutoff value was increased. The best vector values also increased as the cutoff was increased, as seen previously in Table 5 for single probes. In determining the number of probes in a combination, ratios were counted as two probes, unless one of the probes in the ratio was also in the combination. In general, ratios were not found in the better scoring combinations, except for the LSI 5p15/LSI 5q31 ratio. Also, target loss rarely ranked in the top performing probe combinations. As a result, in further discussion the gain of a target is implied, unless specifically denoted as a loss.

At a percent cell cutoff value of 10% (Table 6), LSI 8q24 and LSI 5p15 were commonly found in the top performing combinations of two probes, and complemented each other as well. LSI 8q24 was also complemented well by LSI 17q21, LSI 5q31, LSI 9p21, CEP 1, CEP 6, CEP 7, CEP 9, CEP 11, and CEP 17. LSI 5p15 was also complemented well by LSI 17q21, LSI 5q31, LSI 9p21, LSI 13q14, CEP 8, CEP 12, and CEP 17.

In addition, LSI 7p12 and CEP 1 complemented one another well. The same probes were also found in the better combinations of three and four probes.

When the cutoff was increased to 20% (Table 7), LSI 5p15 remained in the top combinations of two, and was complemented best by LSI 3q26, CEP 16, LSI 20q13, LSI 17q21 and CEP 4. LSI 8q24, LSI 3p14, LSI 5q31, LSI 7p12, CEP 3, CEP 6, and CEP 9 also provided good complementation to LSI 5p15. LSI 8q24 fell lower in the list, although still a good performer, being complemented by LSI 7p12 and CEP 6. The better combinations of three and four probes also included these probes as well as other probes identified above in the better combinations at the cutoff of 10.

As the cutoff was increased to 30% (Table 8), LSI 5p15 persisted in the better combinations, and LSI 8q24 was absent from the higher-ranking combinations. Complementation of LSI 5p15 was provided by CEP 6, CEP 16, LSI 20q13, LSI 3q26, LSI 17q21, LSI 7p12, and LSI 3p14. Also, LSI 7p12 was complemented by CEP 6, and CEP 6 and CEP 7 complemented one another. Detection of target loss was only found to be important in combinations of four probes (LSI 17p13 loss relative to CEP 7).

Increasing the cutoff value to 40% (Table 9) reduced the importance of LSI 5p15 in two probe combinations, and placed LSI 7p12 at the top of the list, which was complemented best by LSI 3q26 and CEP 6, and also by CEP 18, CEP 4, CEP 16, LSI 20q13 and LSI 5p15. CEP 6 ranked high when complemented by either CEP 1 or CEP 7. Other high ranking pairs of probes included LSI 3q26 with either LSI 5p15, CEP1, or CEP 7. In combinations of three probes, the combination of LSI 7p12 and CEP 6 with CEP 11 was at the top of the list, just ahead of combinations of CEP 6 with either CEP 1 or CEP 7, also complemented by CEP 11. Other probes included in the better performing combinations of three were 17q21, LSI 3q26 CEP 4, CEP 16, CEP 18, and LSI 20q. In combinations of four probes, CEP 6 combined with either CEP 1 or CEP 7 was at the top of the list when complemented by 17p13/CEP 16 loss. Another loss, 9p21/CEP 9 was next when combined with CEP 7 and LSI 3q. Other high ranking combinations of four included LSI 7p12, LSI 10q23, CEP 10, CEP 11, LSI 5p15, LSI 5q31, LSI 5p/LSI 5q, CEP 6, CEP 7, and CEP 9.

Example 3

Selection of Probe Sets

Table 13 lists probes and probe sets selected by analyzing the data from the discriminate and combinatorial analyses and applying the probe selection criteria described herein. The probe sets of Table 13 range in size from a single probe to 4 probes. Assays using additional probes, e.g., more than four, and additional fluorescent labels can be performed.

The single probes listed in Table 13 are the probes that individually showed improvement over cytology. These include LSI 5p15, LSI 7p12, LSI 8q24, CEP 1, CEP 6, and CEP 9. For each of these probes, the vector value was less than 0.400 for two of the cutoff values tested. Other probes described herein also gave vector values less than 0.400 for a single cutoff. However, good performance for two cutoff values implies that a probe is more robust.

Next, Table 13 lists 2-probe combinations. The probe pairs placed in this group were required to have a vector value less than 0.400 and rank in the top approximately 30 probe pairs (lowest vector values) for at least one cutoff value. The vector values are listed in the table for each probe pair for each cutoff value in which the probe pair was ranked in the top 30. Of special note are the probe pairs of LSI 5p15+LSI 8q24, LSI 5p15+CEP 12, and LSI 5p15+LSI 17q21 which have vector values less than 0.400 at 3 different cutoff values.

Next, Table 13 lists 3-probe combinations. Only a few combinations of 3 probes are listed under this heading since these are the few sets that improved over combinations of 2 probes for any particular cutoff value.

Next, Table 13 lists 4-probe combinations. Only one combination of 4 probes is listed under this heading since it was the only combination that improved over the combinations of 2 and 3 probes for any particular cutoff value.

To take advantage of the practical capability of using 3 and 4 FISH probes together, a strategy of redundancy can be introduced. Under this strategy, a third probe could be added to a pair of complementary probes if it also complemented one of the 2 probes. Alternatively, it might not complement either probe well, but instead it might be the next highest performing single probe. Similarly, 4 probe pairs could be generated by combining pairs of complementary probes. Some 3 and 4 probe sets generated using redundancy of the 2-probe sets listed in Table 13 are listed in a lower part of the same table. An alternative approach is to pick a 2-probe pair and add an additional 2 probes, one of which complements one member of the first pair, and the other of which complements the other member of the first pair. One benefit of redundancy probes is that assay specificity might be improved by requiring 2 of the targets to be gained in order to call the specimen abnormal. Redundancy can also improve sensitivity since if one probe hybridization should fail in an assay, the redundant probe might still detect the target gain. Other practical issues can be considered in probe selection. For example, the 4 probe set of LSI 5p15+LSI 8q24+LSI 7p12+LSI 17q21 can be constructed from probes in three of the top performing combinations of 2 probes listed in Table 13. The significance of this probe set is that it detects two loci of therapeutic importance, 17q21 containing the HER-2/neu gene and 7p12 containing the epidermal growth factor receptor gene (EGFR). The identification of abnormalities at these loci can be used to select an appropriate treatment regimen.

Example 4

Lung Cancer Detection

Two 3-color probe sets were chosen for preliminary testing on a series of bronchial secretion specimens. The results of this study showed that specificity and sensitivity equivalent to or better than conventional cytology could be obtained with multi-color FISH panels.

The results of the hybridizations of 3-color probe sets to each of 21 bronchial secretion smears are listed in Table 10, together with specimen identification numbers, clinical diagnoses, cytology results, and bronchoscopic biopsy results (two results when additional biopsy was performed). Each specimen was hybridized with two different 3-color probes sets. The first 3 color probe set contained LSI 8q24, LSI 5p15, and CEP 1, and the second set contained LSI 8q24, LSI 5p15, and CEP 6. Gain of the 5p15 target was found in 13 of the 13 FISH positive specimens. Gain of the 8q24, CEP1, and CEP 6 targets were found in 11, 7, and 5 of the 13 FISH positive targets, respectively. One of the specimen slides could not be evaluated by FISH due to poor morphology and no FISH abnormalities were found in the remaining 7 specimens. The performance of conventional cytology and FISH are compared to the clinical diagnosis in Tables 11 and 12, respectively. Clinical diagnosis was based on the combined information available to the clinician, and did not include the FISH result.

In the above methods, smears of bronchial secretions were prepared by placing a specimen between two microscope slides and sliding the slides apart from one another while applying slight pressure. The slides were then fixed briefly with ethanol and stored at −20° C. until ready for use.

Smears of bronchial secretions were prepared for in situ hybridization by the following protocol.

(8) Apply antifade/counterstain solution and cover with a coverslip. Store the slide at −20° C. until analyzed.

Bronchial secretion smears were analyzed by scanning the entire specimen. Each microscope field was viewed sequentially with the 4 single bandpass filter sets (DAPI

TABLE 1

Probes Used for Probe Selection

| PROBE NAME | DNA SOURCE | TARGET LOCATION | LABEL | PROBE SET |
|---|---|---|---|---|
| CEP 1, sat II/III | Vysis product | 1q12 | SpectrumGreen | 5 |
| CEP 3, alpha sat. | Vysis product | D3Z1, 3p11.1-q11.1 | SpectrumAqua | 6 |
| LSI 3p14/FHIT | BAC | 3p14 | SpectrumOrange | 6 |
| LSI 3q26/TERC | BAC | 3q26 | SpectrumGreen | 8 |
| CEP 4, alpha sat. | Vysis product | 4p11-q11 | SpectrumAqua | 8 |
| LSI D5S721, D5S23 | Vysis product | D5S721, D5S23, 5p15 | SpectrumGreen | 4 |
| LSI EGR1 | Vysis product | 5q31 | SpectrumOrange | 4 |
| CEP 6, alpha sat. | Vysis product | D6Z1, 6p11.1-q11 | SpectrumGreen | 6 |
| CEP 7, alpha sat. | Vysis product | D7Z1, 7p11.1-q11.1 | SpectrumAqua | 5 |
| LSI EGFR | BAC | 7p12 | SpectrumOrange | 5 |
| CEP 8, alpha sat. | Vysis product | D8Z2, 8p11.1-q11.1 | SpectrumAqua | 2 |
| LSI c-myc | Vysis product | 8q24 | SpectrumOrange | 2 |
| CEP 9, alpha sat. | Vysis product | 9p11-q11 | SpectrumGreen | 3 |
| LSI 9p21 | Vysis product | 9p21 | SpectrumGold | 3 |
| CEP 10, alpha sat. | Vysis product | 10p11.1-q11.1 | SpectrumGreen | 7 |
| LSI 10q23 (PTEN) | BAC | 10q23 | SpectrumOrange | 7 |
| CEP 11, alpha sat. | Vysis product | D11Z1, 11p11.1-q11 | SpectrumAqua | 3 |
| CEP 12, alpha sat. | Vysis product | D12Z3, 12p11.1-q11 | SpectrumAqua | 4 |
| LSI 13/RB1 retinoblastoma 1 | Vysis product | 13q14 | SpectrumGreen | 2 |
| CEP 16, sat. II | Vysis product | D16Z3, 16q11.2 | SpectrumGold | 8 |
| CEP 17, alpha sat. | Vysis product | D17Z1, 17p11.1-q11.1 | SpectrumAqua | 1 |
| LSI p53 | Vysis product | 17p13 | SpectrumOrange | 1 |
| LSI her2/neu (ERBB2) | Vysis product | 17q21 | SpectrumGreen | 1 |
| CEP 18, alpha sat. | Vysis product | D18Z1, 18p11.1-q11.1 | SpectrumAqua | 7 |
| LSI 20q13 (ZNF217) | Vysis product | 20q13 | SpectrumRed | 8 |
| LSI 21 | Vysis product | D21S259, D21S341, D21S342, 21q22 | SpectrumRed | 3 |

(1) Incubate the specimen slide in 2×SSC at 37° C. for 10 minutes.

(2) Place the slide in a pepsin solution (0.05 mg pepsin per mL 10 mM HCl) at 37° C. for 13 minutes.

(3) Place the slide in 1×PBS for 5 minutes at room temperature.

(4) Fix the specimen by placing the slides in 1% formaldehyde for 5 minutes at room temperature.

(5) Place the slides in 1×PBS for 5 minutes at room temperature.

In Situ Hybridization was Performed on the Specimens as Follows.

(1) Denature the specimen DNA by placing the slides in a solution of 70% formamide/2×SSC at 73° C. for 5 minutes.

(2) Dehydrate the specimen by placing the slide in a series of ethanol solutions (70%, 85%, 100%), 1-5 minutes per solution. Allow the specimen to air dry before applying denatured probe.

(3) Denature a probe solution by placing a tube containing the probe in a 73° C. water bath for 5 minutes.

(4) Apply the denatured probe solution to the denatured slide, place a coverslip over the solution, and seal the coverslip by applying rubber cement along the edges.

(5) Allow the probe to hybridize overnight at 37° C. in humidified chamber.

(6) Wash the slide in a Coplin jar in 0.4×SSC/0.3% NP-40 for 3 minutes at 70° C. (or 1 minute at 73° C.). Wash 4 slides simultaneously per Coplin jar.

(7) Soak the slide in 2×SSC/0.1% NP-40 for several seconds to several minutes.

TABLE 2

Lung Tumor and Normal Adjacent Tissue used for Probe Selection

| SPECIMEN NAM | SPECIMEN TYPE | TUMOR TYPE | TUMOR GRADE |
|---|---|---|---|
| T1 | tumor | bronchial alviolar carcinoma | 2 |
| T2 | tumor | adenocarcinoma | 2 |
| T3 | tumor | adenocarcinoma | 2 |
| T7 | tumor | adenocarcinoma | 4 |
| T8 | tumor | bronchial alviolar carcinoma | 1 |
| T9 | tumor | adenocarcinoma | 2 |
| T10 | tumor | adenocarcinoma | 3 |
| T11 | tumor | squamous cell carcinoma | 4 |
| T12 | tumor | adenocarcinoma | 3 |
| T13 | tumor | large cell carcinoma | 4 |
| T14 | tumor | adenocarcinoma | 4 |
| T15 | tumor | carcinoid tumor | ? |
| T16 | tumor | adenocarcinoma | 3 |
| T17 | tumor | adenocarcinoma | 2 |
| T18 | tumor | large cell carcinoma | 4 |
| T19 | tumor | adenocarcinoma | 4 |
| T20 | tumor | squamous cell carcinoma | 4 |
| T21 | tumor | squamous cell carcinoma | 4 |
| T22 | tumor | squamous cell carcinoma | 4 |
| T23 | tumor | adenocarcinoma | 3 |
| T24 | tumor | adenocarcinoma | 3 |
| T25 | tumor | squamous cell carcinoma | 4 |
| T26 | tumor | adenocarcinoma | 3 |
| T27 | tumor | adenocarcinoma | 2 |
| T28 | tumor | ? | ? |
| T31 | tumor | ? | ? |
| T32 | tumor | ? | ? |
| N1 | NAT | NA | NA |
| N2 | NAT | NA | NA |
| N3 | NAT | NA | NA |
| N7 | NAT | NA | NA |
| N8 | NAT | NA | NA |
| N12 | NAT | NA | NA |

TABLE 2-continued

Lung Tumor and Normal Adjacent Tissue used for Probe Selection

| SPECIMEN NAM | SPECIMEN TYPE | TUMOR TYPE | TUMOR GRADE |
|---|---|---|---|
| N13 | NAT | NA | NA |
| N14 | NAT | NA | NA |
| N15 | NAT | NA | NA |
| N16 | NAT | NA | NA |
| N17 | NAT | NA | NA |
| N18 | NAT | NA | NA |

*NAT = normal tissue adjacent to tumor tissue, NA = not applicable, ? = status unknown

TABLE 3

DISCRIMINATION ANALYSIS

| PROBE | Number of specimens | Ave. % cells with gain | S.D. % cells with gain | Ave. % cells with loss | S.D. % cells with loss |
|---|---|---|---|---|---|
| LSI 5p15 | 10 | 4.4000 | 2.8752 | 2.8000 | 1.9322 |
| LSI 7p12 | 10 | 5.5500 | 2.4771 | 1.3000 | 1.9465 |
| CEP 1 | 10 | 3.5500 | 0.8317 | 3.3000 | 2.5408 |
| CEP 6 | 10 | 1.9000 | 2.2336 | 4.8000 | 2.5734 |
| LSI 8q24 | 10 | 2.7500 | 1.9329 | 3.1000 | 1.8529 |
| LSI 20q | 10 | 3.9000 | 2.2336 | 4.5000 | 2.8771 |
| CEP 9 | 10 | 2.1000 | 2.0790 | 7.1000 | 5.0211 |
| LSI 3p14 | 10 | 4.3000 | 4.2439 | 2.9000 | 2.2828 |
| CEP 16 | 10 | 2.8000 | 1.4757 | 10.1000 | 4.6774 |
| CEP 4 | 10 | 2.8000 | 2.6162 | 2.6000 | 1.5055 |
| LSI 3q | 10 | 7.5000 | 3.2404 | 2.9000 | 3.0350 |
| CEP 7 | 10 | 1.4000 | 0.9661 | 2.4000 | 2.0111 |
| LSI 17q21 | 10 | 2.9000 | 2.4698 | 6.5000 | 2.8771 |
| LSI 5q31 | 10 | 3.4000 | 1.6465 | 4.4000 | 2.5033 |
| CEP 3 | 10 | 1.7000 | 1.4181 | 3.7000 | 2.2632 |
| CEP 10 | 10 | 1.4000 | 2.0656 | 4.1000 | 2.9981 |
| CEP 11 | 10 | 2.6500 | 2.3576 | 4.4000 | 1.7764 |
| CEP 8 | 10 | 1.0000 | 1.0541 | 4.5000 | 2.9907 |
| CEP 18 | 10 | 1.8000 | 1.9889 | 7.9000 | 3.8427 |
| LSI 13 | 10 | 2.4500 | 2.2417 | 3.6500 | 2.7894 |
| LSI 9p21 | 10 | 2.7500 | 2.8211 | 4.0000 | 3.0185 |
| LSI 10q23 | 10 | 6.0000 | 4.5947 | 3.0000 | 2.1602 |
| CEP 12 | 10 | 1.5000 | 1.2693 | 4.4000 | 2.6331 |
| CEP 17 | 10 | 2.3000 | 2.6687 | 10.9000 | 4.4585 |
| LSI 17p13 | 10 | 4.1000 | 3.9567 | 6.9000 | 3.2472 |
| LSI 21 | 10 | 7.8500 | 5.8407 | 6.1500 | 4.9668 |
| Ratios: | | | | | |
| 5 p/q imbal. | 10 | 5.2234 | 3.4875 | 3.2132 | 1.7602 |
| LSI 7p12/CEP 7 | 10 | 6.3000 | 3.6833 | 1.1500 | 2.1350 |
| LSI 8q24/CEP 8 | 10 | 6.1561 | 3.3667 | 2.9540 | 1.7098 |
| LSI 3p14/CEP 3 | 10 | 7.0000 | 4.9666 | 3.6000 | 2.6331 |
| LSI 17q21/CEP | 10 | 11.4000 | 5.4610 | 6.2000 | 2.1499 |
| LSI 10q23/CEP | 10 | 8.5000 | 5.9489 | 3.0000 | 1.6997 |
| LSI 9p21/CEP 9 | 10 | 7.7041 | 7.4657 | 3.9041 | 3.9546 |
| LSI 17p13/CEP | 10 | 11.3000 | 5.3759 | 6.0000 | 3.0551 |

TABLE 4

DISCRIMINATION ANALYSIS

| PROBE | Number of specimens | Ave. % cells with gain | S.D. % cells with gain | D.V. gain | S.D.M. gain | p gain | Ave. % cells with loss | S.D. % cells with loss | D.V. loss | S.D.M. point - loss | p loss |
|---|---|---|---|---|---|---|---|---|---|---|---|
| LSI 5p15 | 26 | 34.0385 | 25.1483 | 1.3710 | 1.0576 | 0.000003 | 1.4615 | 1.9022 | 0.2437 | −0.3491 | 0.079773 |
| LSI 7p12 | 26 | 30.1154 | 21.6505 | 1.2708 | 1.0181 | 0.000005 | 1.3462 | 2.2617 | 0.0002 | 0.0110 | 0.952130 |
| CEP 1 | 26 | 27.7308 | 21.7946 | 1.2292 | 1.0687 | 0.000007 | 7.7308 | 19.0527 | 0.0531 | 0.2052 | 0.256410 |
| CEP 6 | 26 | 27.8462 | 24.2976 | 1.1307 | 0.9779 | 0.000012 | 3.7692 | 3.2901 | 0.0609 | −0.1758 | 0.332295 |
| LSI 8q24 | 27 | 22.7407 | 19.3621 | 1.0555 | 0.9388 | 0.000013 | 1.5926 | 1.5753 | 0.3842 | −0.4397 | 0.038297 |
| LSI 20q | 19 | 26.2632 | 22.4297 | 0.9843 | 0.9067 | 0.000395 | 2.6842 | 2.1616 | 0.2546 | −0.3604 | 0.100820 |
| CEP 9 | 26 | 19.6923 | 17.6176 | 0.9834 | 0.8932 | 0.000031 | 6.6154 | 8.2998 | 0.0025 | −0.0364 | 0.832828 |
| LSI 3p14 | 26 | 21.5385 | 17.1912 | 0.9477 | 0.8042 | 0.000043 | 4.2692 | 6.6547 | 0.0379 | 0.1532 | 0.365082 |
| CEP 16 | 19 | 21.9474 | 20.5520 | 0.8635 | 0.8692 | 0.000741 | 8.3684 | 5.9368 | 0.0525 | −0.1631 | 0.398174 |
| CEP 4 | 19 | 20.7368 | 19.5756 | 0.8248 | 0.8083 | 0.000888 | 2.9474 | 1.9571 | 0.0198 | 0.1003 | 0.600639 |
| LSI 3q | 19 | 29.7895 | 24.3278 | 0.8248 | 0.8085 | 0.000889 | 2.6316 | 5.8709 | 0.0016 | −0.0301 | 0.872277 |
| CEP 7 | 26 | 23.1154 | 24.0704 | 0.8126 | 0.8673 | 0.000106 | 2.6154 | 2.8576 | 0.0038 | 0.0442 | 0.801649 |
| LSI 17q21 | 27 | 22.3704 | 21.4658 | 0.8120 | 0.8134 | 0.000077 | 4.2593 | 4.5454 | 0.1735 | −0.3019 | 0.087675 |
| LSI 5q31 | 26 | 22.9231 | 22.2996 | 0.7623 | 0.8153 | 0.000154 | 4.2692 | 5.0482 | 0.0005 | −0.0173 | 0.918489 |
| CEP 3 | 26 | 21.1154 | 24.0671 | 0.6485 | 0.7618 | 0.000377 | 3.9231 | 6.5600 | 0.0010 | 0.0253 | 0.880460 |
| CEP 10 | 25 | 17.1600 | 19.9827 | 0.6154 | 0.7148 | 0.000645 | 3.7000 | 2.9155 | 0.0091 | −0.0676 | 0.723951 |
| CEP 11 | 26 | 18.9231 | 21.5108 | 0.5655 | 0.6818 | 0.000770 | 3.4231 | 3.1135 | 0.0743 | −0.1998 | 0.248755 |
| CEP 8 | 27 | 17.2222 | 21.7155 | 0.5567 | 0.7125 | 0.000646 | 3.2593 | 2.9819 | 0.0863 | −0.2077 | 0.278498 |
| CEP 18 | 25 | 17.0000 | 21.1325 | 0.5128 | 0.6574 | 0.001526 | 5.0800 | 4.1122 | 0.2510 | −0.3545 | 0.070839 |
| LSI 13 | 27 | 13.4444 | 15.3230 | 0.5040 | 0.6259 | 0.001103 | 4.0741 | 3.4744 | 0.0091 | −0.0677 | 0.705658 |
| LSI 9p21 | 26 | 14.9615 | 17.5191 | 0.4736 | 0.6004 | 0.001833 | 9.0000 | 15.5486 | 0.0997 | 0.2693 | 0.128341 |
| LSI 10q23 | 25 | 15.8600 | 13.9280 | 0.4520 | 0.5323 | 0.003606 | 3.3600 | 4.4989 | 0.0052 | 0.0541 | 0.752077 |
| CEP 12 | 26 | 19.3462 | 26.9250 | 0.4383 | 0.6330 | 0.002417 | 3.3208 | 3.4212 | 0.0734 | −0.1931 | 0.286454 |
| CEP 17 | 27 | 16.3704 | 21.9057 | 0.4065 | 0.5726 | 0.002832 | 6.2222 | 5.8001 | 0.4089 | −0.4560 | 0.016682 |
| LSI 17p13 | 27 | 14.1852 | 15.7774 | 0.3844 | 0.5111 | 0.004264 | 7.6296 | 9.9466 | 0.0049 | 0.0553 | 0.738974 |
| LSI 21 | 26 | 17.7844 | 17.8255 | 0.2805 | 0.4198 | 0.016950 | 4.5832 | 3.8505 | 0.0622 | −0.1777 | 0.384519 |
| Ratios: | | | | | | | | | | | |
| 5 p/q imbal. | 26 | 28.1566 | 22.1019 | 1.0505 | 0.8962 | 0.000020 | 5.3885 | 7.0458 | 0.0897 | 0.2470 | 0.154145 |
| LSI 7p12/CEP 7 | 26 | 15.8237 | 10.9781 | 0.6764 | 0.6496 | 0.000446 | 3.8921 | 4.6890 | 0.2832 | 0.4018 | 0.022057 |
| LSI 8q24/CEP 8 | 27 | 13.7445 | 8.6033 | 0.6747 | 0.6340 | 0.000477 | 5.2233 | 7.7125 | 0.0825 | 0.2408 | 0.160626 |
| LSI 3p14/CEP 3 | 26 | 12.5385 | 9.8599 | 0.2517 | 0.3736 | 0.033580 | 14.6154 | 18.1242 | 0.3618 | 0.5307 | 0.005431 |
| LSI 17q21/CEP | 27 | 16.7089 | 9.9709 | 0.2181 | 0.3440 | 0.048699 | 8.4901 | 8.3931 | 0.0699 | 0.2172 | 0.200321 |
| LSI 10q23/CEP | 25 | 12.3232 | 8.1702 | 0.1431 | 0.2708 | 0.138690 | 11.8277 | 17.5057 | 0.2519 | 0.4596 | 0.019653 |

TABLE 4-continued

DISCRIMINATION ANALYSIS

| PROBE | Number of specimens | Ave. % cells with gain | S.D. % cells with gain | D.V. gain | S.D.M. gain | p gain | Ave. % cells with loss | S.D. % cells with loss | D.V. loss | S.D.M. point − loss | p loss |
|---|---|---|---|---|---|---|---|---|---|---|---|
| LSI 9p21/CEP 9 | 26 | 9.2480 | 9.1323 | 0.0171 | 0.0930 | 0.608094 | 13.3700 | 16.2368 | 0.3208 | 0.4688 | 0.009422 |
| LSI 17p13/CEP | 27 | 11.3749 | 9.4349 | 0.0000 | 0.0051 | 0.976201 | 17.4138 | 20.1651 | 0.3132 | 0.4915 | 0.007889 |

TABLE 5

Sensitivity and Specificity of Lung Tumor Detection

| PROBE | LOSS/ GAIN | SPECI- FICITY | SENSI- TIVITY | SENS * SPEC | VEC- TOR | # TUMOR SPECI- MENS | PROBE | LOSS/ GAI | SPECIFICIT | SENSI- TIVITY | SENS * SPEC | VEC- TOR | # TUMOR SPECI- MENS |
|---|---|---|---|---|---|---|---|---|---|---|---|---|---|
| \multicolumn{7}{c}{CUTOFF = 5% CELLS WITH GAINS OR LOSSES} | \multicolumn{7}{c}{CUTOFF = 10% CELLS WITH GAINS OR LOSSES} |
| CEP 1 | gain | 1.000 | 0.923 | 0.923 | 0.077 | 26 | 8q24 | gain | 1.000 | 0.778 | 0.778 | 0.222 | 27 |
| 8q24 | gain | 0.900 | 0.815 | 0.733 | 0.210 | 27 | LSI 5p15 | gain | 1.000 | 0.769 | 0.769 | 0.231 | 26 |
| CEP 16 | gain | 1.000 | 0.737 | 0.737 | 0.263 | 19 | 7p12 | gain | 0.900 | 0.692 | 0.623 | 0.324 | 26 |
| CEP 6 | gain | 0.900 | 0.731 | 0.658 | 0.287 | 26 | CEP 1 | gain | 1.000 | 0.654 | 0.654 | 0.346 | 26 |
| CEP 9 | gain | 0.900 | 0.731 | 0.658 | 0.287 | 26 | CEP 9 | gain | 1.000 | 0.654 | 0.654 | 0.346 | 26 |
| LSI 5q31 | gain | 0.900 | 0.692 | 0.623 | 0.324 | 26 | LSI 3q | gain | 0.900 | 0.632 | 0.568 | 0.382 | 19 |
| LSI 20q | gain | 0.800 | 0.737 | 0.589 | 0.331 | 19 | CEP 6 | gain | 1.000 | 0.615 | 0.615 | 0.385 | 26 |
| 3p14 | gain | 0.700 | 0.846 | 0.592 | 0.337 | 26 | 17q21 | gain | 1.000 | 0.593 | 0.593 | 0.407 | 27 |
| 17q21 | gain | 0.800 | 0.704 | 0.563 | 0.357 | 27 | CEP 16 | gain | 1.000 | 0.579 | 0.579 | 0.421 | 19 |
| CEP 4 | gain | 0.800 | 0.684 | 0.547 | 0.374 | 19 | CEP 4 | gain | 1.000 | 0.579 | 0.579 | 0.421 | 19 |
| LSI 5p15 | gain | 0.600 | 0.923 | 0.554 | 0.407 | 26 | LSI 20q | gain | 1.000 | 0.579 | 0.579 | 0.421 | 19 |
| CEP 8 | gain | 1.000 | 0.593 | 0.593 | 0.407 | 27 | LSI 5q31 | gain | 1.000 | 0.577 | 0.577 | 0.423 | 26 |
| LSI 13 | gain | 0.900 | 0.593 | 0.533 | 0.420 | 27 | 3p14 | gain | 0.900 | 0.577 | 0.519 | 0.435 | 26 |
| CEP 11 | gain | 0.900 | 0.577 | 0.519 | 0.435 | 26 | CEP 7 | gain | 1.000 | 0.538 | 0.538 | 0.462 | 26 |
| CEP 10 | gain | 1.000 | 0.560 | 0.560 | 0.440 | 25 | CEP 3 | gain | 1.000 | 0.500 | 0.500 | 0.500 | 26 |
| CEP 17 | gain | 0.900 | 0.556 | 0.500 | 0.456 | 27 | CEP 8 | gain | 1.000 | 0.481 | 0.481 | 0.519 | 27 |
| CEP 3 | gain | 1.000 | 0.538 | 0.538 | 0.462 | 26 | 9p21 | gain | 1.000 | 0.462 | 0.462 | 0.538 | 26 |
| CEP 7 | gain | 1.000 | 0.538 | 0.538 | 0.462 | 26 | CEP 11 | gain | 1.000 | 0.462 | 0.462 | 0.538 | 26 |
| 9p21 | gain | 0.800 | 0.577 | 0.462 | 0.468 | 26 | 10q23 | gain | 0.800 | 0.480 | 0.384 | 0.557 | 25 |
| 10q23 | gain | 0.600 | 0.720 | 0.432 | 0.488 | 25 | CEP 12 | gain | 1.000 | 0.423 | 0.423 | 0.577 | 26 |
| CEP 18 | gain | 0.900 | 0.520 | 0.468 | 0.490 | 25 | LSI 21 | gain | 0.700 | 0.500 | 0.350 | 0.583 | 26 |
| CEP 12 | gain | 1.000 | 0.500 | 0.500 | 0.500 | 26 | CEP 17 | gain | 1.000 | 0.407 | 0.407 | 0.593 | 27 |
| 17p13 | gain | 0.600 | 0.593 | 0.356 | 0.571 | 27 | LSI 13 | gain | 1.000 | 0.407 | 0.407 | 0.593 | 27 |
| LSI 21 | gain | 0.500 | 0.692 | 0.346 | 0.587 | 26 | CEP 10 | gain | 1.000 | 0.400 | 0.400 | 0.600 | 25 |
| 7p12 | gain | 0.400 | 0.846 | 0.338 | 0.619 | 26 | CEP 18 | gain | 1.000 | 0.400 | 0.400 | 0.600 | 25 |
| 9p21 | loss | 0.800 | 0.385 | 0.308 | 0.647 | 26 | 17p13 | gain | 0.900 | 0.407 | 0.367 | 0.601 | 27 |
| LSI 13 | loss | 0.700 | 0.370 | 0.259 | 0.697 | 27 | 17p13 | loss | 0.800 | 0.259 | 0.207 | 0.767 | 27 |
| CEP 1 | loss | 0.800 | 0.308 | 0.246 | 0.721 | 26 | CEP 9 | loss | 0.800 | 0.192 | 0.154 | 0.832 | 26 |
| LSI 3q | gain | 0.300 | 0.789 | 0.237 | 0.731 | 19 | LSI 5q31 | loss | 1.000 | 0.154 | 0.154 | 0.846 | 26 |
| 10q23 | loss | 0.900 | 0.240 | 0.216 | 0.767 | 25 | 9p21 | loss | 0.900 | 0.154 | 0.138 | 0.852 | 26 |
| 3p14 | loss | 0.900 | 0.231 | 0.208 | 0.776 | 26 | 3p14 | loss | 1.000 | 0.077 | 0.077 | 0.923 | 26 |
| CEP 11 | loss | 0.700 | 0.269 | 0.188 | 0.790 | 26 | CEP 3 | loss | 1.000 | 0.077 | 0.077 | 0.923 | 26 |
| CEP 6 | loss | 0.700 | 0.269 | 0.188 | 0.790 | 26 | CEP 17 | loss | 0.500 | 0.222 | 0.111 | 0.925 | 27 |
| CEP 12 | loss | 0.900 | 0.192 | 0.173 | 0.814 | 26 | LSI 21 | loss | 0.900 | 0.077 | 0.069 | 0.928 | 26 |
| CEP 7 | loss | 0.900 | 0.192 | 0.173 | 0.814 | 26 | 17q21 | loss | 0.900 | 0.074 | 0.067 | 0.931 | 27 |
| CEP 10 | loss | 0.700 | 0.240 | 0.168 | 0.817 | 25 | CEP 18 | loss | 0.800 | 0.080 | 0.064 | 0.941 | 25 |
| LSI 21 | loss | 0.500 | 0.346 | 0.173 | 0.823 | 26 | LSI 3q | loss | 1.000 | 0.053 | 0.053 | 0.947 | 19 |
| 17q21 | loss | 0.500 | 0.333 | 0.167 | 0.833 | 27 | CEP 16 | loss | 0.400 | 0.263 | 0.105 | 0.950 | 19 |
| CEP 4 | loss | 1.000 | 0.158 | 0.158 | 0.842 | 19 | 10q23 | loss | 1.000 | 0.040 | 0.040 | 0.960 | 25 |
| CEP 16 | loss | 0.300 | 0.526 | 0.158 | 0.845 | 19 | CEP 10 | loss | 1.000 | 0.040 | 0.040 | 0.960 | 25 |
| LSI 5q31 | loss | 0.600 | 0.231 | 0.138 | 0.867 | 26 | CEP 1 | loss | 1.000 | 0.038 | 0.038 | 0.962 | 26 |
| CEP 8 | loss | 0.700 | 0.185 | 0.130 | 0.868 | 27 | CEP 11 | loss | 1.000 | 0.038 | 0.038 | 0.962 | 26 |
| CEP 3 | loss | 0.800 | 0.154 | 0.123 | 0.869 | 26 | CEP 6 | loss | 1.000 | 0.038 | 0.038 | 0.962 | 26 |
| LSI 3q | loss | 0.800 | 0.105 | 0.084 | 0.917 | 19 | LSI 13 | loss | 1.000 | 0.037 | 0.037 | 0.963 | 27 |
| 7p12 | loss | 0.900 | 0.077 | 0.069 | 0.928 | 26 | CEP 12 | loss | 0.900 | 0.038 | 0.035 | 0.967 | 26 |
| 17p13 | loss | 0.300 | 0.370 | 0.111 | 0.942 | 27 | 7p12 | loss | 1.000 | 0.000 | 0.000 | 1.000 | 26 |
| LSI 5p15 | loss | 0.900 | 0.038 | 0.035 | 0.967 | 26 | 8q24 | loss | 1.000 | 0.000 | 0.000 | 1.000 | 27 |
| 8q24 | loss | 0.900 | 0.037 | 0.033 | 0.968 | 27 | CEP 4 | loss | 1.000 | 0.000 | 0.000 | 1.000 | 19 |
| LSI 20q | loss | 0.800 | 0.053 | 0.042 | 0.968 | 19 | CEP 7 | loss | 1.000 | 0.000 | 0.000 | 1.000 | 26 |
| CEP 18 | loss | 0.200 | 0.400 | 0.080 | 1.000 | 25 | CEP 8 | loss | 1.000 | 0.000 | 0.000 | 1.000 | 27 |
| CEP 9 | loss | 0.200 | 0.385 | 0.077 | 1.009 | 26 | LSI 5p15 | loss | 1.000 | 0.000 | 0.000 | 1.000 | 26 |
| CEP 17 | loss | 0.100 | 0.519 | 0.052 | 1.021 | 27 | LSI 20q ratios: | loss | 0.900 | 0.000 | 0.000 | 1.005 | 19 |
| 5 p/q imbal. | gain | 0.600 | 0.923 | 0.554 | 0.407 | 26 | 5 p/q imbal. | gain | 0.800 | 0.692 | 0.554 | 0.367 | 26 |
| 8q24/CEP 8 | gain | 0.600 | 0.852 | 0.511 | 0.427 | 27 | 7p12/CEP 7 | gain | 0.900 | 0.577 | 0.519 | 0.435 | 26 |
| 3p14/CEP 3 | loss | 0.700 | 0.654 | 0.458 | 0.458 | 26 | 8q24/CEP 8 | gain | 0.800 | 0.593 | 0.474 | 0.454 | 27 |

TABLE 5-continued

Sensitivity and Specificity of Lung Tumor Detection

| PROBE | LOSS/GAIN | SPECIFICITY | SENSITIVITY | SENS * SPEC | VECTOR | # TUMOR SPECIMENS | PROBE | LOSS/GAI | SPECIFICIT | SENSITIVITY | SENS * SPEC | VECTOR | # TUMOR SPECIMENS |
|---|---|---|---|---|---|---|---|---|---|---|---|---|---|
| 9p21/CEP 9 | loss | 0.800 | 0.577 | 0.462 | 0.468 | 26 | 3p14/CEP 3 | gain | 0.900 | 0.500 | 0.450 | 0.510 | 26 |
| 10q23/CEP 1 | loss | 0.900 | 0.520 | 0.468 | 0.490 | 25 | 3p14/CEP 3 | loss | 1.000 | 0.462 | 0.462 | 0.538 | 26 |
| 7p12/CEP 7 | gain | 0.500 | 0.808 | 0.404 | 0.536 | 26 | 10q23/CEP 1 | gain | 0.700 | 0.480 | 0.336 | 0.600 | 25 |
| 10q23/CEP 1 | gain | 0.500 | 0.760 | 0.380 | 0.555 | 25 | 17q21/CEP 1 | gain | 0.500 | 0.667 | 0.333 | 0.601 | 27 |
| 3p14/CEP 3 | gain | 0.400 | 0.808 | 0.323 | 0.630 | 26 | 17p13/CEP 1 | loss | 0.900 | 0.407 | 0.367 | 0.601 | 27 |
| 8q24/CEP 8 | loss | 1.000 | 0.333 | 0.333 | 0.667 | 27 | 9p21/CEP 9 | loss | 0.900 | 0.346 | 0.312 | 0.661 | 26 |
| 9p21/CEP 9 | gain | 0.400 | 0.615 | 0.246 | 0.713 | 26 | 17q21/CEP 1 | loss | 1.000 | 0.333 | 0.333 | 0.667 | 27 |
| 7p12/CEP 7 | loss | 0.900 | 0.269 | 0.242 | 0.738 | 26 | 17p13/CEP 1 | gain | 0.600 | 0.407 | 0.244 | 0.715 | 27 |
| 17p13/CEP 1 | loss | 0.300 | 0.667 | 0.200 | 0.775 | 27 | 10q23/CEP 1 | loss | 1.000 | 0.240 | 0.240 | 0.760 | 25 |
| 5 p/q imbal. | loss | 0.900 | 0.231 | 0.208 | 0.776 | 26 | 9p21/CEP 9 | gain | 0.800 | 0.231 | 0.185 | 0.795 | 26 |
| 17q21/CEP 1 | loss | 0.300 | 0.593 | 0.178 | 0.810 | 27 | 7p12/CEP 7 | loss | 1.000 | 0.192 | 0.192 | 0.808 | 26 |
| 17q21/CEP 1 | gain | 0.100 | 0.889 | 0.089 | 0.907 | 27 | 8q24/CEP 8 | loss | 1.000 | 0.111 | 0.111 | 0.889 | 27 |
| 17p13/CEP 1 | gain | 0.100 | 0.704 | 0.070 | 0.948 | 27 | 5 p/q imbal. | loss | 1.000 | 0.038 | 0.038 | 0.962 | 26 |
| CUTOFF = 20% CELLS WITH GAINS OR LOSSES | | | | | | | CUTOFF = 30% CELLS WITH GAINS OR LOSSES | | | | | | |
| LSI 5p15 | gain | 1.000 | 0.654 | 0.654 | 0.346 | 26 | LSI 5p15 | gain | 1.000 | 0.577 | 0.577 | 0.423 | 26 |
| 7p12 | gain | 1.000 | 0.615 | 0.615 | 0.385 | 26 | 7p12 | gain | 1.000 | 0.500 | 0.500 | 0.500 | 26 |
| LSI 3q | gain | 1.000 | 0.579 | 0.579 | 0.421 | 19 | CEP 6 | gain | 1.000 | 0.500 | 0.500 | 0.500 | 26 |
| CEP 1 | gain | 1.000 | 0.538 | 0.538 | 0.462 | 26 | LSI 20q | gain | 1.000 | 0.474 | 0.474 | 0.526 | 19 |
| 3p14 | gain | 1.000 | 0.500 | 0.500 | 0.500 | 26 | LSI 3q | gain | 1.000 | 0.474 | 0.474 | 0.526 | 19 |
| CEP 6 | gain | 1.000 | 0.500 | 0.500 | 0.500 | 26 | CEP 1 | gain | 1.000 | 0.385 | 0.385 | 0.615 | 26 |
| CEP 16 | gain | 1.000 | 0.474 | 0.474 | 0.526 | 19 | CEP 7 | gain | 1.000 | 0.385 | 0.385 | 0.615 | 26 |
| CEP 4 | gain | 1.000 | 0.474 | 0.474 | 0.526 | 19 | 3p14 | gain | 1.000 | 0.346 | 0.346 | 0.654 | 26 |
| LSI 20q | gain | 1.000 | 0.474 | 0.474 | 0.526 | 19 | LSI 5q31 | gain | 1.000 | 0.346 | 0.346 | 0.654 | 26 |
| CEP 7 | gain | 1.000 | 0.462 | 0.462 | 0.538 | 26 | CEP 3 | gain | 1.000 | 0.308 | 0.308 | 0.692 | 26 |
| 17q21 | gain | 1.000 | 0.444 | 0.444 | 0.556 | 27 | 17q21 | gain | 1.000 | 0.296 | 0.296 | 0.704 | 27 |
| 8q24 | gain | 1.000 | 0.444 | 0.444 | 0.556 | 27 | CEP 11 | gain | 1.000 | 0.269 | 0.269 | 0.731 | 26 |
| CEP 3 | gain | 1.000 | 0.423 | 0.423 | 0.577 | 26 | CEP 12 | gain | 1.000 | 0.269 | 0.269 | 0.731 | 26 |
| CEP 9 | gain | 1.000 | 0.423 | 0.423 | 0.577 | 26 | CEP 16 | gain | 1.000 | 0.263 | 0.263 | 0.737 | 19 |
| LSI 5q31 | gain | 1.000 | 0.423 | 0.423 | 0.577 | 26 | CEP 4 | gain | 1.000 | 0.263 | 0.263 | 0.737 | 19 |
| CEP 11 | gain | 1.000 | 0.385 | 0.385 | 0.615 | 26 | CEP 10 | gain | 1.000 | 0.240 | 0.240 | 0.760 | 25 |
| CEP 10 | gain | 1.000 | 0.360 | 0.360 | 0.640 | 25 | CEP 18 | gain | 1.000 | 0.240 | 0.240 | 0.760 | 25 |
| CEP 12 | gain | 1.000 | 0.346 | 0.346 | 0.654 | 26 | 8q24 | gain | 1.000 | 0.222 | 0.222 | 0.778 | 27 |
| 10q23 | gain | 1.000 | 0.320 | 0.320 | 0.680 | 25 | CEP 17 | gain | 1.000 | 0.222 | 0.222 | 0.778 | 27 |
| CEP 18 | gain | 1.000 | 0.320 | 0.320 | 0.680 | 25 | CEP 9 | gain | 1.000 | 0.192 | 0.192 | 0.808 | 26 |
| CEP 17 | gain | 1.000 | 0.296 | 0.296 | 0.704 | 27 | LSI 21 | gain | 1.000 | 0.192 | 0.192 | 0.808 | 26 |
| CEP 8 | gain | 1.000 | 0.296 | 0.296 | 0.704 | 27 | 17p13 | gain | 1.000 | 0.185 | 0.185 | 0.815 | 27 |
| LSI 21 | gain | 0.900 | 0.269 | 0.242 | 0.738 | 26 | CEP 8 | gain | 1.000 | 0.185 | 0.185 | 0.815 | 27 |
| 9p21 | gain | 1.000 | 0.231 | 0.231 | 0.769 | 26 | 10q23 | gain | 1.000 | 0.160 | 0.160 | 0.840 | 25 |
| 17p13 | gain | 1.000 | 0.222 | 0.222 | 0.778 | 27 | 9p21 | gain | 1.000 | 0.154 | 0.154 | 0.846 | 26 |
| LSI 13 | gain | 1.000 | 0.148 | 0.148 | 0.852 | 27 | 9p21 | loss | 1.000 | 0.115 | 0.115 | 0.885 | 26 |
| 9p21 | loss | 1.000 | 0.115 | 0.115 | 0.885 | 26 | LSI 13 | gain | 1.000 | 0.111 | 0.111 | 0.889 | 27 |
| CEP 3 | loss | 1.000 | 0.077 | 0.077 | 0.923 | 26 | CEP 1 | loss | 1.000 | 0.038 | 0.038 | 0.962 | 26 |
| 17p13 | loss | 1.000 | 0.074 | 0.074 | 0.926 | 27 | CEP 9 | loss | 1.000 | 0.038 | 0.038 | 0.962 | 26 |
| CEP 16 | loss | 1.000 | 0.053 | 0.053 | 0.947 | 19 | 17p13 | loss | 1.000 | 0.037 | 0.037 | 0.963 | 27 |
| LSI 3q | loss | 1.000 | 0.053 | 0.053 | 0.947 | 19 | 10q23 | loss | 1.000 | 0.000 | 0.000 | 1.000 | 25 |
| 3p14 | loss | 1.000 | 0.038 | 0.038 | 0.962 | 26 | 17q21 | loss | 1.000 | 0.000 | 0.000 | 1.000 | 27 |
| CEP 1 | loss | 1.000 | 0.038 | 0.038 | 0.962 | 26 | 3p14 | loss | 1.000 | 0.000 | 0.000 | 1.000 | 26 |
| CEP 9 | loss | 1.000 | 0.038 | 0.038 | 0.962 | 26 | 7p12 | loss | 1.000 | 0.000 | 0.000 | 1.000 | 26 |
| LSI 5q31 | loss | 1.000 | 0.038 | 0.038 | 0.962 | 26 | 8q24 | loss | 1.000 | 0.000 | 0.000 | 1.000 | 27 |
| CEP 17 | loss | 1.000 | 0.037 | 0.037 | 0.963 | 27 | CEP 10 | loss | 1.000 | 0.000 | 0.000 | 1.000 | 25 |
| 10q23 | loss | 1.000 | 0.000 | 0.000 | 1.000 | 25 | CEP 11 | loss | 1.000 | 0.000 | 0.000 | 1.000 | 26 |
| 17q21 | loss | 1.000 | 0.000 | 0.000 | 1.000 | 27 | CEP 12 | loss | 1.000 | 0.000 | 0.000 | 1.000 | 26 |
| 7p12 | loss | 1.000 | 0.000 | 0.000 | 1.000 | 26 | CEP 16 | loss | 1.000 | 0.000 | 0.000 | 1.000 | 19 |
| 8q24 | loss | 1.000 | 0.000 | 0.000 | 1.000 | 27 | CEP 17 | loss | 1.000 | 0.000 | 0.000 | 1.000 | 27 |
| CEP 10 | loss | 1.000 | 0.000 | 0.000 | 1.000 | 25 | CEP 18 | loss | 1.000 | 0.000 | 0.000 | 1.000 | 25 |
| CEP 11 | loss | 1.000 | 0.000 | 0.000 | 1.000 | 26 | CEP 3 | loss | 1.000 | 0.000 | 0.000 | 1.000 | 26 |
| CEP 12 | loss | 1.000 | 0.000 | 0.000 | 1.000 | 26 | CEP 4 | loss | 1.000 | 0.000 | 0.000 | 1.000 | 19 |
| CEP 18 | loss | 1.000 | 0.000 | 0.000 | 1.000 | 25 | CEP 6 | loss | 1.000 | 0.000 | 0.000 | 1.000 | 26 |
| CEP 4 | loss | 1.000 | 0.000 | 0.000 | 1.000 | 19 | CEP 7 | loss | 1.000 | 0.000 | 0.000 | 1.000 | 26 |
| CEP 6 | loss | 1.000 | 0.000 | 0.000 | 1.000 | 26 | CEP 8 | loss | 1.000 | 0.000 | 0.000 | 1.000 | 27 |
| CEP 7 | loss | 1.000 | 0.000 | 0.000 | 1.000 | 26 | LSI 13 | loss | 1.000 | 0.000 | 0.000 | 1.000 | 27 |
| CEP 8 | loss | 1.000 | 0.000 | 0.000 | 1.000 | 27 | LSI 20q | loss | 1.000 | 0.000 | 0.000 | 1.000 | 19 |
| LSI 13 | loss | 1.000 | 0.000 | 0.000 | 1.000 | 27 | LSI 21 | loss | 1.000 | 0.000 | 0.000 | 1.000 | 26 |
| LSI 20q | loss | 1.000 | 0.000 | 0.000 | 1.000 | 19 | LSI 3q | loss | 1.000 | 0.000 | 0.000 | 1.000 | 19 |
| LSI 21 | loss | 1.000 | 0.000 | 0.000 | 1.000 | 26 | LSI 5p15 | loss | 1.000 | 0.000 | 0.000 | 1.000 | 26 |
| LSI 5p15 | loss | 1.000 | 0.000 | 0.000 | 1.000 | 26 | LSI 5q31 | loss | 1.000 | 0.000 | 0.000 | 1.000 | 26 |
| 5 p/q imbal. | gain | 1.000 | 0.500 | 0.500 | 0.500 | 26 | 5 p/q imbal. | gain | 1.000 | 0.385 | 0.385 | 0.615 | 26 |
| 17q21/CEP 1 | gain | 1.000 | 0.370 | 0.370 | 0.630 | 27 | 17p13/CEP 1 | loss | 1.000 | 0.185 | 0.185 | 0.815 | 27 |
| 7p12/CEP 7 | gain | 1.000 | 0.346 | 0.346 | 0.654 | 26 | 10q23/CEP 1 | loss | 1.000 | 0.160 | 0.160 | 0.840 | 25 |
| 17p13/CEP 1 | loss | 1.000 | 0.259 | 0.259 | 0.741 | 27 | 3p14/CEP 3 | loss | 1.000 | 0.115 | 0.115 | 0.885 | 26 |
| 3p14/CEP 3 | loss | 1.000 | 0.192 | 0.192 | 0.808 | 26 | 3p14/CEP 3 | gain | 1.000 | 0.115 | 0.115 | 0.885 | 26 |
| 9p21/CEP 9 | loss | 1.000 | 0.192 | 0.192 | 0.808 | 26 | 7p12/CEP 7 | gain | 1.000 | 0.115 | 0.115 | 0.885 | 26 |

TABLE 5-continued

Sensitivity and Specificity of Lung Tumor Detection

| PROBE | LOSS/GAIN | SPECIFICITY | SENSITIVITY | SENS * SPEC | VECTOR | # TUMOR SPECIMENS | PROBE | LOSS/GAI | SPECIFICIT | SENSITIVITY | SENS * SPEC | VECTOR | # TUMOR SPECIMENS |
|---|---|---|---|---|---|---|---|---|---|---|---|---|---|
| 17p13/CEP 1 | gain | 0.900 | 0.185 | 0.167 | 0.821 | 27 | 9p21/CEP 9 | loss | 1.000 | 0.115 | 0.115 | 0.885 | 26 |
| 10q23/CEP 1 | loss | 1.000 | 0.160 | 0.160 | 0.840 | 25 | 10q23/CEP 1 | gain | 1.000 | 0.080 | 0.080 | 0.920 | 25 |
| 3p14/CEP 3 | gain | 1.000 | 0.154 | 0.154 | 0.846 | 26 | 9p21/CEP 9 | gain | 1.000 | 0.077 | 0.077 | 0.923 | 26 |
| 8q24/CEP 8 | gain | 1.000 | 0.148 | 0.148 | 0.852 | 27 | 17q21/CEP 1 | gain | 1.000 | 0.074 | 0.074 | 0.926 | 27 |
| 10q23/CEP 1 | gain | 1.000 | 0.120 | 0.120 | 0.880 | 25 | 17p13/CEP 1 | gain | 1.000 | 0.037 | 0.037 | 0.963 | 27 |
| 17q21/CEP 1 | gain | 1.000 | 0.111 | 0.111 | 0.889 | 27 | 17q21/CEP 1 | loss | 1.000 | 0.037 | 0.037 | 0.963 | 27 |
| 9p21/CEP 9 | gain | 0.900 | 0.077 | 0.069 | 0.928 | 26 | 8q24/CEP 8 | loss | 1.000 | 0.037 | 0.037 | 0.963 | 27 |
| 8q24/CEP 8 | loss | 1.000 | 0.037 | 0.037 | 0.963 | 27 | 8q24/CEP 8 | gain | 1.000 | 0.037 | 0.037 | 0.963 | 27 |
| 5 p/q imbal. | loss | 1.000 | 0.000 | 0.000 | 1.000 | 26 | 5 p/q imbal. | loss | 1.000 | 0.000 | 0.000 | 1.000 | 26 |
| 7p12/CEP 7 | loss | 1.000 | 0.000 | 0.000 | 1.000 | 26 | 7p12/CEP 7 | loss | 1.000 | 0.000 | 0.000 | 1.000 | 26 |
| CUTOFF = 40% CELLS WITH GAINS OR LOSSES | | | | | | | CUTOFF = 50% CELLS WITH GAINS OR LOSSES | | | | | | |
| 7p12 | gain | 1.000 | 0.385 | 0.385 | 0.615 | 26 | CEP 1 | gain | 1.000 | 0.231 | 0.231 | 0.769 | 26 |
| CEP 1 | gain | 1.000 | 0.346 | 0.346 | 0.654 | 26 | LSI 20q | gain | 1.000 | 0.211 | 0.211 | 0.789 | 19 |
| LSI 3q | gain | 1.000 | 0.316 | 0.316 | 0.684 | 19 | LSI 3q | gain | 1.000 | 0.211 | 0.211 | 0.789 | 19 |
| CEP 6 | gain | 1.000 | 0.308 | 0.308 | 0.692 | 26 | CEP 7 | gain | 1.000 | 0.192 | 0.192 | 0.808 | 26 |
| CEP 7 | gain | 1.000 | 0.308 | 0.308 | 0.692 | 26 | LSI 5p15 | gain | 1.000 | 0.192 | 0.192 | 0.808 | 26 |
| LSI 5p15 | gain | 1.000 | 0.308 | 0.308 | 0.692 | 26 | 7p12 | gain | 1.000 | 0.154 | 0.154 | 0.846 | 26 |
| LSI 20q | gain | 1.000 | 0.211 | 0.211 | 0.789 | 19 | CEP 11 | gain | 1.000 | 0.154 | 0.154 | 0.846 | 26 |
| CEP 18 | gain | 1.000 | 0.200 | 0.200 | 0.800 | 25 | CEP 3 | gain | 1.000 | 0.154 | 0.154 | 0.846 | 26 |
| 17q21 | gain | 1.000 | 0.185 | 0.185 | 0.815 | 27 | CEP 6 | gain | 1.000 | 0.154 | 0.154 | 0.846 | 26 |
| CEP 10 | gain | 1.000 | 0.160 | 0.160 | 0.840 | 25 | CEP 12 | gain | 1.000 | 0.115 | 0.115 | 0.885 | 26 |
| CEP 16 | gain | 1.000 | 0.158 | 0.158 | 0.842 | 19 | LSI 5q31 | gain | 1.000 | 0.115 | 0.115 | 0.885 | 26 |
| CEP 4 | gain | 1.000 | 0.158 | 0.158 | 0.842 | 19 | 17q21 | gain | 1.000 | 0.111 | 0.111 | 0.889 | 27 |
| CEP 11 | gain | 1.000 | 0.154 | 0.154 | 0.846 | 26 | 8q24 | gain | 1.000 | 0.111 | 0.111 | 0.889 | 27 |
| CEP 12 | gain | 1.000 | 0.154 | 0.154 | 0.846 | 26 | CEP 17 | gain | 1.000 | 0.111 | 0.111 | 0.889 | 27 |
| CEP 3 | gain | 1.000 | 0.154 | 0.154 | 0.846 | 26 | CEP 8 | gain | 1.000 | 0.111 | 0.111 | 0.889 | 27 |
| CEP 17 | gain | 1.000 | 0.148 | 0.148 | 0.852 | 27 | CEP 16 | gain | 1.000 | 0.105 | 0.105 | 0.895 | 19 |
| 3p14 | gain | 1.000 | 0.115 | 0.115 | 0.885 | 26 | CEP 4 | gain | 1.000 | 0.105 | 0.105 | 0.895 | 19 |
| 9p21 | loss | 1.000 | 0.115 | 0.115 | 0.885 | 26 | CEP 10 | gain | 1.000 | 0.080 | 0.080 | 0.920 | 25 |
| CEP 9 | gain | 1.000 | 0.115 | 0.115 | 0.885 | 26 | CEP 18 | gain | 1.000 | 0.080 | 0.080 | 0.920 | 25 |
| LSI 21 | gain | 1.000 | 0.115 | 0.115 | 0.885 | 26 | 3p14 | gain | 1.000 | 0.077 | 0.077 | 0.923 | 26 |
| LSI 5q31 | gain | 1.000 | 0.115 | 0.115 | 0.885 | 26 | LSI 21 | gain | 1.000 | 0.077 | 0.077 | 0.923 | 26 |
| 17p13 | gain | 1.000 | 0.111 | 0.111 | 0.889 | 27 | 17p13 | gain | 1.000 | 0.074 | 0.074 | 0.926 | 27 |
| 8q24 | gain | 1.000 | 0.111 | 0.111 | 0.889 | 27 | 9p21 | loss | 1.000 | 0.038 | 0.038 | 0.962 | 26 |
| CEP 8 | gain | 1.000 | 0.111 | 0.111 | 0.889 | 27 | 9p21 | gain | 1.000 | 0.038 | 0.038 | 0.962 | 26 |
| 10q23 | gain | 1.000 | 0.040 | 0.040 | 0.960 | 25 | CEP 1 | loss | 1.000 | 0.038 | 0.038 | 0.962 | 26 |
| 9p21 | gain | 1.000 | 0.038 | 0.038 | 0.962 | 26 | CEP 9 | gain | 1.000 | 0.038 | 0.038 | 0.962 | 26 |
| CEP 1 | loss | 1.000 | 0.038 | 0.038 | 0.962 | 26 | LSI 13 | gain | 1.000 | 0.037 | 0.037 | 0.963 | 27 |
| CEP 9 | loss | 1.000 | 0.038 | 0.038 | 0.962 | 26 | 10q23 | loss | 1.000 | 0.000 | 0.000 | 1.000 | 25 |
| 17p13 | loss | 1.000 | 0.037 | 0.037 | 0.963 | 27 | 10q23 | gain | 1.000 | 0.000 | 0.000 | 1.000 | 25 |
| LSI 13 | gain | 1.000 | 0.037 | 0.037 | 0.963 | 27 | 17p13 | loss | 1.000 | 0.000 | 0.000 | 1.000 | 27 |
| 10q23 | loss | 1.000 | 0.000 | 0.000 | 1.000 | 25 | 17q21 | loss | 1.000 | 0.000 | 0.000 | 1.000 | 27 |
| 17q21 | loss | 1.000 | 0.000 | 0.000 | 1.000 | 27 | 3p14 | loss | 1.000 | 0.000 | 0.000 | 1.000 | 26 |
| 3p14 | loss | 1.000 | 0.000 | 0.000 | 1.000 | 26 | 7p12 | loss | 1.000 | 0.000 | 0.000 | 1.000 | 26 |
| 7p12 | loss | 1.000 | 0.000 | 0.000 | 1.000 | 26 | 8q24 | loss | 1.000 | 0.000 | 0.000 | 1.000 | 27 |
| 8q24 | loss | 1.000 | 0.000 | 0.000 | 1.000 | 27 | CEP 10 | loss | 1.000 | 0.000 | 0.000 | 1.000 | 25 |
| CEP 10 | loss | 1.000 | 0.000 | 0.000 | 1.000 | 25 | CEP 11 | loss | 1.000 | 0.000 | 0.000 | 1.000 | 26 |
| CEP 11 | loss | 1.000 | 0.000 | 0.000 | 1.000 | 26 | CEP 12 | loss | 1.000 | 0.000 | 0.000 | 1.000 | 26 |
| CEP 12 | loss | 1.000 | 0.000 | 0.000 | 1.000 | 26 | CEP 16 | loss | 1.000 | 0.000 | 0.000 | 1.000 | 19 |
| CEP 16 | loss | 1.000 | 0.000 | 0.000 | 1.000 | 19 | CEP 17 | loss | 1.000 | 0.000 | 0.000 | 1.000 | 27 |
| CEP 17 | loss | 1.000 | 0.000 | 0.000 | 1.000 | 27 | CEP 18 | loss | 1.000 | 0.000 | 0.000 | 1.000 | 25 |
| CEP 18 | loss | 1.000 | 0.000 | 0.000 | 1.000 | 25 | CEP 3 | loss | 1.000 | 0.000 | 0.000 | 1.000 | 26 |
| CEP 3 | loss | 1.000 | 0.000 | 0.000 | 1.000 | 26 | CEP 4 | loss | 1.000 | 0.000 | 0.000 | 1.000 | 19 |
| CEP 4 | loss | 1.000 | 0.000 | 0.000 | 1.000 | 19 | CEP 6 | loss | 1.000 | 0.000 | 0.000 | 1.000 | 26 |
| CEP 6 | loss | 1.000 | 0.000 | 0.000 | 1.000 | 26 | CEP 7 | loss | 1.000 | 0.000 | 0.000 | 1.000 | 26 |
| CEP 7 | loss | 1.000 | 0.000 | 0.000 | 1.000 | 26 | CEP 8 | loss | 1.000 | 0.000 | 0.000 | 1.000 | 27 |
| CEP 8 | loss | 1.000 | 0.000 | 0.000 | 1.000 | 27 | CEP 9 | loss | 1.000 | 0.000 | 0.000 | 1.000 | 26 |
| LSI 13 | loss | 1.000 | 0.000 | 0.000 | 1.000 | 27 | LSI 13 | loss | 1.000 | 0.000 | 0.000 | 1.000 | 27 |
| LSI 20q | loss | 1.000 | 0.000 | 0.000 | 1.000 | 19 | LSI 20q | loss | 1.000 | 0.000 | 0.000 | 1.000 | 19 |
| LSI 21 | loss | 1.000 | 0.000 | 0.000 | 1.000 | 26 | LSI 21 | loss | 1.000 | 0.000 | 0.000 | 1.000 | 26 |
| LSI 3q | loss | 1.000 | 0.000 | 0.000 | 1.000 | 19 | LSI 3q | loss | 1.000 | 0.000 | 0.000 | 1.000 | 19 |
| LSI 5p15 | loss | 1.000 | 0.000 | 0.000 | 1.000 | 26 | LSI 5p15 | loss | 1.000 | 0.000 | 0.000 | 1.000 | 26 |
| LSI 5q31 | loss | 1.000 | 0.000 | 0.000 | 1.000 | 26 | LSI 5q31 | loss | 1.000 | 0.000 | 0.000 | 1.000 | 26 |
| 5 p/q imbal. | gain | 1.000 | 0.192 | 0.192 | 0.808 | 26 | 5 p/q imbal. | gain | 1.000 | 0.115 | 0.115 | 0.885 | 26 |
| 17p13/CEP 1 | loss | 1.000 | 0.185 | 0.185 | 0.815 | 27 | 17p13/CEP 1 | loss | 1.000 | 0.111 | 0.111 | 0.889 | 27 |
| 10q23/CEP 1 | loss | 1.000 | 0.080 | 0.080 | 0.920 | 25 | 10q23/CEP 1 | loss | 1.000 | 0.080 | 0.080 | 0.920 | 25 |
| 3p14/CEP 3 | gain | 1.000 | 0.077 | 0.077 | 0.923 | 26 | 3p14/CEP 3 | gain | 1.000 | 0.077 | 0.077 | 0.923 | 26 |
| 9p21/CEP 9 | loss | 1.000 | 0.077 | 0.077 | 0.923 | 26 | 9p21/CEP 9 | loss | 1.000 | 0.077 | 0.077 | 0.923 | 26 |
| 9p21/CEP 9 | gain | 1.000 | 0.038 | 0.038 | 0.962 | 26 | 5 p/q imbal. | loss | 1.000 | 0.000 | 0.000 | 1.000 | 26 |
| 5 p/q imbal. | loss | 1.000 | 0.000 | 0.000 | 1.000 | 26 | 10q23/CEP 1 | gain | 1.000 | 0.000 | 0.000 | 1.000 | 25 |
| 10q23/CEP 1 | gain | 1.000 | 0.000 | 0.000 | 1.000 | 25 | 17p13/CEP 1 | gain | 1.000 | 0.000 | 0.000 | 1.000 | 27 |
| 17p13/CEP 1 | gain | 1.000 | 0.000 | 0.000 | 1.000 | 27 | 17q21/CEP 1 | loss | 1.000 | 0.000 | 0.000 | 1.000 | 27 |

TABLE 5-continued

Sensitivity and Specificity of Lung Tumor Detection

| PROBE | LOSS/ GAIN | SPECI- FICITY | SENSI- TIVITY | SENS * SPEC | VEC- TOR | # TUMOR SPECI- MENS | PROBE | LOSS/ GAI | SPECIFICIT | SENSI- TIVITY | SENS * SPEC | VEC- TOR | # TUMOR SPECI- MENS |
|---|---|---|---|---|---|---|---|---|---|---|---|---|---|
| 17q21/CEP 1 | loss | 1.000 | 0.000 | 0.000 | 1.000 | 27 | 17q21/CEP 1 | gain | 1.000 | 0.000 | 0.000 | 1.000 | 27 |
| 17q21/CEP 1 | gain | 1.000 | 0.000 | 0.000 | 1.000 | 27 | 3p14/CEP 3 | gain | 1.000 | 0.000 | 0.000 | 1.000 | 26 |
| 3p14/CEP 3 | gain | 1.000 | 0.000 | 0.000 | 1.000 | 26 | 7p12/CEP 7 | loss | 1.000 | 0.000 | 0.000 | 1.000 | 26 |
| 7p12/CEP 7 | loss | 1.000 | 0.000 | 0.000 | 1.000 | 26 | 7p12/CEP 7 | gain | 1.000 | 0.000 | 0.000 | 1.000 | 26 |
| 7p12/CEP 7 | gain | 1.000 | 0.000 | 0.000 | 1.000 | 26 | 8q24/CEP 8 | loss | 1.000 | 0.000 | 0.000 | 1.000 | 27 |
| 8q24/CEP 8 | loss | 1.000 | 0.000 | 0.000 | 1.000 | 27 | 8q24/CEP 8 | gain | 1.000 | 0.000 | 0.000 | 1.000 | 27 |
| 8q24/CEP 8 | gain | 1.000 | 0.000 | 0.000 | 1.000 | 27 | 9p21/CEP 9 | gain | 1.000 | 0.000 | 0.000 | 1.000 | 26 |

TABLE 6

Combinations of 2, 3 and 4 Probes at a Cutoff Value of 10%

| PROBE 1 | | PROBE 2 | | PROBE 3 | | PROBE 4 | | SPECIFICITY | SENSITIVITY | SENS * SPEC | VECTOR | # TUMOR SPECIMENS |
|---|---|---|---|---|---|---|---|---|---|---|---|---|
| 2 probe combinations: | | | | | | | | | | | | |
| CEP 17 | gain | 8q24 | gain | | | | | 1.000 | 0.852 | 0.852 | 0.148 | 27 |
| 8q24 | gain | CEP 1 | gain | | | | | 1.000 | 0.846 | 0.846 | 0.154 | 26 |
| 8q24 | gain | LSI 5p15 | gain | | | | | 1.000 | 0.846 | 0.846 | 0.154 | 26 |
| CEP 12 | gain | LSI 5p15 | gain | | | | | 1.000 | 0.846 | 0.846 | 0.154 | 26 |
| 17q21 | gain | 8q24 | gain | | | | | 1.000 | 0.815 | 0.815 | 0.185 | 27 |
| 17q21 | gain | CEP 1 | gain | | | | | 1.000 | 0.808 | 0.808 | 0.192 | 26 |
| 17q21 | gain | LSI 5p15 | gain | | | | | 1.000 | 0.808 | 0.808 | 0.192 | 26 |
| 8q24 | gain | CEP 6 | gain | | | | | 1.000 | 0.808 | 0.808 | 0.192 | 26 |
| 8q24 | gain | CEP 7 | gain | | | | | 1.000 | 0.808 | 0.808 | 0.192 | 26 |
| 8q24 | gain | LSI 5q31 | gain | | | | | 1.000 | 0.808 | 0.808 | 0.192 | 26 |
| 9p21 | gain | 8q24 | gain | | | | | 1.000 | 0.808 | 0.808 | 0.192 | 26 |
| 9p21 | gain | LSI 5p15 | gain | | | | | 1.000 | 0.808 | 0.808 | 0.192 | 26 |
| CEP 11 | gain | 8q24 | gain | | | | | 1.000 | 0.808 | 0.808 | 0.192 | 26 |
| CEP 17 | gain | LSI 5p15 | gain | | | | | 1.000 | 0.808 | 0.808 | 0.192 | 26 |
| CEP 8 | gain | LSI 5p15 | gain | | | | | 1.000 | 0.808 | 0.808 | 0.192 | 26 |
| CEP 9 | gain | 8q24 | gain | | | | | 1.000 | 0.808 | 0.808 | 0.192 | 26 |
| LSI 13 | gain | LSI 5p15 | gain | | | | | 1.000 | 0.808 | 0.808 | 0.192 | 26 |
| LSI 5q31 | gain | LSI 5p15 | gain | | | | | 1.000 | 0.808 | 0.808 | 0.192 | 26 |
| LSI 5p15 | gain | LSI 3q | gain | | | | | 0.875 | 0.842 | 0.737 | 0.201 | 19 |
| 17p13 | gain | 8q24 | gain | | | | | 0.900 | 0.815 | 0.733 | 0.210 | 27 |
| 8q24 | gain | CEP 4 | gain | | | | | 1.000 | 0.789 | 0.789 | 0.211 | 19 |
| CEP 16 | gain | 8q24 | gain | | | | | 1.000 | 0.789 | 0.789 | 0.211 | 19 |
| CEP 16 | gain | CEP 1 | gain | | | | | 1.000 | 0.789 | 0.789 | 0.211 | 19 |
| CEP 16 | gain | LSI 5p15 | gain | | | | | 1.000 | 0.789 | 0.789 | 0.211 | 19 |
| CEP 16 | gain | LSI 5q31 | gain | | | | | 1.000 | 0.789 | 0.789 | 0.211 | 19 |
| CEP 17 | gain | CEP 16 | gain | | | | | 1.000 | 0.789 | 0.789 | 0.211 | 19 |
| LSI 20q | gain | 8q24 | gain | | | | | 1.000 | 0.789 | 0.789 | 0.211 | 19 |
| LSI 20q | gain | CEP 1 | gain | | | | | 1.000 | 0.789 | 0.789 | 0.211 | 19 |
| LSI 20q | gain | LSI 5p15 | gain | | | | | 1.000 | 0.789 | 0.789 | 0.211 | 19 |
| LSI 5p15 | gain | CEP 4 | gain | | | | | 1.000 | 0.789 | 0.789 | 0.211 | 19 |
| 3 probe combinations: | | | | | | | | | | | | |
| 9p21 | gain | 8q24 | gain | LSI 5p15 | gain | | | 1.000 | 0.885 | 0.885 | 0.115 | 26 |
| 9p21 | gain | 8q24 | gain | CEP 1 | gain | | | 1.000 | 0.885 | 0.885 | 0.115 | 26 |
| CEP 12 | gain | 9p21 | gain | LSI 5p15 | gain | | | 1.000 | 0.885 | 0.885 | 0.115 | 26 |
| CEP 17 | gain | 9p21 | gain | 8q24 | gain | | | 1.000 | 0.885 | 0.885 | 0.115 | 26 |
| 17q21 | gain | 9p21 | gain | 8q24 | gain | | | 1.000 | 0.846 | 0.846 | 0.154 | 26 |
| 17q21 | gain | 9p21 | gain | CEP 8 | gain | | | 1.000 | 0.846 | 0.846 | 0.154 | 26 |
| 17q21 | gain | 9p21 | gain | LSI 5p15 | gain | | | 1.000 | 0.846 | 0.846 | 0.154 | 26 |
| 17q21 | gain | 9p21 | gain | CEP 1 | gain | | | 1.000 | 0.846 | 0.846 | 0.154 | 26 |
| 17q21 | gain | CEP 12 | gain | CEP 1 | gain | | | 1.000 | 0.846 | 0.846 | 0.154 | 26 |
| 17q21 | gain | CEP 8 | gain | LSI 5p15 | gain | | | 1.000 | 0.846 | 0.846 | 0.154 | 26 |
| 17q21 | gain | CEP 8 | gain | CEP 1 | gain | | | 1.000 | 0.846 | 0.846 | 0.154 | 26 |
| 17q21 | gain | LSI 13 | gain | 9p21 | gain | | | 1.000 | 0.846 | 0.846 | 0.154 | 26 |
| 17q21 | gain | LSI 13 | gain | LSI 5p15 | gain | | | 1.000 | 0.846 | 0.846 | 0.154 | 26 |
| 17q21 | gain | LSI 13 | gain | CEP 1 | gain | | | 1.000 | 0.846 | 0.846 | 0.154 | 26 |
| 9p21 | gain | 8q24 | gain | CEP 7 | gain | | | 1.000 | 0.846 | 0.846 | 0.154 | 26 |
| 9p21 | gain | 8q24 | gain | CEP 6 | gain | | | 1.000 | 0.846 | 0.846 | 0.154 | 26 |
| 9p21 | gain | 8q24 | gain | LSI 5q31 | gain | | | 1.000 | 0.846 | 0.846 | 0.154 | 26 |
| 9p21 | gain | CEP 8 | gain | LSI 5p15 | gain | | | 1.000 | 0.846 | 0.846 | 0.154 | 26 |
| 9p21 | gain | CEP 8 | gain | CEP 1 | gain | | | 1.000 | 0.846 | 0.846 | 0.154 | 26 |
| 9p21 | gain | CEP 9 | gain | 8q24 | gain | | | 1.000 | 0.846 | 0.846 | 0.154 | 26 |
| 9p21 | gain | LSI 5q31 | gain | LSI 5p15 | gain | | | 1.000 | 0.846 | 0.846 | 0.154 | 26 |

TABLE 6-continued

Combinations of 2, 3 and 4 Probes at a Cutoff Value of 10%

| PROBE 1 | | PROBE 2 | | PROBE 3 | | PROBE 4 | | SPECIFICITY | SENSITIVITY | SENS * SPEC | VECTOR | # TUMOR SPECIMENS |
|---|---|---|---|---|---|---|---|---|---|---|---|---|
| CEP 11 | gain | 9p21 | gain | 8q24 | gain | | | 1.000 | 0.846 | 0.846 | 0.154 | 26 |
| CEP 12 | gain | 9p21 | gain | CEP 6 | gain | | | 1.000 | 0.846 | 0.846 | 0.154 | 26 |
| CEP 12 | gain | CEP 6 | gain | CEP 1 | gain | | | 1.000 | 0.846 | 0.846 | 0.154 | 26 |
| CEP 17 | gain | 9p21 | gain | LSI 5p15 | gain | | | 1.000 | 0.846 | 0.846 | 0.154 | 26 |
| CEP 17 | gain | CEP 8 | gain | LSI 5p15 | gain | | | 1.000 | 0.846 | 0.846 | 0.154 | 26 |
| CEP 17 | gain | CEP 9 | gain | CEP 8 | gain | | | 1.000 | 0.846 | 0.846 | 0.154 | 26 |
| CEP 17 | gain | CEP 9 | gain | CEP 8 | gain | | | 1.000 | 0.846 | 0.846 | 0.154 | 26 |
| CEP 17 | gain | LSI 13 | gain | CEP 9 | gain | | | 1.000 | 0.846 | 0.846 | 0.154 | 26 |
| CEP 17 | gain | LSI 13 | gain | LSI 5p15 | gain | | | 1.000 | 0.846 | 0.846 | 0.154 | 26 |
| CEP 8 | gain | LSI 5q31 | gain | LSI 5p15 | gain | | | 1.000 | 0.846 | 0.846 | 0.154 | 26 |
| CEP 8 | gain | LSI 5q31 | gain | CEP 1 | gain | | | 1.000 | 0.846 | 0.846 | 0.154 | 26 |
| LSI 13 | gain | 9p21 | gain | LSI 5p15 | gain | | | 1.000 | 0.846 | 0.846 | 0.154 | 26 |
| LSI 13 | gain | 9p21 | gain | CEP 1 | gain | | | 1.000 | 0.846 | 0.846 | 0.154 | 26 |
| LSI 13 | gain | LSI 5q31 | gain | LSI 5p15 | gain | | | 1.000 | 0.846 | 0.846 | 0.154 | 26 |
| LSI 13 | gain | LSI 5q31 | gain | CEP 1 | gain | | | 1.000 | 0.846 | 0.846 | 0.154 | 26 |
| | | | | | | 4 probe combinations: | | | | | | |
| 17q21 | gain | 9p21 | gain | CEP 8 | gain | LSI 5p15 | gain | 1.000 | 0.885 | 0.885 | 0.115 | 26 |
| 17q21 | gain | 9p21 | gain | CEP 8 | gain | CEP 1 | gain | 1.000 | 0.885 | 0.885 | 0.115 | 26 |
| 17q21 | gain | CEP 12 | gain | 9p21 | gain | CEP 1 | gain | 1.000 | 0.885 | 0.885 | 0.115 | 26 |
| 17q21 | gain | CEP 17 | gain | LSI 13 | gain | 9p21 | gain | 1.000 | 0.885 | 0.885 | 0.115 | 26 |
| 17q21 | gain | CEP 17 | gain | 9p21 | gain | CEP 8 | gain | 1.000 | 0.885 | 0.885 | 0.115 | 26 |
| 17q21 | gain | LSI 13 | gain | 9p21 | gain | LSI 5p15 | gain | 1.000 | 0.885 | 0.885 | 0.115 | 26 |
| 17q21 | gain | LSI 13 | gain | 9p21 | gain | CEP 1 | gain | 1.000 | 0.885 | 0.885 | 0.115 | 26 |
| 9p21 | gain | CEP 8 | gain | LSI 5q31 | gain | LSI 5p15 | gain | 1.000 | 0.885 | 0.885 | 0.115 | 26 |
| 9p21 | gain | CEP 8 | gain | LSI 5q31 | gain | CEP 1 | gain | 1.000 | 0.885 | 0.885 | 0.115 | 26 |
| CEP 12 | gain | 9p21 | gain | CEP 8 | gain | CEP 1 | gain | 1.000 | 0.885 | 0.885 | 0.115 | 26 |
| CEP 12 | gain | 9p21 | gain | CEP 6 | gain | CEP 1 | gain | 1.000 | 0.885 | 0.885 | 0.115 | 26 |
| CEP 12 | gain | 9p21 | gain | CEP 3 | gain | CEP 1 | gain | 1.000 | 0.885 | 0.885 | 0.115 | 26 |
| CEP 17 | gain | 9p21 | gain | CEP 9 | gain | CEP 8 | gain | 1.000 | 0.885 | 0.885 | 0.115 | 26 |
| CEP 17 | gain | 9p21 | gain | CEP 8 | gain | CEP 6 | gain | 1.000 | 0.885 | 0.885 | 0.115 | 26 |
| CEP 17 | gain | 9p21 | gain | CEP 8 | gain | LSI 5p15 | gain | 1.000 | 0.885 | 0.885 | 0.115 | 26 |
| CEP 17 | gain | 9p21 | gain | CEP 8 | gain | CEP 1 | gain | 1.000 | 0.885 | 0.885 | 0.115 | 26 |
| CEP 17 | gain | CEP 12 | gain | 9p21 | gain | CEP 6 | gain | 1.000 | 0.885 | 0.885 | 0.115 | 26 |
| CEP 17 | gain | LSI 13 | gain | 9p21 | gain | CEP 9 | gain | 1.000 | 0.885 | 0.885 | 0.115 | 26 |
| CEP 17 | gain | LSI 13 | gain | 9p21 | gain | CEP 6 | gain | 1.000 | 0.885 | 0.885 | 0.115 | 26 |
| CEP 17 | gain | LSI 13 | gain | 9p21 | gain | LSI 5p15 | gain | 1.000 | 0.885 | 0.885 | 0.115 | 26 |
| CEP 17 | gain | LSI 13 | gain | 9p21 | gain | CEP 1 | gain | 1.000 | 0.885 | 0.885 | 0.115 | 26 |
| LSI 13 | gain | 9p21 | gain | LSI 5q31 | gain | LSI 5p15 | gain | 1.000 | 0.885 | 0.885 | 0.115 | 26 |
| LSI 13 | gain | 9p21 | gain | LSI 5q31 | gain | CEP 1 | gain | 1.000 | 0.885 | 0.885 | 0.115 | 26 |
| LSI 13 | gain | CEP 12 | gain | 9p21 | gain | CEP 1 | gain | 1.000 | 0.885 | 0.885 | 0.115 | 26 |
| CEP 17 | gain | CEP 10 | gain | 9p21 | gain | CEP 8 | gain | 1.000 | 0.880 | 0.880 | 0.120 | 25 |
| CEP 17 | gain | LSI 13 | gain | CEP 10 | gain | 9p21 | gain | 1.000 | 0.880 | 0.880 | 0.120 | 25 |

TABLE 7

Combinations of 2, 3 and 4 Probes at a Cutoff Value of 20%

| PROBE 1 | | PROBE 2 | | PROBE 3 | | PROBE 4 | | SPECIFICITY | SENSI-TIVITY | SENS * SPEC | VECTOR | # TUMOR SPECIMENS |
|---|---|---|---|---|---|---|---|---|---|---|---|---|
| | | | | | | 2 probe combinations | | | | | | |
| LSI 5p15 | gain | LSI 3q | gain | | | | | 1.000 | 0.789 | 0.789 | 0.211 | 19 |
| CEP 16 | gain | LSI 5p15 | gain | | | | | 1.000 | 0.737 | 0.737 | 0.263 | 19 |
| LSI 20q | gain | LSI 5p15 | gain | | | | | 1.000 | 0.737 | 0.737 | 0.263 | 19 |
| LSI 5p15 | gain | CEP 4 | gain | | | | | 1.000 | 0.737 | 0.737 | 0.263 | 19 |
| 17q21 | gain | LSI 5p15 | gain | | | | | 1.000 | 0.731 | 0.731 | 0.269 | 26 |
| 8q24 | gain | LSI 5p15 | gain | | | | | 1.000 | 0.731 | 0.731 | 0.269 | 26 |
| CEP 6 | gain | LSI 5p15 | gain | | | | | 1.000 | 0.731 | 0.731 | 0.269 | 26 |
| CEP 9 | gain | LSI 5p15 | gain | | | | | 1.000 | 0.731 | 0.731 | 0.269 | 26 |
| LSI 5p15 | gain | 3p14 | gain | | | | | 1.000 | 0.731 | 0.731 | 0.269 | 26 |
| LSI 5p15 | gain | CEP 3 | gain | | | | | 1.000 | 0.731 | 0.731 | 0.269 | 26 |
| 5 p/q imbal. | gain | LSI 5p15 | gain | | | | | 1.000 | 0.692 | 0.692 | 0.308 | 26 |
| 5 p/q imbal. | gain | LSI 5q31 | gain | | | | | 1.000 | 0.692 | 0.692 | 0.308 | 26 |
| 7p12 | gain | LSI 5p15 | gain | | | | | 1.000 | 0.692 | 0.692 | 0.308 | 26 |
| 8q24 | gain | 7p12 | gain | | | | | 1.000 | 0.692 | 0.692 | 0.308 | 26 |
| 8q24 | gain | CEP 6 | gain | | | | | 1.000 | 0.692 | 0.692 | 0.308 | 26 |
| CEP 12 | gain | LSI 5p15 | gain | | | | | 1.000 | 0.692 | 0.692 | 0.308 | 26 |
| CEP 17 | gain | LSI 5p15 | gain | | | | | 1.000 | 0.692 | 0.692 | 0.308 | 26 |
| CEP 7 | gain | LSI 5p15 | gain | | | | | 1.000 | 0.692 | 0.692 | 0.308 | 26 |
| CEP 8 | gain | LSI 5p15 | gain | | | | | 1.000 | 0.692 | 0.692 | 0.308 | 26 |

TABLE 7-continued

Combinations of 2, 3 and 4 Probes at a Cutoff Value of 20%

| PROBE 1 | | PROBE 2 | | PROBE 3 | | PROBE 4 | | SPECIFICITY | SENSI-TIVITY | SENS * SPEC | VECTOR | # TUMOR SPECIMENS |
|---|---|---|---|---|---|---|---|---|---|---|---|---|
| CEP 9 | gain | 3p14 | gain | | | | | 1.000 | 0.692 | 0.692 | 0.308 | 26 |
| LSI 13 | gain | LSI 5p15 | gain | | | | | 1.000 | 0.692 | 0.692 | 0.308 | 26 |
| LSI 5p15 | gain | CEP 1 | gain | | | | | 1.000 | 0.692 | 0.692 | 0.308 | 26 |
| 7p12 | gain | LSI 3q | gain | | | | | 1.000 | 0.684 | 0.684 | 0.316 | 19 |
| CEP 12 | gain | LSI 3q | gain | | | | | 1.000 | 0.684 | 0.684 | 0.316 | 19 |
| CEP 7 | gain | LSI 3q | gain | | | | | 1.000 | 0.684 | 0.684 | 0.316 | 19 |
| LSI 5q31 | gain | LSI 3q | gain | | | | | 1.000 | 0.684 | 0.684 | 0.316 | 19 |
| 3 probe combinations and 3 pr comb (1 rat + 1 abs) | | | | | | | | | | | | |
| CEP 12 | gain | LSI 5p15 | gain | LSI 3q | gain | | | 1.000 | 0.842 | 0.842 | 0.158 | 19 |
| 5 p/q imbal. | gain | LSI 5q31 | gain | LSI 3q | gain | | | 1.000 | 0.789 | 0.789 | 0.211 | 19 |
| 8q24 | gain | LSI 5p15 | gain | CEP 4 | gain | | | 1.000 | 0.789 | 0.789 | 0.211 | 19 |
| CEP 12 | gain | LSI 5p15 | gain | CEP 4 | gain | | | 1.000 | 0.789 | 0.789 | 0.211 | 19 |
| CEP 16 | gain | 8q24 | gain | LSI 5p15 | gain | | | 1.000 | 0.789 | 0.789 | 0.211 | 19 |
| CEP 16 | gain | CEP 12 | gain | LSI 5p15 | gain | | | 1.000 | 0.789 | 0.789 | 0.211 | 19 |
| LSI 20q | gain | 8q24 | gain | LSI 5p15 | gain | | | 1.000 | 0.789 | 0.789 | 0.211 | 19 |
| LSI 20q | gain | CEP 12 | gain | LSI 5p15 | gain | | | 1.000 | 0.789 | 0.789 | 0.211 | 19 |
| 17q21 | gain | 5 p/q imbal. | gain | LSI 5q31 | gain | | | 1.000 | 0.769 | 0.769 | 0.231 | 26 |
| 17q21 | gain | 8q24 | gain | LSI 5p15 | gain | | | 1.000 | 0.769 | 0.769 | 0.231 | 26 |
| 17q21 | gain | CEP 12 | gain | LSI 5p15 | gain | | | 1.000 | 0.769 | 0.769 | 0.231 | 26 |
| 17q21 | gain | LSI 5p15 | gain | 3p14 | gain | | | 1.000 | 0.769 | 0.769 | 0.231 | 26 |
| 17q21 | gain | LSI 5p15 | gain | CEP 3 | gain | | | 1.000 | 0.769 | 0.769 | 0.231 | 26 |
| 5 p/q imbal. | gain | LSI 5p15 | gain | 3p14 | gain | | | 1.000 | 0.769 | 0.769 | 0.231 | 26 |
| 5 p/q imbal. | gain | LSI 5p15 | gain | CEP 3 | gain | | | 1.000 | 0.769 | 0.769 | 0.231 | 26 |
| 5 p/q imbal. | gain | LSI 5q31 | gain | 3p14 | gain | | | 1.000 | 0.769 | 0.769 | 0.231 | 26 |
| 5 p/q imbal. | gain | LSI 5q31 | gain | CEP 3 | gain | | | 1.000 | 0.769 | 0.769 | 0.231 | 26 |
| 8q24 | gain | 5 p/q imbal. | gain | LSI 5q31 | gain | | | 1.000 | 0.769 | 0.769 | 0.231 | 26 |
| 8q24 | gain | 5 p/q imbal. | gain | LSI 5p15 | gain | | | 1.000 | 0.769 | 0.769 | 0.231 | 26 |
| 8q24 | gain | CEP 6 | gain | LSI 5p15 | gain | | | 1.000 | 0.769 | 0.769 | 0.231 | 26 |
| 8q24 | gain | LSI 5p15 | gain | 3p14 | gain | | | 1.000 | 0.769 | 0.769 | 0.231 | 26 |
| 8q24 | gain | LSI 5p15 | gain | CEP 3 | gain | | | 1.000 | 0.769 | 0.769 | 0.231 | 26 |
| CEP 12 | gain | 8q24 | gain | LSI 5p15 | gain | | | 1.000 | 0.769 | 0.769 | 0.231 | 26 |
| CEP 12 | gain | CEP 6 | gain | LSI 5p15 | gain | | | 1.000 | 0.769 | 0.769 | 0.231 | 26 |
| CEP 12 | gain | CEP 9 | gain | LSI 5p15 | gain | | | 1.000 | 0.769 | 0.769 | 0.231 | 26 |
| CEP 12 | gain | CEP 9 | gain | LSI 5p15 | gain | | | 1.000 | 0.769 | 0.769 | 0.231 | 26 |
| CEP 12 | gain | LSI 5p15 | gain | 3p14 | gain | | | 1.000 | 0.769 | 0.769 | 0.231 | 26 |
| CEP 12 | gain | LSI 5p15 | gain | CEP 3 | gain | | | 1.000 | 0.769 | 0.769 | 0.231 | 26 |
| CEP 6 | gain | 5 p/q imbal. | gain | LSI 5q31 | gain | | | 1.000 | 0.769 | 0.769 | 0.231 | 26 |
| CEP 6 | gain | 5 p/q imbal. | gain | LSI 5p15 | gain | | | 1.000 | 0.769 | 0.769 | 0.231 | 26 |
| CEP 6 | gain | LSI 5p15 | gain | 3p14 | gain | | | 1.000 | 0.769 | 0.769 | 0.231 | 26 |
| CEP 6 | gain | LSI 5p15 | gain | CEP 3 | gain | | | 1.000 | 0.769 | 0.769 | 0.231 | 26 |
| CEP 9 | gain | 5 p/q imbal. | gain | LSI 5q31 | gain | | | 1.000 | 0.769 | 0.769 | 0.231 | 26 |
| CEP 9 | gain | 5 p/q imbal. | gain | LSI 5p15 | gain | | | 1.000 | 0.769 | 0.769 | 0.231 | 26 |
| CEP 9 | gain | 8q24 | gain | 3p14 | gain | | | 1.000 | 0.769 | 0.769 | 0.231 | 26 |
| CEP 9 | gain | LSI 5p15 | gain | 3p14 | gain | | | 1.000 | 0.769 | 0.769 | 0.231 | 26 |
| CEP 9 | gain | LSI 5p15 | gain | CEP 3 | gain | | | 1.000 | 0.769 | 0.769 | 0.231 | 26 |
| 4 probe combinations and 4 pr comb (1 rat + 2 abs) | | | | | | | | | | | | |
| CEP 12 | gain | 8q24 | gain | LSI 5p15 | gain | CEP 4 | gain | 1.000 | 0.842 | 0.842 | 0.158 | 19 |
| CEP 12 | gain | 5 p/q imbal. | gain | LSI 5q31 | gain | LSI 3q | gain | 1.000 | 0.842 | 0.842 | 0.158 | 19 |
| CEP 16 | gain | CEP 12 | gain | 8q24 | gain | LSI 5p15 | gain | 1.000 | 0.842 | 0.842 | 0.158 | 19 |
| LSI 20q | gain | CEP 12 | gain | 8q24 | gain | LSI 5p15 | gain | 1.000 | 0.842 | 0.842 | 0.158 | 19 |
| 17p13 | gain | CEP 9 | gain | 5 p/q imbal. | gain | CEP 3 | gain | 1.000 | 0.808 | 0.808 | 0.192 | 26 |
| 17q21 | gain | CEP 12 | gain | 5 p/q imbal. | gain | LSI 5q31 | gain | 1.000 | 0.808 | 0.808 | 0.192 | 26 |
| 17q21 | gain | CEP 12 | gain | 8q24 | gain | LSI 5p15 | gain | 1.000 | 0.808 | 0.808 | 0.192 | 26 |
| 17q21 | gain | CEP 12 | gain | LSI 5p15 | gain | 3p14 | gain | 1.000 | 0.808 | 0.808 | 0.192 | 26 |
| 17q21 | gain | CEP 12 | gain | LSI 5p15 | gain | CEP 3 | gain | 1.000 | 0.808 | 0.808 | 0.192 | 26 |
| 17q21 | gain | 8q24 | gain | 5 p/q imbal. | gain | LSI 5q31 | gain | 1.000 | 0.808 | 0.808 | 0.192 | 26 |
| 17q21 | gain | 8q24 | gain | 5 p/q imbal. | gain | LSI 5p15 | gain | 1.000 | 0.808 | 0.808 | 0.192 | 26 |
| 17q21 | gain | 8q24 | gain | LSI 5p15 | gain | 3p14 | gain | 1.000 | 0.808 | 0.808 | 0.192 | 26 |
| 17q21 | gain | 8q24 | gain | LSI 5p15 | gain | CEP 3 | gain | 1.000 | 0.808 | 0.808 | 0.192 | 26 |
| 17q21 | gain | 5 p/q imbal. | gain | LSI 5q31 | gain | 3p14 | gain | 1.000 | 0.808 | 0.808 | 0.192 | 26 |
| 17q21 | gain | 5 p/q imbal. | gain | LSI 5p15 | gain | 3p14 | gain | 1.000 | 0.808 | 0.808 | 0.192 | 26 |
| 17q21 | gain | 5 p/q imbal. | gain | LSI 5q31 | gain | CEP 3 | gain | 1.000 | 0.808 | 0.808 | 0.192 | 26 |
| 17q21 | gain | 5 p/q imbal. | gain | LSI 5p15 | gain | CEP 3 | gain | 1.000 | 0.808 | 0.808 | 0.192 | 26 |
| 8q24 | gain | CEP 6 | gain | 5 p/q imbal. | gain | LSI 5q31 | gain | 1.000 | 0.808 | 0.808 | 0.192 | 26 |
| 8q24 | gain | CEP 6 | gain | 5 p/q imbal. | gain | LSI 5p15 | gain | 1.000 | 0.808 | 0.808 | 0.192 | 26 |
| 8q24 | gain | CEP 6 | gain | LSI 5p15 | gain | 3p14 | gain | 1.000 | 0.808 | 0.808 | 0.192 | 26 |
| 8q24 | gain | CEP 6 | gain | LSI 5p15 | gain | CEP 3 | gain | 1.000 | 0.808 | 0.808 | 0.192 | 26 |
| 8q24 | gain | 5 p/q imbal. | gain | LSI 5q31 | gain | 3p14 | gain | 1.000 | 0.808 | 0.808 | 0.192 | 26 |
| 8q24 | gain | 5 p/q imbal. | gain | LSI 5p15 | gain | 3p14 | gain | 1.000 | 0.808 | 0.808 | 0.192 | 26 |
| 8q24 | gain | 5 p/q imbal. | gain | LSI 5q31 | gain | CEP 3 | gain | 1.000 | 0.808 | 0.808 | 0.192 | 26 |
| 8q24 | gain | 5 p/q imbal. | gain | LSI 5p15 | gain | CEP 3 | gain | 1.000 | 0.808 | 0.808 | 0.192 | 26 |
| 9p21 | gain | 8q24 | gain | CEP 6 | gain | 5 p/q imbal. | gain | 1.000 | 0.808 | 0.808 | 0.192 | 26 |
| CEP 12 | gain | CEP 9 | gain | 8q24 | gain | LSI 5p15 | gain | 1.000 | 0.808 | 0.808 | 0.192 | 26 |

TABLE 7-continued

Combinations of 2, 3 and 4 Probes at a Cutoff Value of 20%

| PROBE 1 | | PROBE 2 | | PROBE 3 | | PROBE 4 | | SPECIFICITY | SENSI- TIVITY | SENS * SPEC | VECTOR | # TUMOR SPECIMENS |
|---|---|---|---|---|---|---|---|---|---|---|---|---|
| CEP 12 | gain | CEP 9 | gain | 5 p/q imbal. | gain | LSI 5p15 | gain | 1.000 | 0.808 | 0.808 | 0.192 | 26 |
| CEP 12 | gain | CEP 9 | gain | 8q24 | gain | 3p14 | gain | 1.000 | 0.808 | 0.808 | 0.192 | 26 |
| CEP 12 | gain | CEP 9 | gain | LSI 5p15 | gain | 3p14 | gain | 1.000 | 0.808 | 0.808 | 0.192 | 26 |
| CEP 12 | gain | CEP 9 | gain | LSI 5p15 | gain | CEP 3 | gain | 1.000 | 0.808 | 0.808 | 0.192 | 26 |
| CEP 12 | gain | CEP 9 | gain | 5 p/q imbal. | gain | LSI 5q31 | gain | 1.000 | 0.808 | 0.808 | 0.192 | 26 |
| CEP 12 | gain | CEP 6 | gain | 5 p/q imbal. | gain | LSI 5p15 | gain | 1.000 | 0.808 | 0.808 | 0.192 | 26 |
| CEP 12 | gain | CEP 6 | gain | LSI 5p15 | gain | 3p14 | gain | 1.000 | 0.808 | 0.808 | 0.192 | 26 |
| CEP 12 | gain | CEP 6 | gain | LSI 5p15 | gain | CEP 3 | gain | 1.000 | 0.808 | 0.808 | 0.192 | 26 |
| CEP 12 | gain | CEP 6 | gain | 5 p/q imbal. | gain | LSI 5q31 | gain | 1.000 | 0.808 | 0.808 | 0.192 | 26 |
| CEP 12 | gain | 8q24 | gain | CEP 6 | gain | LSI 5p15 | gain | 1.000 | 0.808 | 0.808 | 0.192 | 26 |
| CEP 12 | gain | 8q24 | gain | 5 p/q imbal. | gain | LSI 5p15 | gain | 1.000 | 0.808 | 0.808 | 0.192 | 26 |
| CEP 12 | gain | 8q24 | gain | LSI 5p15 | gain | 3p14 | gain | 1.000 | 0.808 | 0.808 | 0.192 | 26 |
| CEP 12 | gain | 8q24 | gain | LSI 5p15 | gain | CEP 3 | gain | 1.000 | 0.808 | 0.808 | 0.192 | 26 |
| CEP 12 | gain | 5 p/q imbal. | gain | LSI 5q31 | gain | 3p14 | gain | 1.000 | 0.808 | 0.808 | 0.192 | 26 |
| CEP 12 | gain | 5 p/q imbal. | gain | LSI 5p15 | gain | 3p14 | gain | 1.000 | 0.808 | 0.808 | 0.192 | 26 |
| CEP 12 | gain | 5 p/q imbal. | gain | LSI 5q31 | gain | CEP 3 | gain | 1.000 | 0.808 | 0.808 | 0.192 | 26 |
| CEP 12 | gain | 5 p/q imbal. | gain | LSI 5p15 | gain | CEP 3 | gain | 1.000 | 0.808 | 0.808 | 0.192 | 26 |
| CEP 6 | gain | 5 p/q imbal. | gain | LSI 5q31 | gain | 3p14 | gain | 1.000 | 0.808 | 0.808 | 0.192 | 26 |
| CEP 6 | gain | 5 p/q imbal. | gain | LSI 5p15 | gain | 3p14 | gain | 1.000 | 0.808 | 0.808 | 0.192 | 26 |
| CEP 6 | gain | 5 p/q imbal. | gain | LSI 5q31 | gain | CEP 3 | gain | 1.000 | 0.808 | 0.808 | 0.192 | 26 |
| CEP 6 | gain | 5 p/q imbal. | gain | LSI 5p15 | gain | CEP 3 | gain | 1.000 | 0.808 | 0.808 | 0.192 | 26 |
| CEP 9 | gain | 8q24 | gain | 5 p/q imbal. | gain | LSI 5q31 | gain | 1.000 | 0.808 | 0.808 | 0.192 | 26 |
| CEP 9 | gain | 8q24 | gain | 5 p/q imbal. | gain | LSI 5p15 | gain | 1.000 | 0.808 | 0.808 | 0.192 | 26 |
| CEP 9 | gain | 8q24 | gain | LSI 5p15 | gain | 3p14 | gain | 1.000 | 0.808 | 0.808 | 0.192 | 26 |
| CEP 9 | gain | 8q24 | gain | LSI 5p15 | gain | CEP 3 | gain | 1.000 | 0.808 | 0.808 | 0.192 | 26 |
| CEP 9 | gain | 8q24 | gain | 5 p/q imbal. | gain | CEP 1 | gain | 1.000 | 0.808 | 0.808 | 0.192 | 26 |
| CEP 9 | gain | 5 p/q imbal. | gain | 3p14 | gain | | | 1.000 | 0.808 | 0.808 | 0.192 | 26 |
| CEP 9 | gain | 5 p/q imbal. | gain | LSI 5q31 | gain | CEP 3 | gain | 1.000 | 0.808 | 0.808 | 0.192 | 26 |
| CEP 9 | gain | 5 p/q imbal. | gain | LSI 5p15 | gain | CEP 3 | gain | 1.000 | 0.808 | 0.808 | 0.192 | 26 |

TABLE 8

Combinations of 2, 3 and 4 Probes at a Cutoff Value of 30%

| PROBE 1 | | PROBE 2 | | PROBE 3 | | PROBE 4 | | SPECIFICITY | SENSI- TIVITY | SENS * SPEC | VECTOR | # TUMOR SPECIMENS |
|---|---|---|---|---|---|---|---|---|---|---|---|---|
| 2 probe combinations | | | | | | | | | | | | |
| CEP 6 | gain | LSI 5p15 | gain | | | | | 1.000 | 0.692 | 0.692 | 0.308 | 26 |
| CEP 16 | gain | LSI 5p15 | gain | | | | | 1.000 | 0.684 | 0.684 | 0.316 | 19 |
| LSI 20q | gain | LSI 5p15 | gain | | | | | 1.000 | 0.684 | 0.684 | 0.316 | 19 |
| LSI 5p15 | gain | LSI 3q | gain | | | | | 1.000 | 0.684 | 0.684 | 0.316 | 19 |
| 17q21 | gain | LSI 5p15 | gain | | | | | 1.000 | 0.654 | 0.654 | 0.346 | 26 |
| 7p12 | gain | CEP 6 | gain | | | | | 1.000 | 0.654 | 0.654 | 0.346 | 26 |
| 7p12 | gain | LSI 5p15 | gain | | | | | 1.000 | 0.654 | 0.654 | 0.346 | 26 |
| CEP 7 | gain | CEP 6 | gain | | | | | 1.000 | 0.654 | 0.654 | 0.346 | 26 |
| LSI 5p15 | gain | 3p14 | gain | | | | | 1.000 | 0.654 | 0.654 | 0.346 | 26 |
| 10q23 | gain | LSI 5p15 | gain | | | | | 1.000 | 0.640 | 0.640 | 0.360 | 25 |
| CEP 10 | gain | LSI 5p15 | gain | | | | | 1.000 | 0.640 | 0.640 | 0.360 | 25 |
| LSI 5p15 | gain | CEP 4 | gain | | | | | 1.000 | 0.632 | 0.632 | 0.368 | 19 |
| LSI 5q31 | gain | LSI 3q | gain | | | | | 1.000 | 0.632 | 0.632 | 0.368 | 19 |
| 17p13 | gain | LSI 5p15 | gain | | | | | 1.000 | 0.615 | 0.615 | 0.385 | 26 |
| 8q24 | gain | LSI 5p15 | gain | | | | | 1.000 | 0.615 | 0.615 | 0.385 | 26 |
| CEP 17 | gain | LSI 5p15 | gain | | | | | 1.000 | 0.615 | 0.615 | 0.385 | 26 |
| CEP 6 | gain | CEP 1 | gain | | | | | 1.000 | 0.615 | 0.615 | 0.385 | 26 |
| CEP 6 | gain | LSI 5q31 | gain | | | | | 1.000 | 0.615 | 0.615 | 0.385 | 26 |
| CEP 7 | gain | LSI 5p15 | gain | | | | | 1.000 | 0.615 | 0.615 | 0.385 | 26 |
| CEP 8 | gain | LSI 5p15 | gain | | | | | 1.000 | 0.615 | 0.615 | 0.385 | 26 |
| LSI 13 | gain | LSI 5p15 | gain | | | | | 1.000 | 0.615 | 0.615 | 0.385 | 26 |
| LSI 5p15 | gain | CEP 1 | gain | | | | | 1.000 | 0.615 | 0.615 | 0.385 | 26 |
| LSI 5p15 | gain | CEP 3 | gain | | | | | 1.000 | 0.615 | 0.615 | 0.385 | 26 |
| CEP 18 | gain | LSI 5p15 | gain | | | | | 1.000 | 0.600 | 0.600 | 0.400 | 25 |
| 7p12 | gain | LSI 3q | gain | | | | | 1.000 | 0.579 | 0.579 | 0.421 | 19 |
| CEP 16 | gain | 7p12 | gain | | | | | 1.000 | 0.579 | 0.579 | 0.421 | 19 |
| CEP 16 | gain | LSI 5q31 | gain | | | | | 1.000 | 0.579 | 0.579 | 0.421 | 19 |
| CEP 7 | gain | LSI 3q | gain | | | | | 1.000 | 0.579 | 0.579 | 0.421 | 19 |
| LSI 20q | gain | 3p14 | gain | | | | | 1.000 | 0.579 | 0.579 | 0.421 | 19 |
| LSI 20q | gain | 7p12 | gain | | | | | 1.000 | 0.579 | 0.579 | 0.421 | 19 |
| LSI 20q | gain | CEP 12 | gain | | | | | 1.000 | 0.579 | 0.579 | 0.421 | 19 |
| LSI 20q | gain | CEP 3 | gain | | | | | 1.000 | 0.579 | 0.579 | 0.421 | 19 |

TABLE 8-continued

Combinations of 2, 3 and 4 Probes at a Cutoff Value of 30%

| PROBE 1 | | PROBE 2 | | PROBE 3 | | PROBE 4 | | SPECIFICITY | SENSI-TIVITY | SENS * SPEC | VECTOR | # TUMOR SPECIMENS |
|---|---|---|---|---|---|---|---|---|---|---|---|---|
| LSI 20q | gain | CEP 6 | gain | | | | | 1.000 | 0.579 | 0.579 | 0.421 | 19 |
| LSI 20q | gain | LSI 5q31 | gain | | | | | 1.000 | 0.579 | 0.579 | 0.421 | 19 |
| 3 probe combinations <4 and 3 pr comb (1 rat + 1 abs) | | | | | | | | | | | | |
| 8q24 | gain | 7p12 | gain | CEP 6 | gain | | | 1.000 | 0.692 | 0.692 | 0.308 | 26 |
| 8q24 | gain | CEP 6 | gain | LSI 5q31 | gain | | | 1.000 | 0.692 | 0.692 | 0.308 | 26 |
| 8q24 | gain | CEP 7 | gain | CEP 6 | gain | | | 1.000 | 0.692 | 0.692 | 0.308 | 26 |
| CEP 6 | gain | 5 p/q imbal. | gain | LSI 5q31 | gain | | | 1.000 | 0.692 | 0.692 | 0.308 | 26 |
| 5 p/q imbal. | gain | LSI 5q31 | gain | LSI 3q | gain | | | 1.000 | 0.684 | 0.684 | 0.316 | 19 |
| 8q24 | gain | LSI 5q31 | gain | LSI 3q | gain | | | 1.000 | 0.684 | 0.684 | 0.316 | 19 |
| CEP 16 | gain | 5 p/q imbal. | gain | LSI 5q31 | gain | | | 1.000 | 0.684 | 0.684 | 0.316 | 19 |
| LSI 20q | gain | 5 p/q imbal. | gain | LSI 5q31 | gain | | | 1.000 | 0.684 | 0.684 | 0.316 | 19 |
| 17p13 | gain | 8q24 | gain | LSI 5p15 | gain | | | 1.000 | 0.654 | 0.654 | 0.346 | 26 |
| 17p13 | gain | CEP 17 | gain | LSI 5p15 | gain | | | 1.000 | 0.654 | 0.654 | 0.346 | 26 |
| 17p13 | gain | CEP 7 | gain | LSI 5p15 | gain | | | 1.000 | 0.654 | 0.654 | 0.346 | 26 |
| 17p13 | gain | CEP 8 | gain | LSI 5p15 | gain | | | 1.000 | 0.654 | 0.654 | 0.346 | 26 |
| 17p13 | gain | LSI 13 | gain | LSI 5p15 | gain | | | 1.000 | 0.654 | 0.654 | 0.346 | 26 |
| 17p13 | gain | LSI 5p15 | gain | CEP 3 | gain | | | 1.000 | 0.654 | 0.654 | 0.346 | 26 |
| 17p13 | gain | LSI 5p15 | gain | CEP 1 | gain | | | 1.000 | 0.654 | 0.654 | 0.346 | 26 |
| 17p13/CEP 17 | loss | LSI 5p15 | gain | | | | | 1.000 | 0.654 | 0.654 | 0.346 | 26 |
| 17q21 | gain | 5 p/q imbal. | gain | LSI 5q31 | gain | | | 1.000 | 0.654 | 0.654 | 0.346 | 26 |
| 17q21 | gain | CEP 6 | gain | LSI 5q31 | gain | | | 1.000 | 0.654 | 0.654 | 0.346 | 26 |
| 5 p/q imbal. | gain | LSI 5q31 | gain | 3p14 | gain | | | 1.000 | 0.654 | 0.654 | 0.346 | 26 |
| 7p12 | gain | 5 p/q imbal. | gain | LSI 5q31 | gain | | | 1.000 | 0.654 | 0.654 | 0.346 | 26 |
| 7p12/CEP 7 | gain | CEP 7 | gain | LSI 5p15 | gain | | | 1.000 | 0.654 | 0.654 | 0.346 | 26 |
| 8q24 | gain | CEP 6 | gain | CEP 1 | gain | | | 1.000 | 0.654 | 0.654 | 0.346 | 26 |
| 9p21 | gain | CEP 6 | gain | CEP 1 | gain | | | 1.000 | 0.654 | 0.654 | 0.346 | 26 |
| CEP 12 | gain | CEP 6 | gain | CEP 1 | gain | | | 1.000 | 0.654 | 0.654 | 0.346 | 26 |
| CEP 12 | gain | CEP 6 | gain | LSI 5q31 | gain | | | 1.000 | 0.654 | 0.654 | 0.346 | 26 |
| CEP 17 | gain | CEP 6 | gain | LSI 5q31 | gain | | | 1.000 | 0.654 | 0.654 | 0.346 | 26 |
| CEP 6 | gain | LSI 5q31 | gain | CEP 3 | gain | | | 1.000 | 0.654 | 0.654 | 0.346 | 26 |
| CEP 6 | gain | LSI 5q31 | gain | CEP 1 | gain | | | 1.000 | 0.654 | 0.654 | 0.346 | 26 |
| CEP 8 | gain | CEP 6 | gain | LSI 5q31 | gain | | | 1.000 | 0.654 | 0.654 | 0.346 | 26 |
| CEP 9 | gain | CEP 6 | gain | CEP 1 | gain | | | 1.000 | 0.654 | 0.654 | 0.346 | 26 |
| 10q23 | gain | 5 p/q imbal. | gain | LSI 5q31 | gain | | | 1.000 | 0.640 | 0.640 | 0.360 | 25 |
| CEP 10 | gain | 5 p/q imbal. | gain | LSI 5q31 | gain | | | 1.000 | 0.640 | 0.640 | 0.360 | 25 |
| CEP 18 | gain | 17p13 | gain | LSI 5p15 | gain | | | 1.000 | 0.640 | 0.640 | 0.360 | 25 |
| 4 probe combinations <4 and 4 pr comb (1 rat + 2 abs) | | | | | | | | | | | | |
| 17p13/CEP 17 | loss | CEP 6 | gain | LSI 5p15 | gain | | | 1.000 | 0.731 | 0.731 | 0.269 | 26 |
| 17p13/CEP 17 | loss | CEP 6 | gain | LSI 5q31 | gain | | | 1.000 | 0.692 | 0.692 | 0.308 | 26 |
| 17p13/CEP 17 | loss | CEP 7 | gain | CEP 6 | gain | | | 1.000 | 0.692 | 0.692 | 0.308 | 26 |
| 7p12 | gain | CEP 6 | gain | 5 p/q imbal. | gain | | | 1.000 | 0.692 | 0.692 | 0.308 | 26 |
| 9p21 | gain | 8q24 | gain | CEP 6 | gain | CEP 1 | gain | 1.000 | 0.692 | 0.692 | 0.308 | 26 |
| CEP 7 | gain | CEP 6 | gain | 5 p/q imbal. | gain | | | 1.000 | 0.692 | 0.692 | 0.308 | 26 |
| CEP 9 | gain | 8q24 | gain | CEP 6 | gain | CEP 1 | gain | 1.000 | 0.692 | 0.692 | 0.308 | 26 |
| 8q24 | gain | 7p12 | gain | LSI 3q | gain | 3p14 | gain | 1.000 | 0.684 | 0.684 | 0.316 | 19 |
| 8q24 | gain | 7p12 | gain | LSI 3q | gain | CEP 3 | gain | 1.000 | 0.684 | 0.684 | 0.316 | 19 |
| 8q24 | gain | CEP 7 | gain | LSI 3q | gain | 3p14 | gain | 1.000 | 0.684 | 0.684 | 0.316 | 19 |
| 8q24 | gain | CEP 7 | gain | LSI 3q | gain | CEP 3 | gain | 1.000 | 0.684 | 0.684 | 0.316 | 19 |
| CEP 12 | gain | 8q24 | gain | 7p12 | gain | LSI 3q | gain | 1.000 | 0.684 | 0.684 | 0.316 | 19 |
| CEP 12 | gain | 8q24 | gain | CEP 7 | gain | LSI 3q | gain | 1.000 | 0.684 | 0.684 | 0.316 | 19 |
| CEP 16 | gain | 8q24 | gain | 7p12 | gain | LSI 5q31 | gain | 1.000 | 0.684 | 0.684 | 0.316 | 19 |
| CEP 16 | gain | 8q24 | gain | 7p12 | gain | 3p14 | gain | 1.000 | 0.684 | 0.684 | 0.316 | 19 |
| CEP 16 | gain | 8q24 | gain | CEP 7 | gain | 3p14 | gain | 1.000 | 0.684 | 0.684 | 0.316 | 19 |
| CEP 16 | gain | 8q24 | gain | LSI 5q31 | gain | 3p14 | gain | 1.000 | 0.684 | 0.684 | 0.316 | 19 |
| CEP 16 | gain | 8q24 | gain | 7p12 | gain | CEP 3 | gain | 1.000 | 0.684 | 0.684 | 0.316 | 19 |
| CEP 16 | gain | 8q24 | gain | CEP 7 | gain | CEP 3 | gain | 1.000 | 0.684 | 0.684 | 0.316 | 19 |
| CEP 16 | gain | 8q24 | gain | LSI 5q31 | gain | CEP 3 | gain | 1.000 | 0.684 | 0.684 | 0.316 | 19 |
| CEP 16 | gain | CEP 11 | gain | 8q24 | gain | LSI 5q31 | gain | 1.000 | 0.684 | 0.684 | 0.316 | 19 |
| CEP 16 | gain | CEP 12 | gain | 8q24 | gain | 7p12 | gain | 1.000 | 0.684 | 0.684 | 0.316 | 19 |
| CEP 16 | gain | CEP 12 | gain | 8q24 | gain | CEP 7 | gain | 1.000 | 0.684 | 0.684 | 0.316 | 19 |
| CEP 16 | gain | CEP 12 | gain | 8q24 | gain | LSI 5q31 | gain | 1.000 | 0.684 | 0.684 | 0.316 | 19 |
| LSI 20q | gain | 8q24 | gain | 7p12 | gain | LSI 5q31 | gain | 1.000 | 0.684 | 0.684 | 0.316 | 19 |
| LSI 20q | gain | 8q24 | gain | 7p12 | gain | 3p14 | gain | 1.000 | 0.684 | 0.684 | 0.316 | 19 |
| LSI 20q | gain | 8q24 | gain | CEP 7 | gain | 3p14 | gain | 1.000 | 0.684 | 0.684 | 0.316 | 19 |
| LSI 20q | gain | 8q24 | gain | LSI 5q31 | gain | 3p14 | gain | 1.000 | 0.684 | 0.684 | 0.316 | 19 |
| LSI 20q | gain | 8q24 | gain | 7p12 | gain | CEP 3 | gain | 1.000 | 0.684 | 0.684 | 0.316 | 19 |
| LSI 20q | gain | 8q24 | gain | CEP 7 | gain | CEP 3 | gain | 1.000 | 0.684 | 0.684 | 0.316 | 19 |
| LSI 20q | gain | 8q24 | gain | LSI 5q31 | gain | CEP 3 | gain | 1.000 | 0.684 | 0.684 | 0.316 | 19 |
| LSI 20q | gain | 9p21 | gain | 8q24 | gain | CEP 6 | gain | 1.000 | 0.684 | 0.684 | 0.316 | 19 |

TABLE 8-continued

Combinations of 2, 3 and 4 Probes at a Cutoff Value of 30%

| PROBE 1 | | PROBE 2 | | PROBE 3 | | PROBE 4 | | SPECIFICITY | SENSI-TIVITY | SENS * SPEC | VECTOR | # TUMOR SPECIMENS |
|---|---|---|---|---|---|---|---|---|---|---|---|---|
| LSI 20q | gain | 9p21 | gain | 8q24 | gain | 3p14 | gain | 1.000 | 0.684 | 0.684 | 0.316 | 19 |
| LSI 20q | gain | 9p21 | gain | 8q24 | gain | CEP 3 | gain | 1.000 | 0.684 | 0.684 | 0.316 | 19 |
| LSI 20q | gain | CEP 11 | gain | 8q24 | gain | LSI 5q31 | gain | 1.000 | 0.684 | 0.684 | 0.316 | 19 |
| LSI 20q | gain | CEP 12 | gain | 9p21 | gain | 8q24 | gain | 1.000 | 0.684 | 0.684 | 0.316 | 19 |
| LSI 20q | gain | CEP 12 | gain | CEP 9 | gain | 8q24 | gain | 1.000 | 0.684 | 0.684 | 0.316 | 19 |
| LSI 20q | gain | CEP 12 | gain | 8q24 | gain | 7p12 | gain | 1.000 | 0.684 | 0.684 | 0.316 | 19 |
| LSI 20q | gain | CEP 12 | gain | 8q24 | gain | CEP 7 | gain | 1.000 | 0.684 | 0.684 | 0.316 | 19 |
| LSI 20q | gain | CEP 12 | gain | 8q24 | gain | LSI 5q31 | gain | 1.000 | 0.684 | 0.684 | 0.316 | 19 |
| LSI 20q | gain | CEP 9 | gain | 8q24 | gain | CEP 6 | gain | 1.000 | 0.684 | 0.684 | 0.316 | 19 |
| LSI 20q | gain | CEP 9 | gain | 8q24 | gain | 3p14 | gain | 1.000 | 0.684 | 0.684 | 0.316 | 19 |
| LSI 20q | gain | CEP 9 | gain | 8q24 | gain | CEP 3 | gain | 1.000 | 0.684 | 0.684 | 0.316 | 19 |

TABLE 9

Combinations of 2, 3 and 4 Probes at a Cutoff Value of 40%

| PROBE 1 | | PROBE 2 | | PROBE 3 | | PROBE 4 | | SPECI-FICITY | SENSITIVIT | SENS * SPEC | VECTOR | # TUMOR SPECIMENS |
|---|---|---|---|---|---|---|---|---|---|---|---|---|
| | | | | | | 2 probe combinations | | | | | | |
| 7p12 | gain | LSI 3q | gain | | | | | 1.000 | 0.579 | 0.579 | 0.421 | 19 |
| 7p12 | gain | CEP 6 | gain | | | | | 1.000 | 0.538 | 0.538 | 0.462 | 26 |
| LSI 3q | gain | CEP 1 | gain | | | | | 1.000 | 0.526 | 0.526 | 0.474 | 19 |
| CEP 6 | gain | CEP 1 | gain | | | | | 1.000 | 0.500 | 0.500 | 0.500 | 26 |
| CEP 7 | gain | CEP 6 | gain | | | | | 1.000 | 0.500 | 0.500 | 0.500 | 26 |
| CEP 18 | gain | 7p12 | gain | | | | | 1.000 | 0.480 | 0.480 | 0.520 | 25 |
| 7p12 | gain | CEP 4 | gain | | | | | 1.000 | 0.474 | 0.474 | 0.526 | 19 |
| CEP 16 | gain | 7p12 | gain | | | | | 1.000 | 0.474 | 0.474 | 0.526 | 19 |
| CEP 7 | gain | LSI 3q | gain | | | | | 1.000 | 0.474 | 0.474 | 0.526 | 19 |
| LSI 20q | gain | 7p12 | gain | | | | | 1.000 | 0.474 | 0.474 | 0.526 | 19 |
| LSI 5p15 | gain | LSI 3q | gain | | | | | 1.000 | 0.474 | 0.474 | 0.526 | 19 |
| 7p12 | gain | LSI 5p15 | gain | | | | | 1.000 | 0.462 | 0.462 | 0.538 | 26 |
| CEP 10 | gain | 7p12 | gain | | | | | 1.000 | 0.440 | 0.440 | 0.560 | 25 |
| CEP 18 | gain | CEP 1 | gain | | | | | 1.000 | 0.440 | 0.440 | 0.560 | 25 |
| 7p12 | gain | LSI 5q31 | gain | | | | | 1.000 | 0.423 | 0.423 | 0.577 | 26 |
| CEP 11 | gain | 7p12 | gain | | | | | 1.000 | 0.423 | 0.423 | 0.577 | 26 |
| CEP 6 | gain | LSI 5p15 | gain | | | | | 1.000 | 0.423 | 0.423 | 0.577 | 26 |
| CEP 7 | gain | LSI 5p15 | gain | | | | | 1.000 | 0.423 | 0.423 | 0.577 | 26 |
| LSI 5p15 | gain | CEP 1 | gain | | | | | 1.000 | 0.423 | 0.423 | 0.577 | 26 |
| CEP 16 | gain | CEP 1 | gain | | | | | 1.000 | 0.421 | 0.421 | 0.579 | 19 |
| CEP 16 | gain | CEP 7 | gain | | | | | 1.000 | 0.421 | 0.421 | 0.579 | 19 |
| CEP 4 | gain | CEP 1 | gain | | | | | 1.000 | 0.421 | 0.421 | 0.579 | 19 |
| LSI 20q | gain | CEP 1 | gain | | | | | 1.000 | 0.421 | 0.421 | 0.579 | 19 |
| LSI 20q | gain | CEP 7 | gain | | | | | 1.000 | 0.421 | 0.421 | 0.579 | 19 |
| 10q23 | gain | 7p12 | gain | | | | | 1.000 | 0.400 | 0.400 | 0.600 | 25 |
| CEP 10 | gain | CEP 1 | gain | | | | | 1.000 | 0.400 | 0.400 | 0.600 | 25 |
| CEP 18 | gain | CEP 7 | gain | | | | | 1.000 | 0.400 | 0.400 | 0.600 | 25 |
| CEP 11 | gain | CEP 1 | gain | | | | | 1.000 | 0.385 | 0.385 | 0.615 | 26 |
| CEP 11 | gain | CEP 7 | gain | | | | | 1.000 | 0.385 | 0.385 | 0.615 | 26 |
| CEP 12 | gain | CEP 6 | gain | | | | | 1.000 | 0.385 | 0.385 | 0.615 | 26 |
| | | | | | | 3 probe combinations | | | | | | |
| CEP 11 | gain | 7p12 | gain | CEP 6 | gain | | | 1.000 | 0.577 | 0.577 | 0.423 | 26 |
| CEP 11 | gain | CEP 6 | gain | CEP 1 | gain | | | 1.000 | 0.538 | 0.538 | 0.462 | 26 |
| CEP 11 | gain | CEP 7 | gain | CEP 6 | gain | | | 1.000 | 0.538 | 0.538 | 0.462 | 26 |
| 17q21 | gain | CEP 7 | gain | LSI 3q | gain | | | 1.000 | 0.526 | 0.526 | 0.474 | 19 |
| CEP 11 | gain | 7p12 | gain | CEP 4 | gain | | | 1.000 | 0.526 | 0.526 | 0.474 | 19 |
| CEP 11 | gain | CEP 7 | gain | LSI 3q | gain | | | 1.000 | 0.526 | 0.526 | 0.474 | 19 |
| CEP 16 | gain | CEP 11 | gain | 7p12 | gain | | | 1.000 | 0.526 | 0.526 | 0.474 | 19 |
| CEP 16 | gain | CEP 7 | gain | LSI 3q | gain | | | 1.000 | 0.526 | 0.526 | 0.474 | 19 |
| CEP 7 | gain | CEP 6 | gain | LSI 3q | gain | | | 1.000 | 0.526 | 0.526 | 0.474 | 19 |
| CEP 7 | gain | LSI 5p15 | gain | LSI 3q | gain | | | 1.000 | 0.526 | 0.526 | 0.474 | 19 |
| LSI 20q | gain | CEP 11 | gain | 7p12 | gain | | | 1.000 | 0.526 | 0.526 | 0.474 | 19 |
| LSI 20q | gain | CEP 7 | gain | LSI 3q | gain | | | 1.000 | 0.526 | 0.526 | 0.474 | 19 |
| CEP 18 | gain | 10q23 | gain | 7p12 | gain | | | 1.000 | 0.520 | 0.520 | 0.480 | 25 |
| CEP 18 | gain | CEP 10 | gain | 7p12 | gain | | | 1.000 | 0.520 | 0.520 | 0.480 | 25 |
| CEP 18 | gain | CEP 6 | gain | CEP 1 | gain | | | 1.000 | 0.520 | 0.520 | 0.480 | 25 |
| CEP 18 | gain | CEP 7 | gain | CEP 6 | gain | | | 1.000 | 0.520 | 0.520 | 0.480 | 25 |
| CEP 11 | gain | 7p12 | gain | LSI 5p15 | gain | | | 1.000 | 0.500 | 0.500 | 0.500 | 26 |
| CEP 18 | gain | 7p12 | gain | CEP 4 | gain | | | 1.000 | 0.500 | 0.500 | 0.500 | 18 |
| CEP 18 | gain | CEP 16 | gain | 7p12 | gain | | | 1.000 | 0.500 | 0.500 | 0.500 | 18 |

TABLE 9-continued

Combinations of 2, 3 and 4 Probes at a Cutoff Value of 40%

| PROBE 1 | | PROBE 2 | | PROBE 3 | | PROBE 4 | | SPECI-FICITY | SENSITIVIT | SENS * SPEC | VECTOR | # TUMOR SPECIMENS |
|---|---|---|---|---|---|---|---|---|---|---|---|---|
| LSI 20q | gain | CEP 18 | gain | 7p12 | gain | | | 1.000 | 0.500 | 0.500 | 0.500 | 18 |
| 10q23 | gain | 7p12 | gain | LSI 5p15 | gain | | | 1.000 | 0.480 | 0.480 | 0.520 | 25 |
| CEP 10 | gain | 7p12 | gain | LSI 5p15 | gain | | | 1.000 | 0.480 | 0.480 | 0.520 | 25 |
| CEP 11 | gain | CEP 10 | gain | 7p12 | gain | | | 1.000 | 0.480 | 0.480 | 0.520 | 25 |
| CEP 18 | gain | 10q23 | gain | CEP 1 | gain | | | 1.000 | 0.480 | 0.480 | 0.520 | 25 |
| CEP 18 | gain | CEP 10 | gain | CEP 1 | gain | | | 1.000 | 0.480 | 0.480 | 0.520 | 25 |
| CEP 11 | gain | CEP 4 | gain | CEP 1 | gain | | | 1.000 | 0.474 | 0.474 | 0.526 | 19 |
| CEP 11 | gain | CEP 7 | gain | CEP 4 | gain | | | 1.000 | 0.474 | 0.474 | 0.526 | 19 |
| CEP 16 | gain | CEP 11 | gain | CEP 7 | gain | | | 1.000 | 0.474 | 0.474 | 0.526 | 19 |
| CEP 16 | gain | CEP 11 | gain | CEP 1 | gain | | | 1.000 | 0.474 | 0.474 | 0.526 | 19 |
| LSI 20q | gain | CEP 11 | gain | CEP 7 | gain | | | 1.000 | 0.474 | 0.474 | 0.526 | 19 |
| LSI 20q | gain | CEP 11 | gain | CEP 1 | gain | | | 1.000 | 0.474 | 0.474 | 0.526 | 19 |
| | | | | 4 probe combinations | | | | | | | | |
| 17p13/CEP 17 | loss | CEP 6 | gain | CEP 1 | gain | | | 1.000 | 0.538 | 0.538 | 0.462 | 26 |
| 17p13/CEP 17 | loss | CEP 7 | gain | CEP 6 | gain | | | 1.000 | 0.538 | 0.538 | 0.462 | 26 |
| 9p21/CEP 9 | loss | CEP 7 | gain | LSI 3q | gain | | | 1.000 | 0.526 | 0.526 | 0.474 | 19 |
| CEP 11 | gain | 10q23 | gain | 7p12 | gain | LSI 5p15 | gain | 1.000 | 0.520 | 0.520 | 0.480 | 25 |
| CEP 11 | gain | CEP 10 | gain | 7p12 | gain | LSI 5q31 | gain | 1.000 | 0.520 | 0.520 | 0.480 | 25 |
| CEP 11 | gain | 7p12 | gain | 5 p/q imbal. | gain | | | 1.000 | 0.500 | 0.500 | 0.500 | 26 |
| CEP 11 | gain | CEP 9 | gain | CEP 6 | gain | LSI 5p15 | gain | 1.000 | 0.500 | 0.500 | 0.500 | 26 |
| 10q23 | gain | 7p12 | gain | 5 p/q imbal. | gain | | | 1.000 | 0.480 | 0.480 | 0.520 | 25 |
| CEP 10 | gain | 7p12 | gain | 5 p/q imbal. | gain | | | 1.000 | 0.480 | 0.480 | 0.520 | 25 |
| CEP 11 | gain | 10q23 | gain | 7p12 | gain | LSI 5q31 | gain | 1.000 | 0.480 | 0.480 | 0.520 | 25 |
| CEP 11 | gain | 10q23 | gain | CEP 7 | gain | LSI 5p15 | gain | 1.000 | 0.480 | 0.480 | 0.520 | 25 |
| CEP 11 | gain | 10q23 | gain | LSI 5p15 | gain | CEP 1 | gain | 1.000 | 0.480 | 0.480 | 0.520 | 25 |
| CEP 11 | gain | CEP 10 | gain | CEP 7 | gain | LSI 5q31 | gain | 1.000 | 0.480 | 0.480 | 0.520 | 25 |
| CEP 11 | gain | CEP 10 | gain | LSI 5q31 | gain | CEP 1 | gain | 1.000 | 0.480 | 0.480 | 0.520 | 25 |
| CEP 11 | gain | CEP 10 | gain | LSI 5p15 | gain | CEP 1 | gain | 1.000 | 0.480 | 0.480 | 0.520 | 25 |
| CEP 11 | gain | CEP 10 | gain | CEP 7 | gain | LSI 5q31 | gain | 1.000 | 0.480 | 0.480 | 0.520 | 25 |
| CEP 11 | gain | CEP 10 | gain | CEP 7 | gain | LSI 5p15 | gain | 1.000 | 0.480 | 0.480 | 0.520 | 25 |
| CEP 18 | gain | 10q23 | gain | CEP 7 | gain | LSI 5p15 | gain | 1.000 | 0.480 | 0.480 | 0.520 | 25 |
| CEP 18 | gain | 17p13 | gain | 10q23 | gain | CEP 7 | gain | 1.000 | 0.480 | 0.480 | 0.520 | 25 |
| CEP 18 | gain | 17p13 | gain | CEP 10 | gain | CEP 7 | gain | 1.000 | 0.480 | 0.480 | 0.520 | 25 |
| CEP 18 | gain | 17p13/CEP 17 | loss | CEP 1 | gain | | | 1.000 | 0.480 | 0.480 | 0.520 | 25 |
| CEP 18 | gain | 17q21 | gain | 10q23 | gain | CEP 7 | gain | 1.000 | 0.480 | 0.480 | 0.520 | 25 |
| CEP 18 | gain | 17q21 | gain | CEP 10 | gain | CEP 7 | gain | 1.000 | 0.480 | 0.480 | 0.520 | 25 |
| CEP 18 | gain | CEP 10 | gain | CEP 7 | gain | LSI 5p15 | gain | 1.000 | 0.480 | 0.480 | 0.520 | 25 |
| CEP 18 | gain | CEP 11 | gain | 10q23 | gain | CEP 7 | gain | 1.000 | 0.480 | 0.480 | 0.520 | 25 |
| CEP 18 | gain | CEP 11 | gain | CEP 10 | gain | CEP 7 | gain | 1.000 | 0.480 | 0.480 | 0.520 | 25 |
| CEP 18 | gain | CEP 9 | gain | CEP 6 | gain | LSI 5p15 | gain | 1.000 | 0.480 | 0.480 | 0.520 | 25 |
| 17p13/CEP 17 | loss | CEP 6 | gain | LSI 5p15 | gain | | | 1.000 | 0.462 | 0.462 | 0.538 | 26 |
| 17p13/CEP 17 | loss | CEP 7 | gain | LSI 5p15 | gain | | | 1.000 | 0.462 | 0.462 | 0.538 | 26 |
| 17p13/CEP 17 | loss | LSI 5p15 | gain | CEP 1 | gain | | | 1.000 | 0.462 | 0.462 | 0.538 | 26 |
| 9p21/CEP 9 | loss | CEP 6 | gain | LSI 5p15 | gain | | | 1.000 | 0.462 | 0.462 | 0.538 | 26 |
| CEP 11 | gain | 5 p/q imbal. | gain | CEP 1 | gain | | | 1.000 | 0.462 | 0.462 | 0.538 | 26 |
| CEP 11 | gain | CEP 7 | gain | 5 p/q imbal. | gain | | | 1.000 | 0.462 | 0.462 | 0.538 | 26 |
| CEP 12 | gain | CEP 11 | gain | CEP 9 | gain | CEP 6 | gain | 1.000 | 0.462 | 0.462 | 0.538 | 26 |

TABLE 10

Analysis of Bronchial Secretions from 21 Patients by Cytology, Bronchus Biopsy, and FISH

| | | Cytology | | | FISH Result | |
|---|---|---|---|---|---|---|
| Specimen I.D. | Clinical Diagnosis | Result | Bronchus Biopsy | Additional Biopsy | Probes Indicating Gain | FISH Diagnosis |
| #3935 | Small Cell CA | positive | positive | not done | LSI 5p15 | positive |
| #3912 | Squamous Cell CA | positive | positive | not done | LSI 8q24, LSI 5p15, CEP 1 CEP 6 | positive |
| #3911 | Squamous Cell CA | positive | positive | not done | LSI 8q24, LSI 5p15, CEP 1 CEP 6 | positive |
| #2870 | Mesenchymal CA | negative | negative | positive | LSI 5p15, CEP 6 | positive |
| #30582 | Adenocarcinoma | positive | not done | not done | LSI 8q24, LSI 5p15, CEP 1 CEP 6 | positive |
| #1995 | Breast CA metastasis | positive | positive | positive | LSI 8q24, LSI 5p15, CEP 1 CEP 6 | positive |
| #2786 | Large Cell CA | negative | negative | positive | none | negative |
| #2789 | No malignancy | negative | negative | not done | none | negative |
| #2545 | Small Cell CA | positive | positive | not done | LSI 8q24, LSI 5p15, CEP 1 | positive |
| #3700 | Adenocarcinoma | positive | positive | not done | LSI 8q24, LSI 5p15 | positive |
| #2363 | Large Cell CA | positive | positive | not done | LSI 8q24, LSI 5p15, CEP 1 | positive |
| #3739 | Squamous Cell CA | positive | positive | not done | LSI 8q24, LSI 5p15, CEP 1 | positive |
| #30796 | Small Cell CA | positive | positive | not done | LSI 8q24, LSI 5p15 | positive |
| #30671 | Adenocarcinoma | positive | negative | positive | LSI 8q24, LSI 5p15 | positive |
| #1864 | Breast CA metastasis | positive | negative | positive | LSI 8q24, LSI 5p15 | positive |

TABLE 10-continued

Analysis of Bronchial Secretions from 21 Patients by Cytology, Bronchus Biopsy, and FISH

| | | Cytology | | | FISH Result | |
|---|---|---|---|---|---|---|
| Specimen I.D. | Clinical Diagnosis | Result | Bronchus Biopsy | Additional Biopsy | Probes Indicating Gain | FISH Diagnosis |
| #2546 | Large Cell CA | negative | not done | positive | — | not evaluated* |
| #2577 | No malignancy | negative | negative | not done | none | negative |
| #2251 | No malignancy | negative | not done | negative | none | negative |
| #2603 | No malignancy | negative | negative | not done | none | negative |
| #2785 | No malignancy | negative | negative | pos for epipharynx CA | none | negative |
| #30706 | Equivocal | negative | Not done | Equivocal | none | negative |

*cell morphology was too poor to permit evaluation.

TABLE 11

Conventional Cytology Performance Compared to Clinical Diagnosis

| Cytology | Clinical Diagnosis | |
|---|---|---|
| Result | negative | positive/equivocal |
| negative | 5 | 4 |
| positive | 0 | 12 | specificity = 100%
sensitivity = 75%
sensitivity = 80% excluding the slide not evaluated by FISH

TABLE 12

FISH Performance Compared to Clinical Diagnosis

| FISH | Clinical Diagnosis | |
|---|---|---|
| Result | negative | positive/equivocal |
| negative | 5 | 2 |
| positive | 0 | 13 |
| not evaluated | 0 | 1 | specificity = 100%
sensitivity = 81% including non-evaluable FISH slide
sensitivity = 87% excluding non-evaluable FISH slide

TABLE 13

Probe Sets Based on Discriminate and Combinatorial Analyses

| | | | | VECTOR VALUE | | | | |
|---|---|---|---|---|---|---|---|---|
| PROBE 1 | PROBE 2 | PROBE 3 | PROBE 4 | CUTOFF = 5 | CUTOFF = 10 | CUTOFF = 20 | CUTOFF = 3 | CUTOFF = 40 |
| Single probes: | | | | | | | | |
| LSI 5p15 | | | | 0.407 | 0.231 | 0.346 | 0.423 | 0.692 |
| CEP 1 | | | | 0.077 | 0.346 | 0.462 | 0.615 | 0.654 |
| CEP 6 | | | | 0.287 | 0.385 | 0.500 | 0.500 | 0.692 |
| LSI 7p12 | | | | 0.619 | 0.324 | 0.385 | 0.500 | 0.615 |
| LSI 8q24 | | | | 0.210 | 0.222 | 0.556 | 0.778 | 0.889 |
| CEP 9 | | | | 0.287 | 0.346 | 0.577 | 0.808 | 0.885 |
| 2 Probe combinations: | | | | | | | | |
| LSI 5p15 | LSI 8q24 | | | | 0.154 | 0.269 | 0.385 | |
| LSI 5p15 | LSI 3q | | | | | 0.211 | 0.316 | 0.526 |
| LSI 5p15 | LSI 20q | | | | | 0.263 | 0.316 | |
| LSI 5p15 | LSI 7p12 | | | | | 0.308 | 0.346 | 0.538 |
| LSI 5p15 | CEP 16 | | | | | 0.263 | 0.316 | |
| LSI 5p15 | CEP 4 | | | | | 0.263 | 0.368 | |
| LSI 5p15 | CEP 12 | | | | 0.154 | 0.308 | 0.368 | |
| LSI 5p15 | CEP 6 | | | | | 0.269 | 0.308 | 0.577 |
| LSI 5p15 | LSI 17q21 | | | | 0.192 | 0.269 | 0.346 | |
| LSI 8q24 | CEP 17 | | | | 0.148 | | | |
| LSI 8q24 | CEP 1 | | | | 0.154 | | | |
| LSI 8q24 | CEP 6 | | | | 0.192 | 0.308 | | |
| LSI 7p12 | LSI 3q | | | | | 0.316 | 0.421 | 0.421 |
| LSI 7p12 | CEP 6 | | | | | | 0.346 | 0.462 |
| LSI 3q | CEP 7 | | | | | 0.316 | 0.421 | 0.526 |
| CEP 6 | CEP 7 | | | | | | 0.346 | 0.500 |
| 3 Probe combinations: | | | | | | | | |
| LSI 5p15 | LSI 8q24 | LSI 9p21 | | | 0.115 | | | |
| LSI 5p15 | CEP 12 | LSI 9p21 | | | 0.115 | | | |
| LSI 8q24 | CEP 17 | LSI 9p21 | | | 0.115 | | | |
| LSI 8q24 | CEP 1 | LSI 9p21 | | | 0.115 | | | |
| LSI 5p15 | LSI 3q | CEP 12 | | | | | 0.158 | |
| 4 Probe combinations: | | | | | | | | |
| LSI 5p15 | CEP 6 | LSI 17p13 (loss) | CEP 17 | | 0.269 | | | |

TABLE 13-continued

Probe Sets Based on Discriminate and Combinatorial Analyses

| | | | | VECTOR VALUE | | | | |
|---|---|---|---|---|---|---|---|---|
| PROBE 1 | PROBE 2 | PROBE 3 | PROBE 4 | CUTOFF = 5 | CUTOFF = 10 | CUTOFF = 20 | CUTOFF = 3 | CUTOFF = 40 |

Probe sets with redundant complementation:
3 probe combinations (sum of 2 probe pairs with 1 probe in common):

| PROBE 1 | PROBE 2 | PROBE 3 |
|---|---|---|
| LSI 5p15 | LSI 8q24 | LSI 3q |
| LSI 5p15 | LSI 8q24 | LSI 20q |
| LSI 5p15 | LSI 8q24 | LSI 7p12 |
| LSI 5p15 | LSI 8q24 | CEP 16 |
| LSI 5p15 | LSI 8q24 | CEP 4 |
| LSI 5p15 | LSI 8q24 | CEP 12 |
| LSI 5p15 | LSI 8q24 | CEP 6 |
| LSI 5p15 | LSI 8q24 | LSI 17q21 |
| LSI 5p15 | LSI 8q24 | CEP 17 |
| LSI 5p15 | LSI 8q24 | CEP 1 |
| LSI 5p15 | LSI 3q | LSI 20q |
| LSI 5p15 | LSI 3q | LSI 7p12 |
| LSI 5p15 | LSI 3q | CEP 16 |
| LSI 5p15 | LSI 3q | CEP 4 |
| LSI 5p15 | LSI 3q | CEP 12 |
| LSI 5p15 | LSI 3q | CEP 6 |
| LSI 5p15 | LSI 3q | LSI 17q21 |
| LSI 5p15 | LSI 3q | CEP 7 |
| LSI 5p15 | LSI 3q | LSI 7p12 |
| LSI 5p15 | LSI 20q | LSI 7p12 |
| LSI 5p15 | LSI 20q | CEP 16 |
| LSI 5p15 | LSI 20q | CEP 4 |
| LSI 5p15 | LSI 20q | CEP 12 |
| LSI 5p15 | LSI 20q | CEP 6 |
| LSI 5p15 | LSI 20q | LSI 17q21 |
| LSI 5p15 | LSI 7p12 | CEP 16 |
| LSI 5p15 | LSI 7p12 | CEP 4 |
| LSI 5p15 | LSI 7p12 | CEP 12 |
| LSI 5p15 | LSI 7p12 | CEP 6 |
| LSI 5p15 | LSI 7p12 | LSI 17q21 |
| LSI 5p15 | LSI 7p12 | LSI 3q |
| LSI 5p15 | LSI 7p12 | CEP 6 |
| LSI 5p15 | CEP 16 | CEP 4 |
| LSI 5p15 | CEP 16 | CEP 12 |
| LSI 5p15 | CEP 16 | CEP 6 |
| LSI 5p15 | CEP 16 | LSI 17q21 |
| LSI 5p15 | CEP 4 | CEP 12 |
| LSI 5p15 | CEP 4 | CEP 6 |
| LSI 5p15 | CEP 4 | LSI 17q21 |
| LSI 5p15 | CEP 12 | CEP 6 |
| LSI 5p15 | CEP 12 | LSI 17q21 |
| LSI 5p15 | CEP 6 | LSI 17q21 |
| LSI 5p15 | CEP 6 | CEP 7 |
| LSI 8q24 | CEP 17 | CEP 1 |
| LSI 8q24 | CEP 17 | CEP 6 |
| LSI 8q24 | CEP 1 | CEP 6 |
| LSI 8q24 | LSI 7p12 | CEP 6 |
| LSI 8q24 | CEP 6 | CEP 7 |
| LSI 7p12 | LSI 3q | CEP 6 |
| LSI 7p12 | LSI 3q | CEP 7 |
| LSI 7p12 | CEP 6 | CEP 7 |
| LSI 3q | CEP 6 | CEP 7 |

4 probe combinations - 2 redundant complementary pairs:

| PROBE 1 | PROBE 2 | PROBE 3 | PROBE 4 |
|---|---|---|---|
| LSI 5p15 | LSI 8q24 | 7p12 | LSI 3q |
| LSI 5p15 | LSI 8q24 | 7p12 | CEP 6 |
| LSI 5p15 | LSI 8q24 | LSI 3q | CEP 7 |
| LSI 5p15 | LSI 8q24 | CEP 6 | CEP 7 |
| LSI 5p15 | LSI 3q | 8q24 | CEP 17 |
| LSI 5p15 | LSI 3q | 8q24 | CEP 1 |
| LSI 5p15 | LSI 3q | 8q24 | CEP 6 |
| LSI 5p15 | LSI 3q | 7p12 | CEP 6 |
| LSI 5p15 | LSI 3q | CEP 6 | CEP 7 |
| LSI 5p15 | LSI 20q | 8q24 | CEP 17 |
| LSI 5p15 | LSI 20q | 8q24 | CEP 1 |
| LSI 5p15 | LSI 20q | 8q24 | CEP 6 |
| LSI 5p15 | LSI 20q | 7p12 | LSI 3q |
| LSI 5p15 | LSI 20q | 7p12 | CEP 6 |
| LSI 5p15 | LSI 20q | LSI 3q | CEP 7 |
| LSI 5p15 | LSI 20q | CEP 6 | CEP 7 |
| LSI 5p15 | 7p12 | 8q24 | CEP 17 |

TABLE 13-continued

Probe Sets Based on Discriminate and Combinatorial Analyses

| | | | | VECTOR VALUE | | | | |
|---|---|---|---|---|---|---|---|---|
| PROBE 1 | PROBE 2 | PROBE 3 | PROBE 4 | CUTOFF = 5 | CUTOFF = 10 | CUTOFF = 20 | CUTOFF = 3 | CUTOFF = 40 |
| LSI 5p15 | 7p12 | 8q24 | CEP 1 | | | | | |
| LSI 5p15 | 7p12 | 8q24 | CEP 6 | | | | | |
| LSI 5p15 | 7p12 | LSI 3q | CEP 7 | | | | | |
| LSI 5p15 | 7p12 | CEP 6 | CEP 7 | | | | | |
| LSI 5p15 | CEP 16 | LSI 8q24 | CEP 17 | | | | | |
| LSI 5p15 | CEP 16 | LSI 8q24 | CEP 1 | | | | | |
| LSI 5p15 | CEP 16 | LSI 8q24 | CEP 6 | | | | | |
| LSI 5p15 | CEP 16 | LSI 7p12 | LSI 3q | | | | | |
| LSI 5p15 | CEP 16 | LSI 7p12 | CEP 6 | | | | | |
| LSI 5p15 | CEP 16 | LSI 3q | CEP 7 | | | | | |
| LSI 5p15 | CEP 16 | CEP 6 | CEP 7 | | | | | |
| LSI 5p15 | CEP 4 | LSI 8q24 | CEP 17 | | | | | |
| LSI 5p15 | CEP 4 | LSI 8q24 | CEP 1 | | | | | |
| LSI 5p15 | CEP 4 | LSI 8q24 | CEP 6 | | | | | |
| LSI 5p15 | CEP 4 | LSI 7p12 | LSI 3q | | | | | |
| LSI 5p15 | CEP 4 | LSI 7p12 | CEP 6 | | | | | |
| LSI 5p15 | CEP 4 | LSI 3q | CEP 7 | | | | | |
| LSI 5p15 | CEP 4 | CEP 6 | CEP 7 | | | | | |
| LSI 5p15 | CEP 12 | LSI 8q24 | CEP 17 | | | | | |
| LSI 5p15 | CEP 12 | LSI 8q24 | CEP 1 | | | | | |
| LSI 5p15 | CEP 12 | LSI 8q24 | CEP 6 | | | | | |
| LSI 5p15 | CEP 12 | LSI 7p12 | LSI 3q | | | | | |
| LSI 5p15 | CEP 12 | LSI 7p12 | CEP 6 | | | | | |
| LSI 5p15 | CEP 12 | LSI 3q | CEP 7 | | | | | |
| LSI 5p15 | CEP 12 | CEP 6 | CEP 7 | | | | | |
| LSI 5p15 | CEP 6 | LSI 8q24 | CEP 17 | | | | | |
| LSI 5p15 | CEP 6 | LSI 8q24 | CEP 1 | | | | | |
| LSI 5p15 | CEP 6 | LSI 7p12 | LSI 3q | | | | | |
| LSI 5p15 | CEP 6 | LSI 3q | CEP 7 | | | | | |
| LSI 5p15 | LSI 17q21 | LSI 8q24 | CEP 17 | | | | | |
| LSI 5p15 | LSI 17q21 | LSI 8q24 | CEP 1 | | | | | |
| LSI 5p15 | LSI 17q21 | LSI 8q24 | CEP 6 | | | | | |
| LSI 5p15 | LSI 17q21 | LSI 7p12 | LSI 3q | | | | | |
| LSI 5p15 | LSI 17q21 | LSI 7p12 | CEP 6 | | | | | |
| LSI 5p15 | LSI 17q21 | LSI 3q | CEP 7 | | | | | |
| LSI 5p15 | LSI 17q21 | CEP 6 | CEP 7 | | | | | |
| LSI 8q24 | CEP 17 | LSI 7p12 | LSI 3q | | | | | |
| LSI 8q24 | CEP 17 | LSI 7p12 | CEP 6 | | | | | |
| LSI 8q24 | CEP 17 | LSI 3q | CEP 7 | | | | | |
| LSI 8q24 | CEP 17 | CEP 6 | CEP 7 | | | | | |
| LSI 8q24 | CEP 1 | LSI 7p12 | LSI 3q | | | | | |
| LSI 8q24 | CEP 1 | LSI 7p12 | CEP 6 | | | | | |
| LSI 8q24 | CEP 1 | LSI 3q | CEP 7 | | | | | |
| LSI 8q24 | CEP 1 | CEP 6 | CEP 7 | | | | | |
| LSI 8q24 | CEP 6 | LSI 7p12 | LSI 3q | | | | | |
| LSI 8q24 | CEP 6 | LSI 3q | CEP 7 | | | | | |
| LSI 7p12 | LSI 3q | CEP 6 | CEP 7 | | | | | |
| LSI 7p12 | CEP 6 | LSI 3q | CEP 7 | | | | | |

4 probe combinations - 3 pairs with 2 common probes:
examples:

| LSI 5p15 | LSI 8q24 | LSI 3q | CEP 1 | (probe pairs in rows 17 + 18 + 27) |
| LSI 5p15 | LSI 8q24 | LSI 3q | CEP 6 | (probe pairs in rows 17 + 18 + 28) |
| LSI 5p15 | LSI 8q24 | CEP 1 | CEP 6 | (probe pairs in rows 17 + 24 + 27) |
| LSI 7p12 | LSI 3q | CEP 6 | CEP 7 | (probe pairs in rows 29 + 30 + 31) | plus 3 probe labels) looking for cells with target gains. The number of targets for each of the 3 probes was recorded for any cell showing gain in one or more of the 3 targets.

Example 5

Detection of Lung Cancer in Bronchial Washing Specimens

The present study used an interphase FISH assay (using a 4-probe multicolor FISH panel) to detect lung cancer in 74 bronchial washing specimens that had previously been characterized by cytological analysis. Forty eight of the specimens were from patients with a clinical diagnosis of positive for cancer, and 26 of the specimens were from patients with a clinical diagnosis of negative for cancer.

Bronchial washing specimens were selected from the cytopathology archives of the Institute of Pathology in Basel, Switzerland. These cytology specimens were pre-stained with PAP stain and permanently mounted under coverslips. Specimens were archived for a period of time ranging from a few months to two years.

The four probes used for the FISH assay included a repetitive sequence probe centromeric to chromosome 1 (CEP 1), and three unique-sequence probes to the loci 5p15, 8q24 (containing the c-myc gene), and 7p12 (containing the EGFR gene), labeled respectively with SpectrumAqua™, SpectrumGreen™, SpectrumGold™, and SpectrumRed™. The probes were mixed together and hybridized simultaneously to each bronchial wash specimen.

The archived slides were soaked in xylene until the coverslips fell off (approximately 4-5 days) and then washed in fresh xylene twice, 5 minutes per wash. The slides were then placed in 95% ethanol, 85% ethanol, and 70% ethanol, sequentially (5 minutes per solution), followed by soaking the slides in 2×SSC buffer for 1 minute. The slides were then incubated in 0.5 mg/ml pepsin solution in 10 mM HCl for 10 minutes at 37° C., followed by a PBS wash for 5 minutes. The slides were fixed in a freshly prepared solution of 1% neutral buffered formalin for 5 minutes at 4° C., followed by soaking in PBS for 5 minutes. The slides were then denatured for 10 minutes in 70% formamide/2×SSC at 73° C., dehydrated in an ethanol series of 70%, 85%, and 100% ethanol (5 minutes per solution), and put on a slide warmer at 37-45° C. for 1 minute to dry. Probes in the hybridization mixture were denatured by placing the tube containing the mixture in a 73° C. water bath for 5 minutes. The denatured probe hybridization mixtures were applied to the specimens, covered with coverslips, and sealed with rubber cement. The slides were incubated at 37° C. overnight, after which the slides were washed in 2×SSC/0.3% NP40 at 73° C. for 2-5 minutes. The slides were then placed in 2×SSC/0.1% NP40 for several seconds to several minutes. DAPI II was applied to the target areas and the slides were analyzed under the fluorescence microscope using single bandpass filter sets.

The specimen slides were evaluated under a fluorescence microscope to first assess the technical quality of the FISH signals and the background staining. If the quality was acceptable, the slides were then enumerated. The overall sample appearance was evaluated with a DAPI single bandpass filter set at 40× magnification. The following sample features were important to note: 1) the presence of thin or thick mucous fibers; 2) the degree to which the cells were trapped within mucous fibers; 3) the presence of nuclear pleomorphism; and 4) the presence of disrupted cells (no clear nuclear borders, amorphous shape). Cells or groups of cells were selected for signal enumeration only if they had clearly defined nuclear borders and preferably were in the areas free of mucous fibers.

Enumeration was carried out according to the following rules using the DAPI single bandpass filter set and the three probe-specific single bandpass filter sets (Vysis aqua, green, gold, and red). All specimen evaluations were performed with the reviewer blinded to the identity of the specimen.

(1) Select the appropriate area with cells using the DAPI single bandpass filter set.

(2) Change to the gold or green single bandpass filter set and observe the field. If cells with signal copy gain are present, record the copy number pattern in those cells for all 4 probes, changing sequentially to the other three probe-specific single bandpass filter sets (order not important). If the cells look disomic with the gold or green filter set, change to one of the other three probe-specific filter sets and observe the field. If cells with signal copy gains are present, record their signal pattern for all 4 probes. Do this until the field has been scanned with all 4 probe-specific filter sets. Only record the pattern for any one cell once.

(3) Move to a new area and repeat the evaluation.

(4) Stop enumeration when at least 25 cells are scored or the end of the slide was reached.

Enumeration results of signal copy number for each probe were analyzed using JMP 3.2 version statistical software.

The samples used in this study were selected so that approximately half of the 48 specimens with a clinical diagnosis of cancer were also diagnosed as positive by cytology, and approximately half were diagnosed as negative by cytology. The majority of the cancer positive specimens were from patients with adenocarcinoma (23 specimens), followed by patients with squamous cell carcinoma (11 specimens). The rest of the specimens were from patients with large cell carcinoma (6 specimens), small cell carcinoma (6 specimens), carcinoid tumor (1 specimen), and leiomyosarcoma (1 specimen). All 26 specimens clinically negative for cancer had negative cytology results. No specimens were selected with a negative clinical diagnosis and a positive cytology result (the cytology specificity in this study was 100% by design).

Table 14 shows the distribution of the cytology results in the cohort of patients that was used in this study. The cytology results were positive for 22 patients, negative for 48 patients and suspicious for 4 patients. The sensitivity of cytology for the group of 48 samples positive for cancer by clinical diagnosis was 45.8%. Thirteen specimens were rejected from FISH evaluation due to the excessive loss of tissue (9 specimens from cancer positive patients and 4 specimens from cancer negative patients). Excluding the slides that were not evaluated by FISH, the cytology sensitivity for the remaining 39 cancer positive patients was 50%. If cytology suspicious samples were counted as positive, the cytology sensitivity increased to 53.9%.

TABLE 14

Correlation Between Cytology Results and Clinical Diagnosis

| Cytology | Clinical Diagnosis | |
|---|---|---|
| | Cancer Negative | Cancer Positive |
| Cytology Negative | 26 (100%) | 22 (45.83%) |
| Cytology Positive | 0 (0%) | 22 (45.83%) |
| Cytology Suspicious | 0 (0%) | 4 (8.33%) |

The bronchial washing specimens were hybridized with the multicolor FISH probe mixture after the coverslips were removed by soaking in xylene. The overall appearance of each sample, was evaluated. If the specimen appeared to be extremely acellular or the morphology of the cells was disturbed, or the hybridization signal was too weak, then the sample was rejected for FISH enumeration.

To evaluate the FISH results, it was necessary to develop a cancer positivity criteria. This involved developing rules to classify individual cells as being suspicious for malignancy ("abnormal") or not suspicious ("normal"), and setting cutoff values for the minimum number of abnormal cells required to classify a specimen as positive for cancer.

A cell was classified as abnormal if it showed copy number gains for at least two probes included in the probe mix (this was termed "Multiple DNA loci gain"). Once this rule was established, all of the specimen data were evaluated and the number of "abnormal" cells in each of the specimens was tabulated. To decide what should be the "cancer positivity criteria" (a quantitative measure to discern cancer negative from cancer positive cases), the receiver operator characteristic (ROC) curve approach was applied to the data analysis. Using this approach, a series of tentative cutoff points are set and the sensitivity and specificity are calculated at each point. For data presented here, cutoff values of 1 to 110 cells per specimen were used. For each cutoff value the sensitivity was determined for the cohort of cancer positive patients, and the specificity was determined for the cohort of cancer negative patients. Then the ROC curve was plotted for sensitivity (y axis) as a function of [1−specificity] (x axis) (FIG. 1).

As seen in FIG. 1, there is a section on the curve, where the sensitivity increases significantly while specificity remains about the same. The cutoff point is often selected in the section where the curve turns. The turning point in this assay corresponded to a cutoff value of finding 5-6 cells that met the criteria of cancer positivity. Consequently, the rule for classifying a specimen as positive used in this study was as follows: if a sample contained 6 or more abnormal cells with "multiple loci gain," it was classified as "cancer positive." If a sample had less than 6 abnormal cells, it was classified as "cancer negative."

Table 15 shows the correlation between cytology and FISH results for the group of "cancer positive" patients. Cytology was positive in 22 out of 48 "cancer positive" patients, providing a sensitivity of 45.8%. For another 4 specimens the cytology was reevaluated by cytopathologists, and the specimens classified as "suspicious". If "suspicious" results were interpreted as "cancer positive", then the sensitivity of cytology became 53.8%. Several samples were rejected from FISH evaluation due to low cellularity and other reasons, so the number of cases evaluated by FISH was different from the number of cases evaluated by cytology. Recalculating the cytology results for those cases that were also evaluated by FISH, the sensitivity of cytology became 46.2% (18/39 cases), if "suspicious" results are counted as positive results, the sensitivity would be 53.8%. Thus, there was no significant difference between the sensitivity results if FISH-rejected samples were included or excluded from the calculations. The FISH results for the same group of patients showed 32 positive results among the 39 "cancer positive" patients, providing a sensitivity of 82.0%.

TABLE 15

Cancer Positive Patients: Correlation of FISH and Cytology Results

|  | FISH Negative | FISH Positive | FISH Rejected | Total |
|---|---|---|---|---|
| Cytology Negative | 3 | 15 | 4 | 22 |
| Cytology Positive | 3 | 15 | 4 | 22 |
| Cytology Suspicious | 1 | 2 | 1 | 4 |
| Total | 7 | 32 | 9 | 48 |

FISH was able to clarify two of the cytology suspicious specimens (an additional specimen was rejected for FISH evaluation) by placing them into the category of "cancer positive" specimens. The number of abnormal cells in each of those specimens was 8 for a small cell carcinoma specimen and 10 for a large cell carcinoma specimen. Even more important are the results obtained for the group of 18 cytology negative/cancer positive cases. Table 15 shows that for these cancer patients that were missed by cytology, FISH was positive in 15/18 cases, thus improving the diagnosis in 83.3% of cases.

FISH and cytology results were also analyzed relative to the type of tumor. The data showed that FISH had its lowest sensitivity for the specimens diagnosed as squamous-cell carcinoma (5/9 specimens, 55.5%). For this type of lung tumor, cytology showed 54.5% sensitivity. Adenocarcinoma, large cell carcinoma, and small cell carcinoma demonstrated sensitivity by FISH of 86.4% (19/22 cases), 100% (5/5 cases) and 100% (3/3 cases), respectively. Cytology sensitivity for these tumors was as follows: 60.9% for adenocarcinoma; 50% for large cell carcinoma; and 100% for small cell carcinoma.

The group of "cancer negative" patients consisted of 26 patients. Cytology results were negative for all of the patients in this selected group setting the specificity of 100%. Four specimens were rejected from FISH evaluation due to low cellularity, thus only 22 specimens were evaluated. Among those 22 specimens, FISH was clearly negative in 18 patients providing a specificity of 81.8% (Table 16). Four specimens had positive FISH results. These four specimens contained as many as 19, 15, 11 and 8 "abnormal" cells per 25 evaluated suspicious cells. It is also important to note that in two of the specimens, the magnitude of copy number gain was as high as 7-8 copies per cell in one case and 11-2 copies per cell in another case. One of the specimens was derived from a patient diagnosed with advanced colorectal cancer approximately one year before the specimen was prepared (the patient died by the time of the present study). Another patient had a previous history of heavy smoking and had the occupational hazard of being a miner. Thus, it is possible that these FISH positive, but "cytology negative" specimens were derived from patients at risk of developing lung cancer.

TABLE 16

Cancer Negative Patients: Correlation of FISH and Cytology Results

|  | FISH Negative | FISH Positive | FISH Rejected | Total |
|---|---|---|---|---|
| Cytology Negative | 18 | 4 | 4 | 26 |
| Cytology Positive/Suspicious | 0 | 0 | 0 | 0 |
| Total | 18 | 4 | 4 | 26 |

Table 17 shows comparative data on sensitivity and specificity for cytology and FISH for the total population of 74 patients.

TABLE 17

Total population of patients: Correlation of FISH and cytology results

|  | FISH Negative | FISH Positive | FISH Rejected | Total |
|---|---|---|---|---|
| Cytology Negative | 21 | 19 | 8 | 48 |
| Cytology Positive | 3 | 15 | 4 | 22 |
| Cytology Suspicious | 1 | 2 | 1 | 4 |
| Total | 25 | 36 | 13 | 74 |

Example 6

Detection of Lung Cancer in Bronchoscopic Specimens

The present study used an interphase FISH assay (using a 4-probe multicolor FISH panel) to detect lung cancer in 191 bronchial specimens that had previously been characterized by surgical pathology analysis. The surgical pathology results of the specimens used in this study are summarized in Table 18. 104 of the specimens (55%) were from patients with a clinical diagnosis of positive for lung cancer. 84 of the specimens (44%) were from patients with a clinical diagnosis of negative for lung cancer.

TABLE 18

Surgical Pathology Results of Specimens Used in Study

| Number of Specimens | Diagnosis (+ or − for cancer) | Percentage |
|---|---|---|
| 104 | + | 55 |
| 84 | − | 44 |
| 3 | Equivocal diagnosis | 1 |

One of the following three sets of four probes was used for each FISH assay: (1) a repetitive sequence probe centromeric to chromosome 1 (CEP 1), and three unique-sequence probes to the loci 5p15, 8q24; and 7p12; (2) repetitive sequence probes centromeric to chromosome 16 (CEP 16) and chromosome 17 (CEP 17) and two unique-sequence probes to the loci 3q26 and 20q13; or (3) a repetitive sequence probe centromeric to chromosome 6 (CEP 6) and three unique-sequence probes to the loci 5p15, 8q24, and 7p12. The probes were mixed together and hybridized simultaneously to each bronchial specimen.

The sensitivity, detected by each of FISH and cytology analysis for the 104 cancer positive specimens is depicted in Table 19 (38 bronchial brushing samples) and Table 20 (66 bronchial secretion samples). As shown in Table 19, FISH demonstrated a significantly enhanced sensitivity (72%) as compared to cytology (51%) for the bronchial brushing samples. No significant difference between FISH and cytology was detected for the bronchial secretion samples (Table 20).

TABLE 19

Sensitivity of FISH and Cytology for Bronchial Brushing Samples

| Analysis | Diagnosis | Number | Percentage |
|---|---|---|---|
| FISH | + | 26/36 | 72 |
| FISH | − | 8/36 | 22 |
| FISH | Equivocal diagnosis | 2/36 | 6 |
| Cytology | + | 19/37 | 51 |
| Cytology | − | 17/37 | 46 |
| Cytology | Equivocal diagnosis | 1/37 | 3 |

TABLE 20

Sensitivity of FISH and Cytology for Bronchial Secretion Samples

| Analysis | Diagnosis | Number | Percentage |
|---|---|---|---|
| FISH | + | 31/65 | 48 |
| FISH | − | 28/65 | 43 |
| FISH | Equivocal diagnosis | 6/65 | 9 |
| Cytology | + | 34/66 | 52 |
| Cytology | − | 28/66 | 42 |
| Cytology | Equivocal diagnosis | 4/66 | 6 |

The specificity detected by FISH and cytology analysis for the 84 specimens negative for lung cancer (as determined by surgical pathological analysis) is depicted in Table 21 (49 bronchial brushing samples) and Table 22 (35 bronchial secretion samples). It is expected that among those samples described in Tables 21 and 22 that were negative by surgical pathological analysis, but positive by FISH analysis, there may be some specimens that contain cancerous and/or pre-cancerous cells that were not identified by the surgical pathology methods. In such cases, FISH can allow for an early detection of lung cancer.

TABLE 21

Specificity of FISH and Cytology for Bronchial Brushing Samples

| Analysis | Diagnosis | Number | Percentage |
|---|---|---|---|
| FISH | + | 10/49 | 20 |
| FISH | − | 38/49 | 78 |
| FISH | Equivocal diagnosis | 1/49 | 2 |
| Cytology | + | 2/49 | 4 |
| Cytology | − | 47/49 | 96 |
| Cytology | Equivocal diagnosis | 0/49 | 0 |

TABLE 22

Specificity of FISH and Cytology for Bronchial Secretion Samples

| Analysis | Diagnosis | Number | Percentage |
|---|---|---|---|
| FISH | + | 3/35 | 8 |
| FISH | − | 31/35 | 88 |
| FISH | Equivocal diagnosis | 1/35 | 3 |
| Cytology | + | 4/35 | 11 |
| Cytology | − | 29/35 | 83 |
| Cytology | Equivocal diagnosis | 2/35 | 6 |

Other Embodiments

It is to be understood that, while the invention has been described in conjunction with the detailed description thereof, the foregoing description is intended to illustrate and not limit the scope of the invention. Other aspects, advantages, and modifications of the invention are within the scope of the claims set forth below.

The invention claimed is:

1. A method of screening for lung cancer in a human subject whose status with respect to lung cancer is unknown, the method comprising:
    a) obtaining a biological sample, wherein the biological sample comprises a lung sample, from the subject;
    b) obtaining a set of chromosomal probes consisting of two probes said two probes suitable for detecting lung cancer with greater sensitivity and specificity together than each individual probe, said set of two probes consisting of a 5p15 locus specific probe with a target location of D5S721.D5S23 and a chromosome 6 enumeration probe with a target location of D6Z1.6p11.1-q11;
    c) contacting the set of probes to the biological sample under conditions sufficient to enable hybridization of probes in the set to chromosomes in the sample, if any; and
    d) detecting a hybridization pattern consisting of gains or losses of copy number of chromosomal target regions as determined by the set of chromosomal probes hybridized to the chromosomes in the biological sample to determine whether the subject has lung cancer.

2. The method of claim 1, wherein the biological sample consists of one or more of a bronchial specimen, a lung biopsy, or a sputum sample.

3. The method of claim 1, wherein the chromosomal probes are fluorescently labeled.

4. The method of claim 1, further comprising performing cytological analysis on the sample.

* * * * *